United States Patent
Woodburn et al.

(10) Patent No.: US 10,188,439 B2
(45) Date of Patent: Jan. 29, 2019

(54) BONE FIXATION SYSTEM

(71) Applicant: DePuy Synthes Products, Inc., Raynham, MA (US)

(72) Inventors: William N. Woodburn, Mantua, NJ (US); Jason S. Chan, Dresher, PA (US); Mark P. Grady, West Chester, PA (US); Robert J. Schoutens, Basel (CH)

(73) Assignee: DePuy Synthes Products, Inc., Raynham, MA (US)

( * ) Notice: Subject to any disclaimer, the term of this patent is extended or adjusted under 35 U.S.C. 154(b) by 27 days.

(21) Appl. No.: 14/977,894

(22) Filed: Dec. 22, 2015

(65) Prior Publication Data

US 2016/0106485 A1    Apr. 21, 2016

Related U.S. Application Data

(63) Continuation of application No. 14/324,318, filed on Jul. 7, 2014.

(60) Provisional application No. 61/843,999, filed on Jul. 9, 2013.

(51) Int. Cl.
| | | |
|---|---|---|
| *A61B 17/56* | (2006.01) | |
| *A61B 17/58* | (2006.01) | |
| *A61B 17/80* | (2006.01) | |
| *A61F 2/30* | (2006.01) | |
| *A61B 17/70* | (2006.01) | |
| *A61B 17/86* | (2006.01) | |

(52) U.S. Cl.
CPC ...... *A61B 17/8085* (2013.01); *A61B 17/7059* (2013.01); *A61B 17/8023* (2013.01); *A61B 17/8047* (2013.01); *A61B 17/8057* (2013.01); *A61B 17/8071* (2013.01); *A61B 17/8625* (2013.01)

(58) Field of Classification Search
CPC . A61B 17/80; A61B 17/8004; A61B 17/8009; A61B 17/8023; A61B 17/8061; A61B 17/8071; A61B 17/8085; A61B 17/7059; A61B 17/8047
USPC .................................................. 403/104-107
See application file for complete search history.

(56) References Cited

U.S. PATENT DOCUMENTS

| | | |
|---|---|---|
| 870,242 A | 11/1907 | Meech |
| 1,182,980 A | 5/1916 | Converse |
| 2,035,308 A | 6/1936 | Ferber |
| 3,488,779 A | 1/1970 | Christensen |
| 3,805,302 A | 4/1974 | Mathys |
| 4,429,690 A | 2/1984 | Angelino-Pievani |
| 5,053,036 A | 10/1991 | Perren et al. |
| 5,704,936 A | 1/1998 | Mazel |
| 5,713,900 A | 2/1998 | Benzel et al. |

(Continued)

FOREIGN PATENT DOCUMENTS

| | | |
|---|---|---|
| CN | 1700890 | 11/2005 |
| CN | 1985770 | 6/2007 |

(Continued)

*Primary Examiner* — Si Ming Ku

(74) *Attorney, Agent, or Firm* — Baker & Hostetler LLP

(57) ABSTRACT

A modular bone fixation linkage includes a plurality of interconnected links that can angulate with respect to an adjacent one of the links about at least one axis, such as three axes. The links can further include fixation holes that are configured to receive bone anchors that secure the links to an underlying anatomical structure.

26 Claims, 28 Drawing Sheets

(56) References Cited

U.S. PATENT DOCUMENTS

| | | | |
|---|---|---|---|
| 5,975,904 A | 11/1999 | Spiegel | |
| 6,030,389 A | 2/2000 | Wagner et al. | |
| 6,053,921 A | 4/2000 | Wagner et al. | |
| 6,060,641 A | 5/2000 | Manolidis | |
| 6,136,002 A | 10/2000 | Shih et al. | |
| 6,730,091 B1 | 5/2004 | Pfefferle et al. | |
| 6,749,612 B1 | 6/2004 | Conchy et al. | |
| 7,090,676 B2 | 8/2006 | Huebner et al. | |
| 7,201,753 B2 | 4/2007 | Schlaapfer et al. | |
| 7,935,126 B2 | 5/2011 | Orbay et al. | |
| 7,988,691 B2 | 8/2011 | Schulze et al. | |
| 8,221,472 B2 | 7/2012 | Peterson et al. | |
| 8,343,154 B2 | 1/2013 | Long et al. | |
| 8,343,196 B2 * | 1/2013 | Schneider | A61B 17/8052 606/286 |
| 8,506,605 B2 | 8/2013 | Bickley et al. | |
| 8,795,277 B2 | 8/2014 | Leuenberger et al. | |
| 9,101,428 B2 | 8/2015 | Long et al. | |
| 2001/0034521 A1 | 10/2001 | Bailey et al. | |
| 2002/0183756 A1 * | 12/2002 | Michelson | A61B 17/7059 606/71 |
| 2004/0039388 A1 | 2/2004 | Biedermann et al. | |
| 2004/0092930 A1 | 5/2004 | Petit et al. | |
| 2004/0102778 A1 | 5/2004 | Huebner et al. | |
| 2004/0116931 A1 | 6/2004 | Carlson | |
| 2005/0027298 A1 | 2/2005 | Michelson | |
| 2005/0154388 A1 | 7/2005 | Roussouly et al. | |
| 2005/0277920 A1 | 12/2005 | Slivka et al. | |
| 2006/0149228 A1 | 7/2006 | Schlapfer et al. | |
| 2007/0123881 A1 | 5/2007 | Ralph et al. | |
| 2007/0233085 A1 | 10/2007 | Biedermann et al. | |
| 2007/0293863 A1 | 12/2007 | Reimels et al. | |
| 2008/0097432 A1 | 4/2008 | Schulze et al. | |
| 2008/0097445 A1 | 4/2008 | Weinstein | |
| 2008/0140130 A1 | 6/2008 | Chan et al. | |
| 2008/0234676 A1 | 9/2008 | Schulze et al. | |
| 2009/0082813 A1 * | 3/2009 | Long | A61B 17/80 606/282 |
| 2010/0121328 A1 | 5/2010 | Reitzig et al. | |
| 2010/0179552 A1 | 7/2010 | Wolter | |
| 2010/0274248 A1 | 10/2010 | Overes et al. | |
| 2010/0305569 A1 | 12/2010 | Leuenberger | |
| 2010/0324558 A1 | 12/2010 | Bickley et al. | |
| 2011/0218534 A1 * | 9/2011 | Prandi | A61B 17/80 606/71 |
| 2011/0270316 A1 | 11/2011 | Piehl | |
| 2012/0184995 A1 | 7/2012 | Miller | |

FOREIGN PATENT DOCUMENTS

| | | |
|---|---|---|
| CN | 1985771 | 6/2007 |
| CN | 101594834 A | 12/2009 |
| DE | 20 2007001585 U1 | 5/2007 |
| EP | 1861030 A2 | 12/2007 |
| JP | 7501735 | 2/1995 |
| JP | 2002-527137 | 8/2002 |
| JP | 2007-517584 | 7/2007 |
| JP | 2009-513245 | 4/2009 |
| WO | WO 2005/069752 | 8/2005 |
| WO | WO 2006/102222 A2 | 9/2006 |
| WO | WO 2007/050276 | 5/2007 |
| WO | WO 2009/049161 | 4/2009 |
| WO | 2015/006188 A1 | 1/2015 |

* cited by examiner

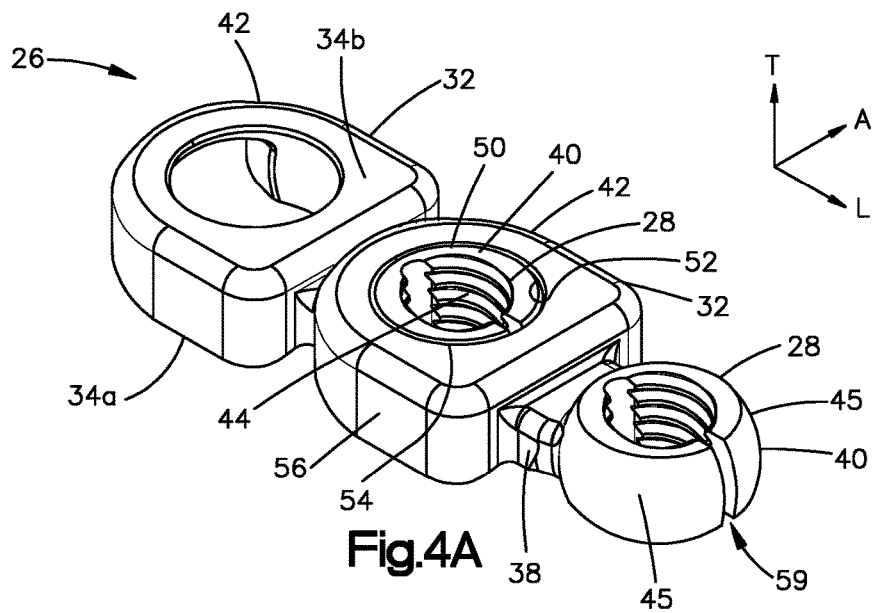
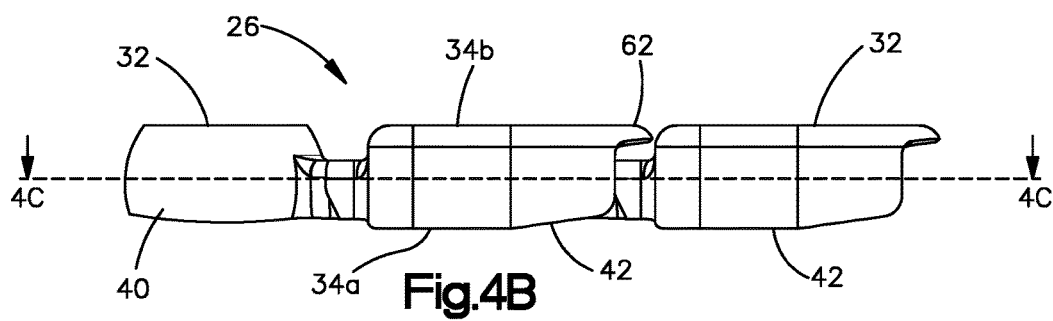
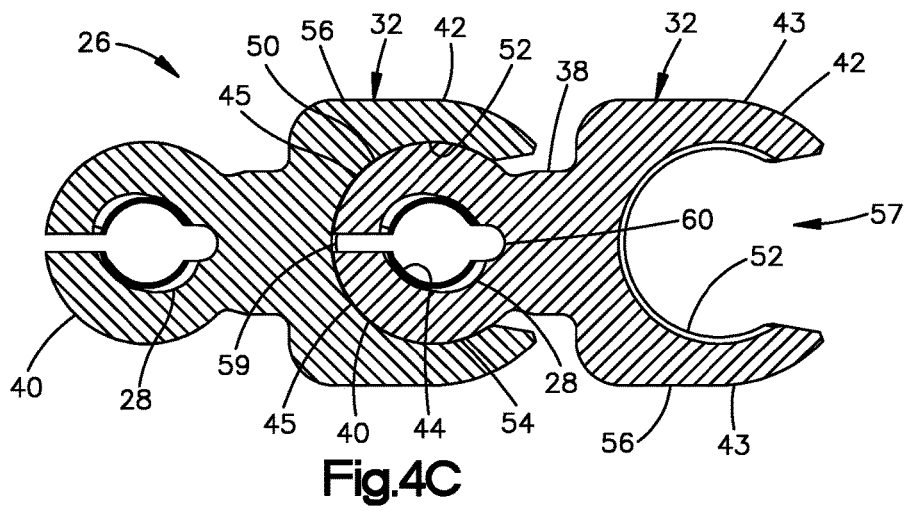

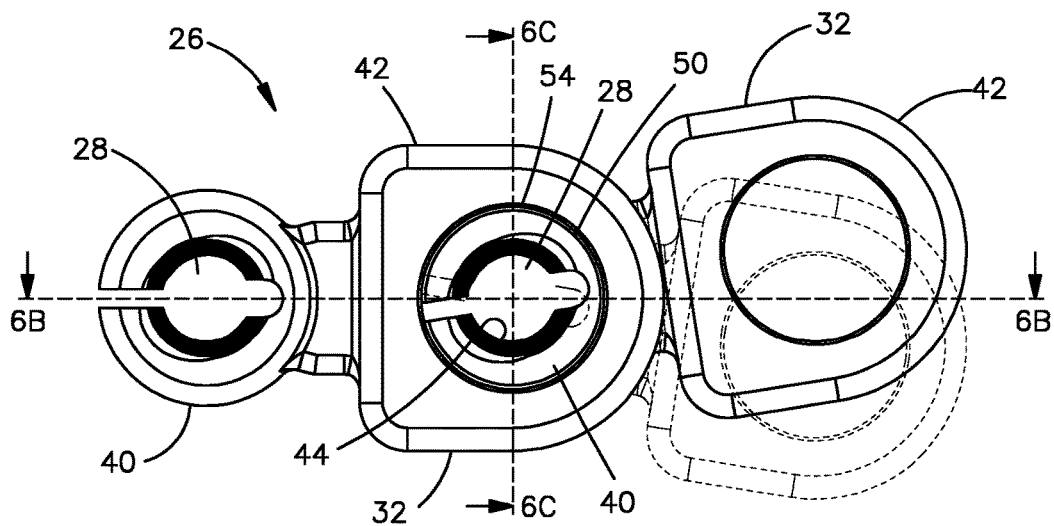
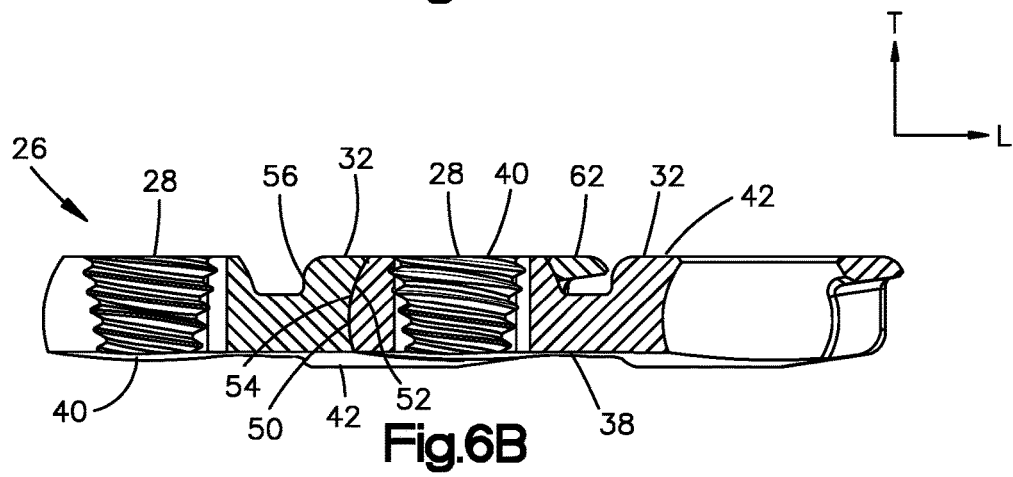
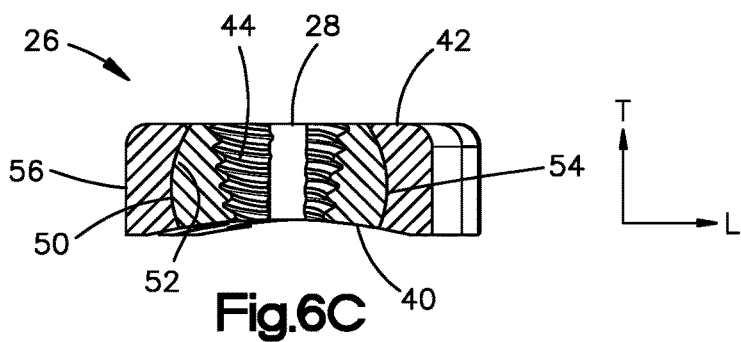

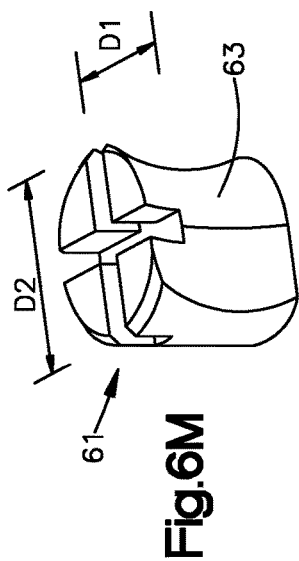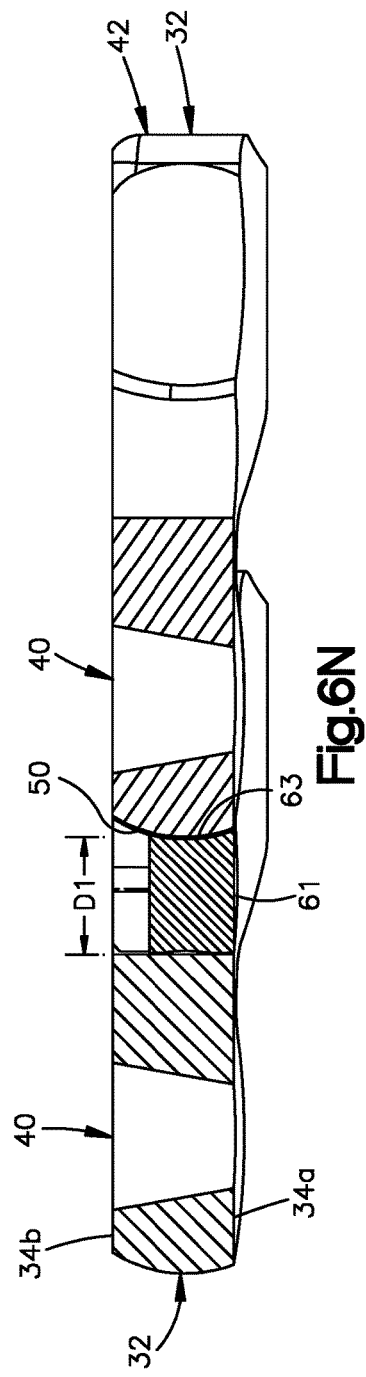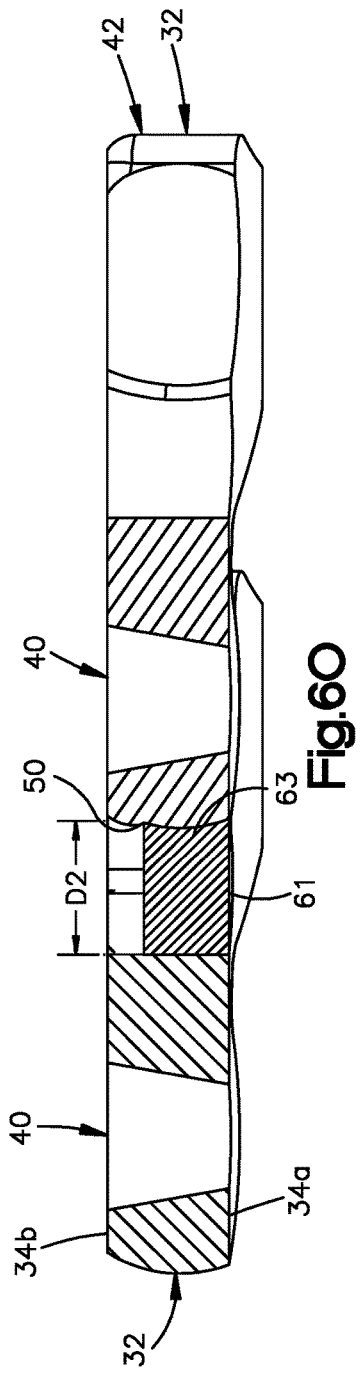

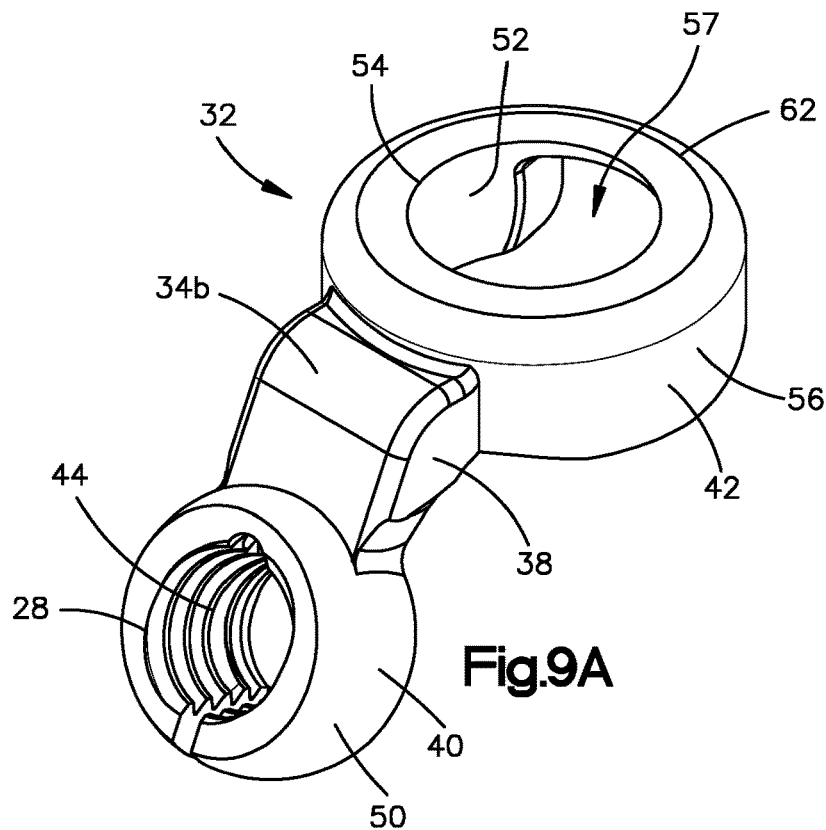
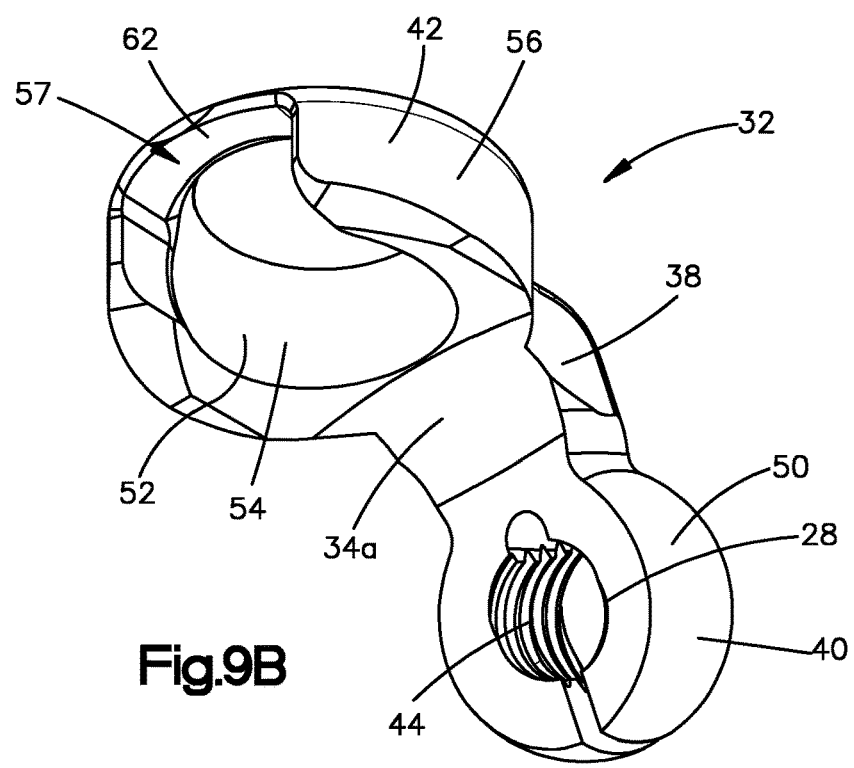

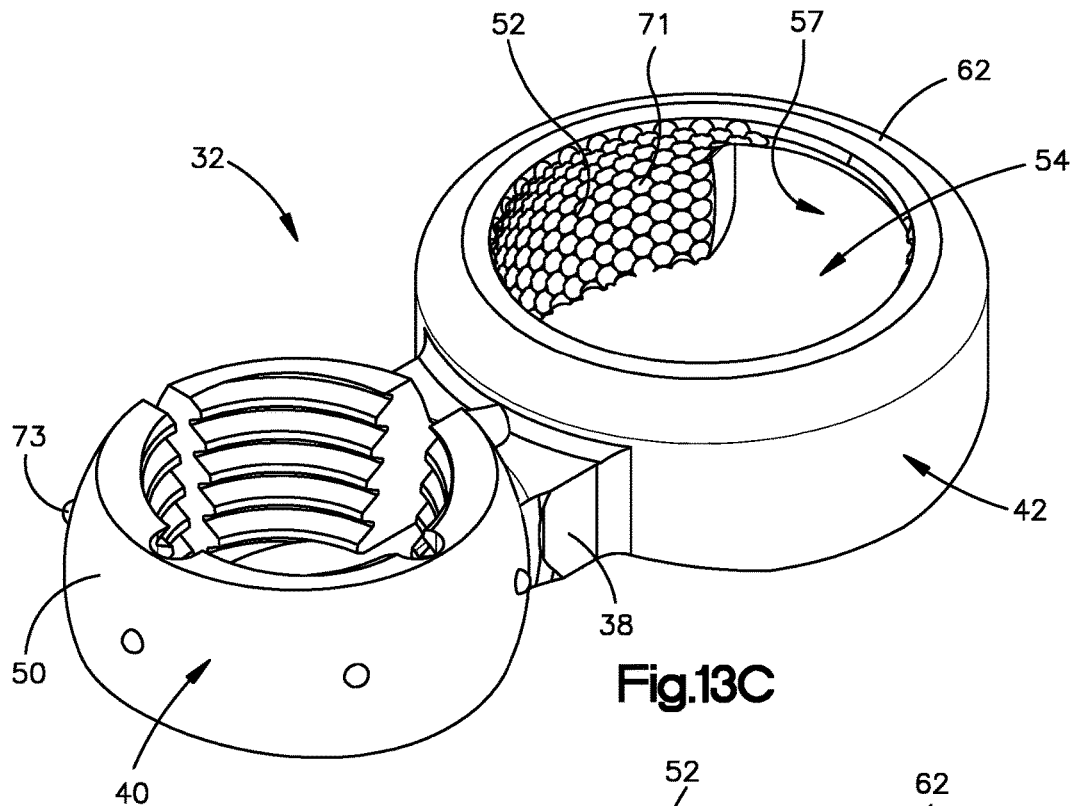
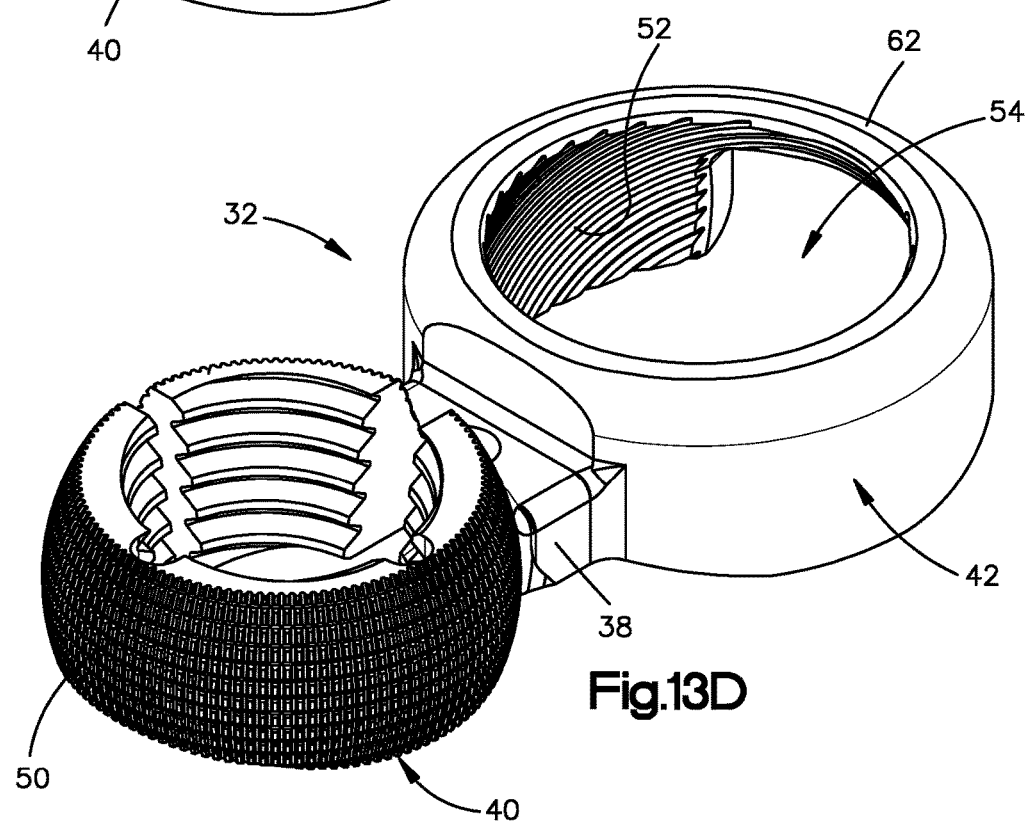

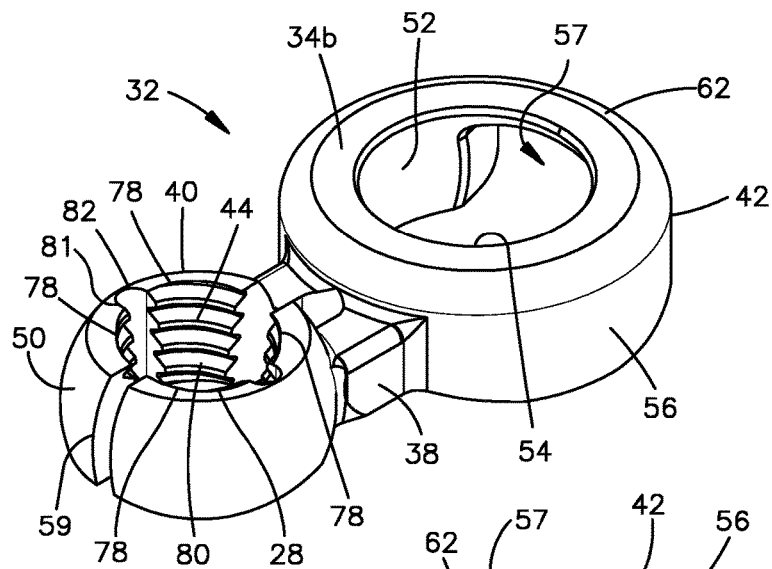
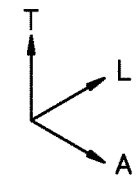
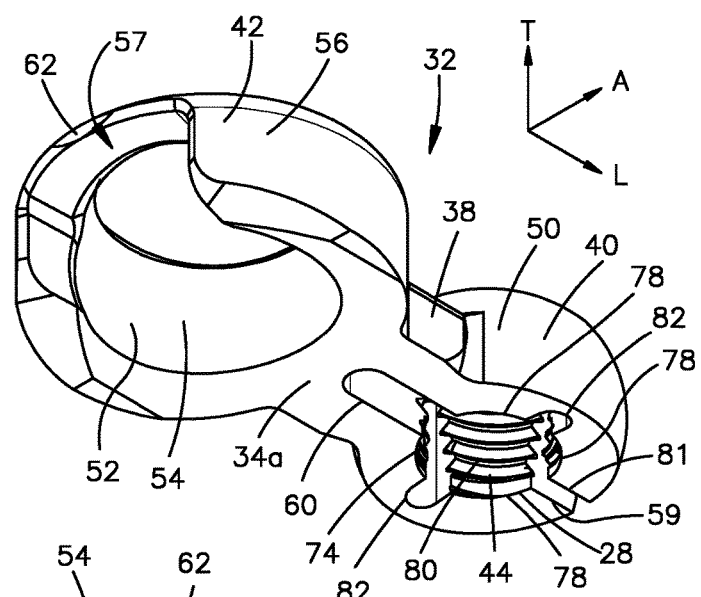
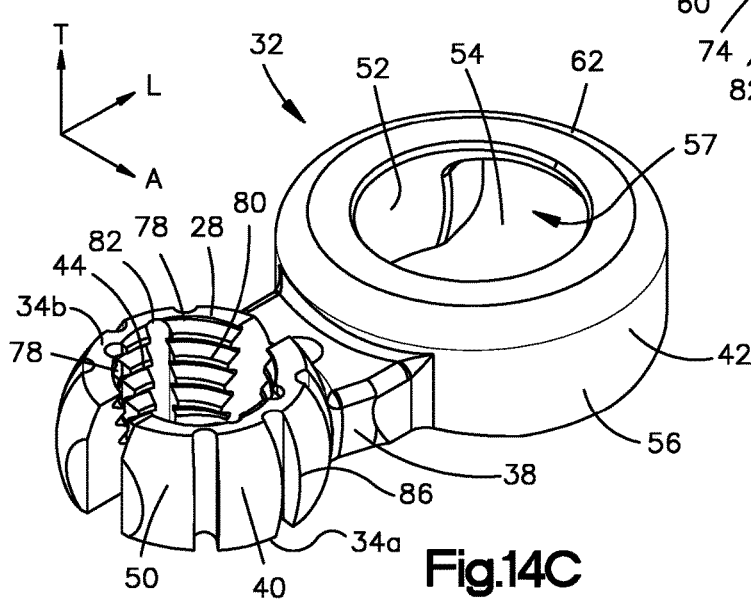

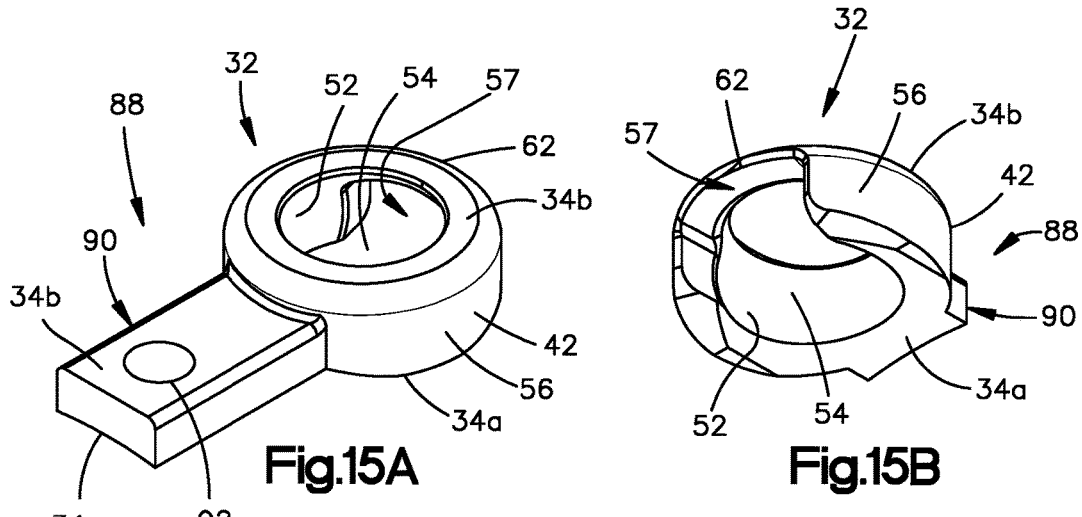
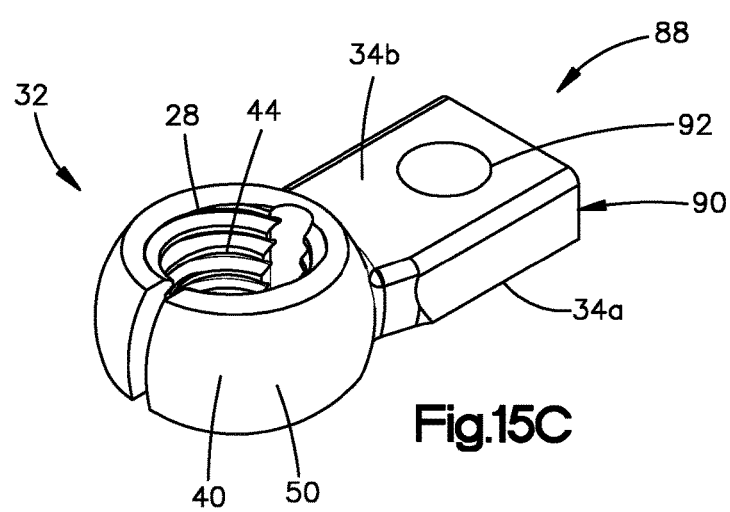
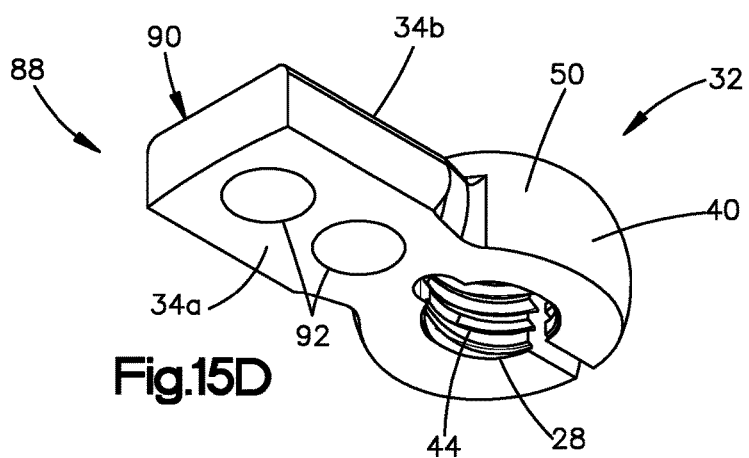

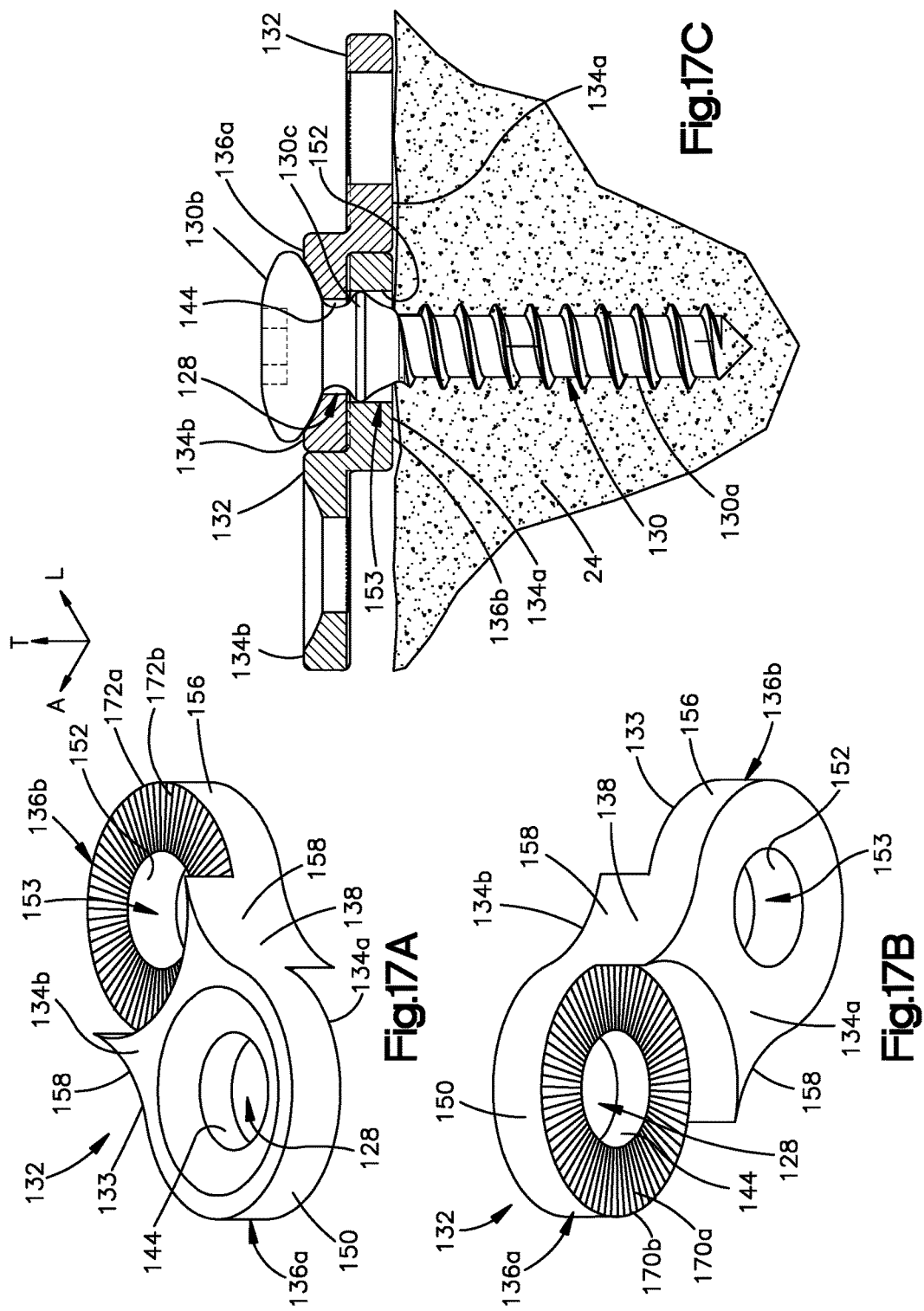

BONE FIXATION SYSTEM

CROSS-REFERENCE TO RELATED APPLICATIONS

This application is a continuation application of U.S. patent application Ser. No. 14/324,318, filed Jul. 7, 2014, which claims the benefit of U.S. Patent Application Ser. No. 61/843,999, filed Jul. 9, 2013, the disclosures of both of which are hereby incorporated by reference as if set forth in their entirety herein.

BACKGROUND

This disclosure relates generally to bone fixation implants, and in particular relates to an adaptable bone fixation implant that can be readily shaped to repair or replace a particular bone structure of a patient.

When bones are damaged through trauma, disease, distraction osteogenesis, or orthognathic surgery, bone fixation implants are commonly used to provide anatomical reduction of bone fragments, to maintain their position, and to ensure union in the desired position. Thus, bone fixation implants are typically designed to achieve proper anatomic fit and function. Additionally, because bone fixation implants often support bones that withstand significant mechanical stress in their anatomic function, implants are often composed of strong and rigid materials. However, it is particularly difficult to fashion rigid materials to a particular patient's bone contour.

As one example, achieving the proper shape and fit of a bone fixation implant is of particular emphasis in mandibular reconstruction. An improper fit of a mandibular fixation implant may result in disruption of the normal jaw function or alteration of the occlusion, which can cause discomfort for a patient. Additionally, it is desirable for mandibular fixation implants to be strong and rigid to provide a proper occlusion and withstand related mechanical stresses.

SUMMARY

In accordance with one embodiment, a bone fixation linkage can include a plurality of interconnected links each defining a first end configured to face a bone to which the bone fixation linkage is configured to be attached, and a second end opposite the first end. The bone fixation linkage can further include at least a first link of the plurality of interconnected links including a first insertion member, a first receptacle member, and a first neck that extends from the insertion member to the first receptacle member and is monolithic with the first insertion member and the first receptacle member. The bone fixation linkage can further include at least a second link of the plurality of interconnected links including a second insertion member, a second receptacle member, and a second neck that extends from the second insertion member to the second receptacle member and is monolithic with the second insertion member and the second receptacle member. Each of the first and second insertion members can include a first interior surface that defines a fixation hole and a first outer surface that is opposite the interior surface, and each of the first and second receptacle members can include a second interior surface that defines a receptacle. The first insertion member of the first link can be captured by the second interior surface of the second link such that the first and second links are angulatable with respect to each other about at least one axis. The first outer surface of the first link can be is configured to ride along the second interior surface of the second link as the first and second links angulate with respect to each other about the at least one axis.

BRIEF DESCRIPTION OF THE DRAWINGS

The foregoing summary, as well as the following detailed description, is better understood when read in conjunction with the appended drawings. For the purpose of illustrating the reconstruction device and related method thereof, there is shown in the drawings exemplary embodiments, in which like reference numerals correspond to like reference numerals throughout. The reconstruction device and related methods are not limited to the specific embodiments and methods disclosed, and reference is made to the claims for that purpose.

FIG. 4A is a perspective view of a linkage including first and second links shown joined to each other, shown in a neutral position;

FIG. 4B is a side elevation view of the first and second links illustrated in FIG. 4A;

FIG. 4C is a sectional top plan view taken along line 4C-4C of FIG. 4B;

FIG. 6A is a top plan view of the linkage illustrated in FIG. 4A, shown in an angulated position about a transverse axis;

FIG. 6B is a sectional side elevation view of the linkage illustrated in FIG. 6A, taken along line 6B-6B;

FIG. 6C is a sectional end elevation view of the linkage illustrated in FIG. 6A, taken along line 6C-6C;

FIG. 6M is a perspective view showing the cam member illustrated in FIG. 6K;

FIG. 6N is a sectional elevation view of the linkage illustrated in FIG. 6L, showing the cam member in an unlocked position;

FIG. 6O is a sectional elevation view of the linkage illustrated in FIG. 6L, showing the cam member in a locked position;

FIG. 9A is a perspective view of a link similar to the link illustrated in FIG. 3A, but showing the insertion member angularly offset with respect to the receptacle member;

FIG. 9B is another perspective view of the link illustrated in FIG. 9A;

FIG. 13C is a perspective view of a link having raised regions in accordance with another embodiment;

FIG. 13D is a FIG. 13C is a perspective view of a link having raised regions in accordance with yet another embodiment;

FIG. 14A is a perspective view of a link similar to the link illustrated in FIG. 3A, but showing the insertion member including a variable angle fixation hole;

FIG. 14B is another perspective view of the link illustrated in FIG. 14A;

FIG. 14C is a perspective view of a link similar to the link illustrated in FIG. 14A, but showing the insertion member externally splined;

FIG. 15A is a perspective view of a portion of a bone plate including a receptacle member of the type illustrated in FIG. 3A;

FIG. 15B is another perspective view of the portion of the bone plate illustrated in FIG. 15A;

FIG. 15C is a perspective view of a portion of a bone plate including an insertion member of the type illustrated in FIG. 3A;

FIG. 15D is another perspective view of the portion of the bone plate illustrated in FIG. 15C;

FIG. 17A is a perspective view of a link constructed in accordance with another embodiment;

FIG. 17B is another perspective view of the link illustrated in FIG. 17A; and

FIG. 17C is a side elevation view of a linkage including a plurality of links as illustrated in FIG. 17A.

DETAILED DESCRIPTION OF ILLUSTRATIVE EMBODIMENTS

Figure 1:
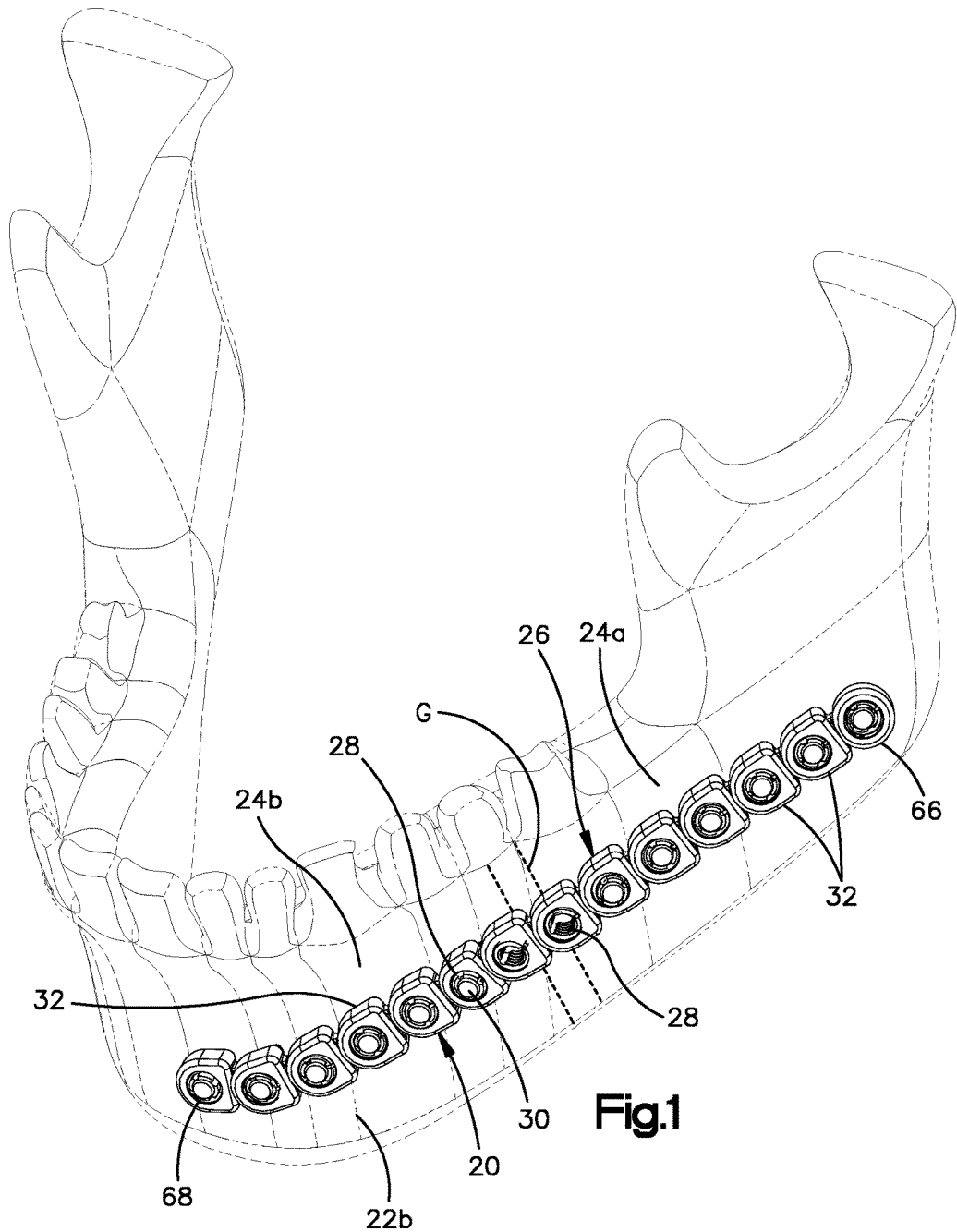
FIG. 1 is a perspective view of a bone fixation system including a bone fixation linkage and a plurality of bone anchors, shown implanted onto a target bone in accordance one embodiment.
Figure 2A:
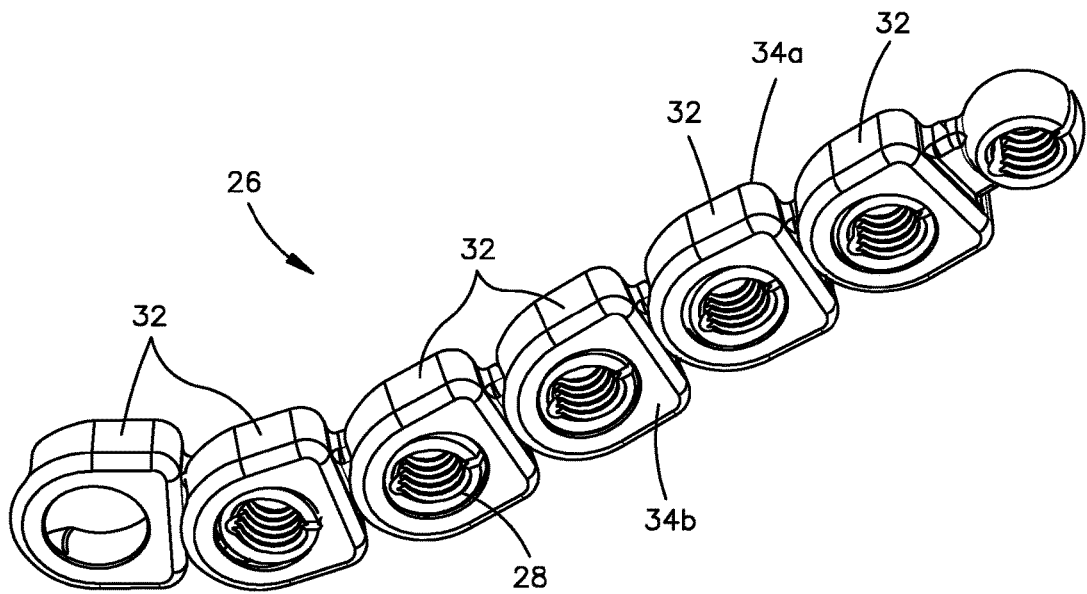
FIG. 2A is an enlarged perspective view of a bone fixation linkage similar to the bone fixation linkage illustrated in FIG. 1, including a plurality of interconnected links.
Figure 2B:
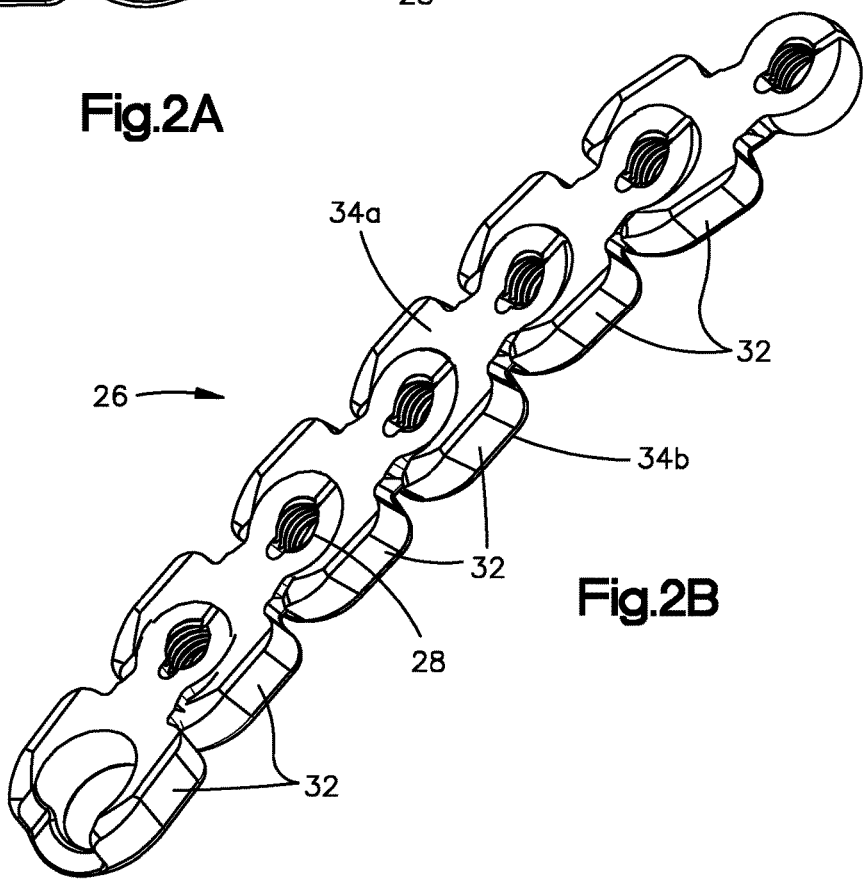
FIG. 2B is another perspective view of the bone fixation linkage illustrated in FIG. 2A.

Referring to FIGS. 1-2B, a bone fixation system 20 is configured to be implanted onto bone so as to stabilize a first anatomical structure 22*a* with respect to at least second anatomical structure 22*b* so as to promote bone healing. In particular, the bone fixation system 20 can include a bone fixation linkage 26 that defines a plurality of fixation holes 28, which can be bone fixation holes configured to receive a plurality of bone anchors 30, such as bone screws, that are configured to be driven through respective ones of the fixation holes 28 and into a respective one of the first and second anatomical structures 22a and 22b, until respective heads of the bone anchors 30 engage the bone fixation linkage 26, thereby securing the bone fixation linkage 26 to the first and second anatomical structures 22a and 22b. Thus, the bone fixation system 20 can include at least one bone fixation linkage 26 and at least one bone anchor 30 such as a plurality of bone anchors 30.

The first anatomical structure 22a can be configured as a bone or bone fragment 24a as illustrated. The term "bone" can be used to refer collectively to bone or a bone fragment. The second anatomical structure 22b can be configured as another bone fragment 24b, separated by a bone gap G, for instance when a bone is fractured, or when an osteotomy is performed on a bone 24. The second anatomical structure 22b can also be another bone fragment when a bone is resectioned so as to define a bone gap that separates the first and second bone fragments. Alternatively or additionally, the bone fixation system 20 is configured to stabilize the first anatomical structure with respect to a bone implant, which can be an artificial implant or a bone graft. In one example, the bone graft can be placed in the bone gap, for instance after resection. Thus, the second anatomical structure 22b can be configured as an implant, or the bone fixation system 20 can be configured to stabilize the first and second anatomical structures 22a and 22b relative to each other as described above, and further relative to a third anatomical structure, which can be bone or a bone implant. It should be appreciated, of course, that the bone fixation system 20 can be configured any number of anatomical structures relative to each other as desired. For instance, the fractured bone can be comminuted, and thus include any number of bone fragments that can be secured relative to each other by the bone fixation system 20. Otherwise stated, the bone fixation system 20 can be configured to be implanted onto bone so as to stabilize the bone with respect to one or more other anatomical structures.

The bone 24 is illustrated as a mandible in FIG. 1, though it should be appreciated that the bone can be defined by any suitable bone as desired in the human body, or other animal body, as desired, such as the pelvis, scapula, clavicle, wrist, spine, and the thorax region, including one or more ribs, the sternum, or the like. As is described in more detail below, the bone fixation linkage 26 is modular, and includes a plurality of interconnected links 32, at least two of which can be pivotally connected to each other and thus configured to be attached to each other so as to angulate with respect to each other about at least one axis. Accordingly, the bone fixation linkage 26 is configured to conform to the outer contour of the first and second anatomical structures 22a and 22b to which the bone fixation linkage 26 is secured. The bone fixation linkage 26 can be made from any suitable biocompatible material, including a metal such as titanium, stainless steel, or alloys thereof, or any suitable alternative implantable material, such as polymers based materials like polyether-ether-ketone (PEEK), or PEKK as desired.

Referring now to FIGS. 2A-3B, the bone fixation linkage 26, and thus each of the links 32, can define a bottom end or first end 34a, which can define a first surface, that is configured to face the underlying anatomical structure, such as the bone 24, and a top end or second end 34b, which can define a second surface, that is opposite the first end 34a. The first end 34a can be said to be spaced from the second end 34b along an inward direction. Similarly, the second end 34b can be said to be spaced from the first end 34a along an outward direction. Both the inward direction and the outward direction. Each of the first and second ends 34a and 34b can be sized and shaped as desired, and can define any number of surfaces as desired, including at least one or more surfaces. Each link 32 can include at least a first attachment member 36a and a second attachment member 36b that are configured to attach to each other such that one of the first and second attachment members 36a-b of a first one of the links 32 is attached to, for instance captured by, a complementary one of the first and second attachment members 36a-b of a second one of the links 32 so as to define an articulating joint. Thus, the first and second links 32 can angulate with respect to each other about at least one axis. The bone fixation linkage 26 can include any number of links 32 as desired depending on at least one of several factors, including on the desired length of the bone fixation linkage 26, the desired maneuverability of the bone fixation linkage 26, and the desired geometrical shape of the bone fixation linkage 26. In this regard, it should be appreciated that the links 32 can be attached to each other in any manner as desired such that the bone fixation linkage 26 defines any size and shape so as to conform to the underlying anatomy of the underlying bone, which can be any suitable bone as desired, for instance one or more bones of the hand or the distal radius, among others. Further, it should be appreciated that the bone fixation linkage 26 can be configured to join two different types of bone plates. For instance, the bone fixation linkage 26 can connect to a hand bone plate at one end, and to a distal radius bone plate at another end. In accordance with one embodiment, the outermost links 32 of the bone fixation linkage 26 can define outermost insertion members that are configured to be inserted into respective bone screw holes of the first and second bone plates, which can thus define receptacle members, in accordance with any embodiment described herein with respect to insertion and securement of the insertion members 40 into the receptacle members 42. Thus, the hand plate and the distal radius plate can be referred to as links that are configured to attach to the links 32 in the manner described herein. Further, it should be appreciated that the links 32 of the bone fixation linkage 26 can be substantially identical to each other, or one or more up to all of the links 32 can be constructed in accordance with alternative embodiments with respect to one or more other ones of the links 32, as is described in more detail below.

In accordance with one embodiment, each link 32 can include a neck 38 that extends between the pair of attachment members 36a-b, for instance from the first attachment member 36a to the second attachment member 36b, and is monolithic with the first and second attachment members 36. Either or both of the attachment members 36a-b of one or more up to all of the links 32 can be configured as an insertion member 40, and either or both of the attachment members 36a-b of one or more up to all of the links 32 can be configured as a receptacle member 42 that is configured to capture the insertion member 40 so as to define the articulating joint. For instance, the link 32 illustrated in FIGS. 3A-3B includes an insertion member 40 and a receptacle member 42. It should be appreciated unless otherwise indicated, that reference throughout this disclosure to first and second links 32 is intended to refer to the first link 32 whose insertion member 40 is configured to be received, or is in fact received, by the receptacle member 42 of the second link 32 to define an articulating joint. Thus, each link 32 of the type illustrated in FIGS. 3A-B can define both a first link and a second link, depending on the particular joint being referenced.

Figure 16B:
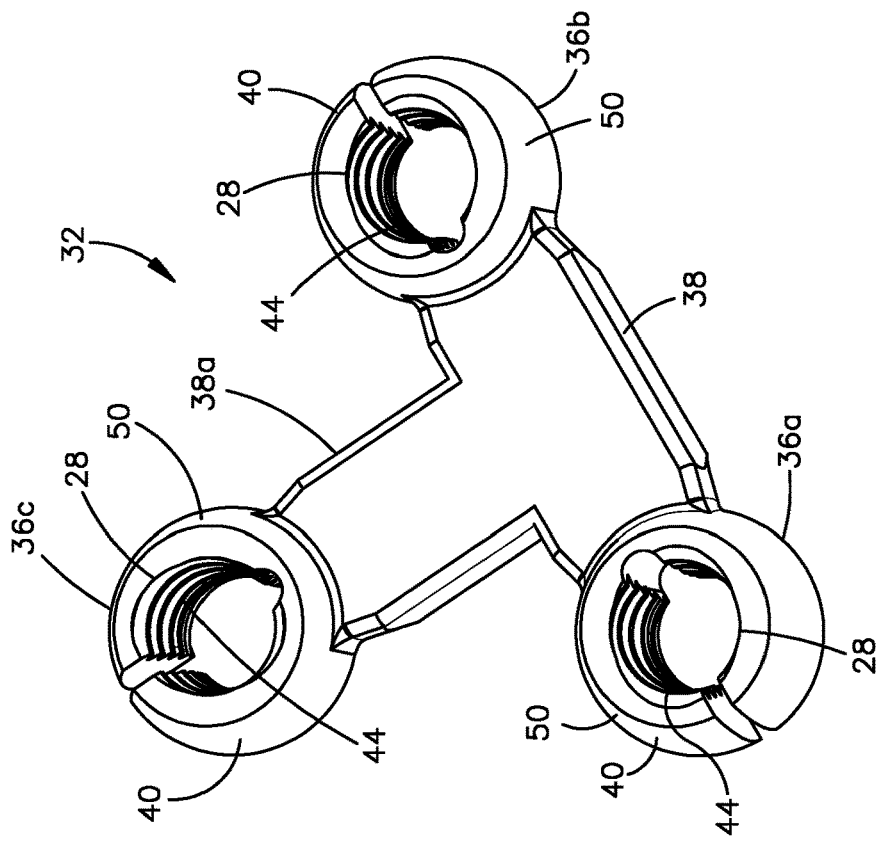
FIG. 16B is a perspective view of a link similar to FIG. 16A, but showing the multiple attachment members in accordance with another embodiment.
Figure 16A:
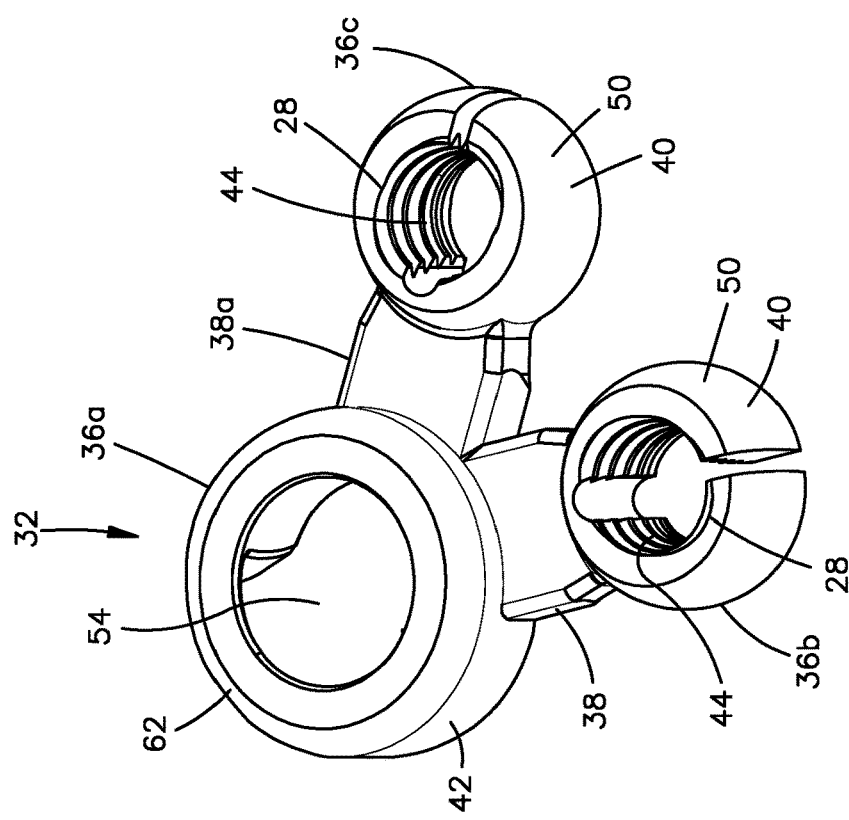
FIG. 16A is a perspective view of a link similar to FIG. 3A, but including an auxiliary attachment member in accordance with another embodiment.
Figure 16C:
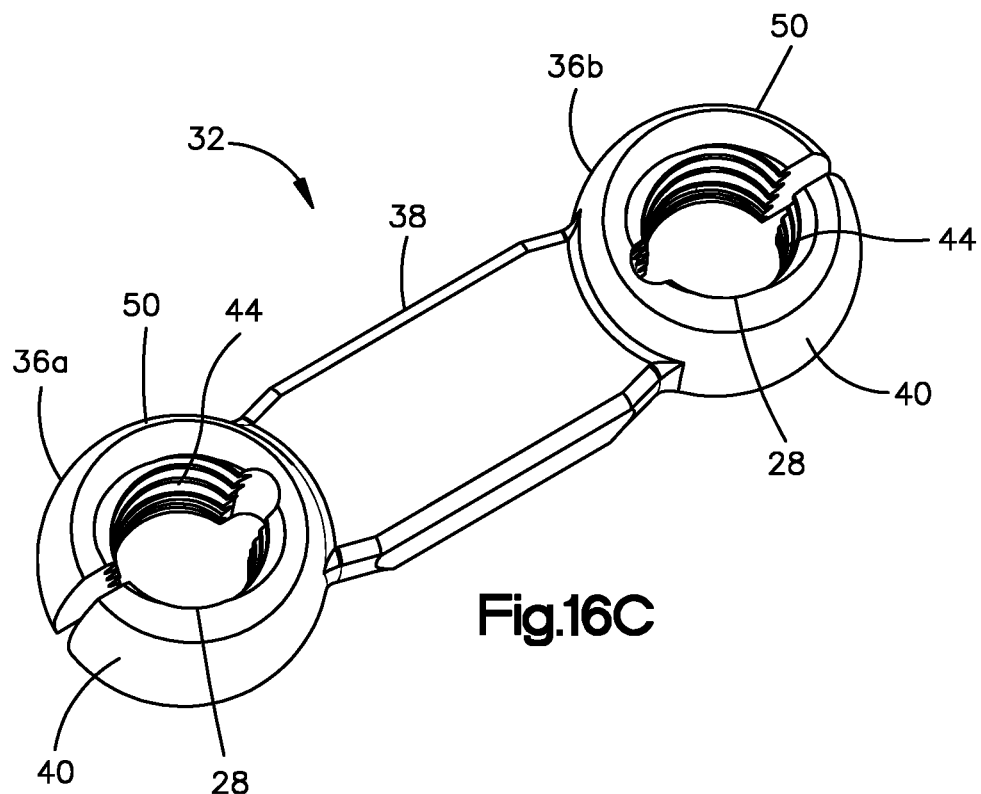
FIG. 16C is a perspective view of a link similar to FIG. 3A, but including a pair of insertion members in accordance with another embodiment.
Figure 16D:
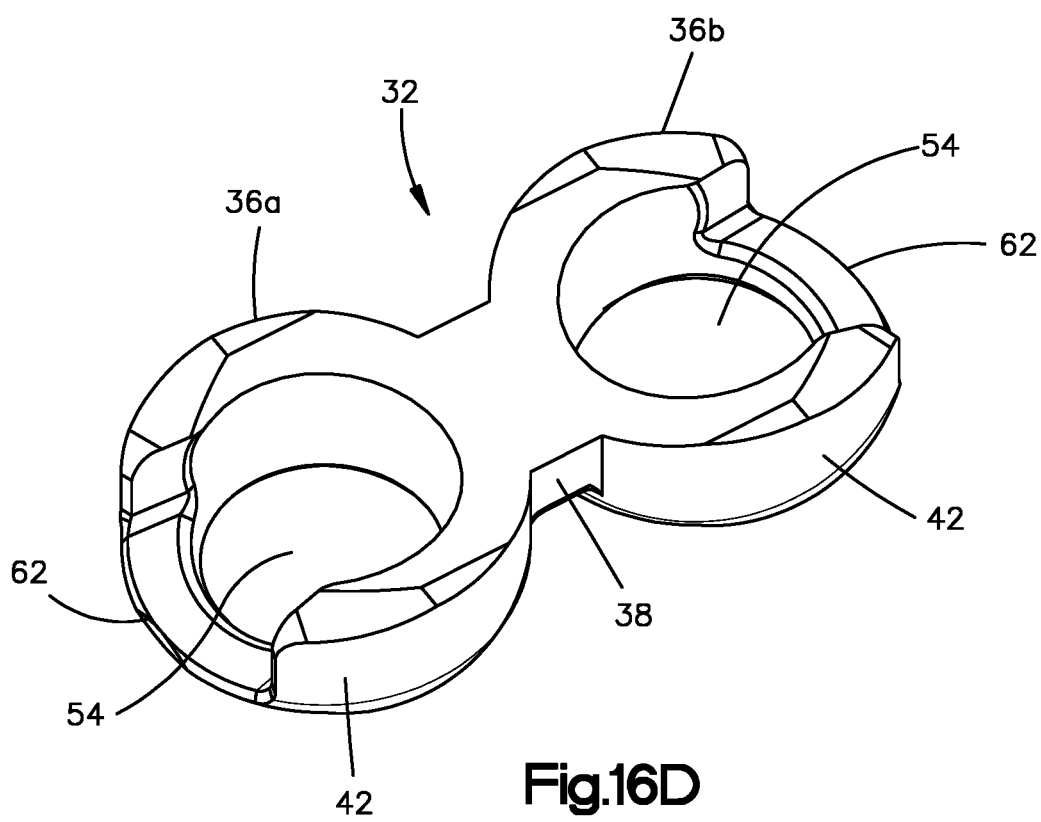
FIG. 16D is a perspective view of a link similar to FIG. 3A, but including a pair of receptacle members in accordance with another embodiment.

The attachment members 36a-b of the link 32 illustrated in FIG. 16C are each configured as an insertion member 40, and the attachment members 36a-b of the link 32 illustrated in FIG. 16D are each configured as a receptacle member 42. Further, one or more of the links 32 can include more than two attachment members, as illustrated in FIGS. 16A-B. The insertion members 40 and receptacle members 42 can be configured such that the insertion member 40 of a first one of the links 32 is configured to be inserted into and received by, and captured in, the receptacle member 42 of a second one of the links 32 such that the first and second links 32 are angulatable with respect to each other about at least one axis.

Figure 3A:
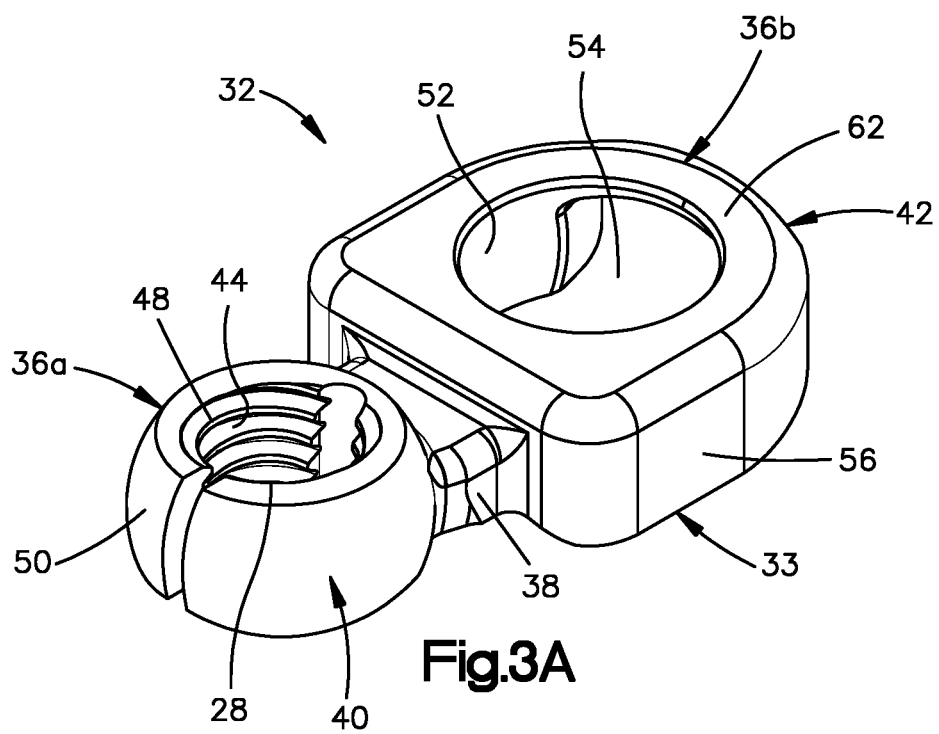
FIG. 3A is a perspective view of one of the links illustrated in FIG. 2A, the link including an insertion member and a receptacle member.
Figure 3B:
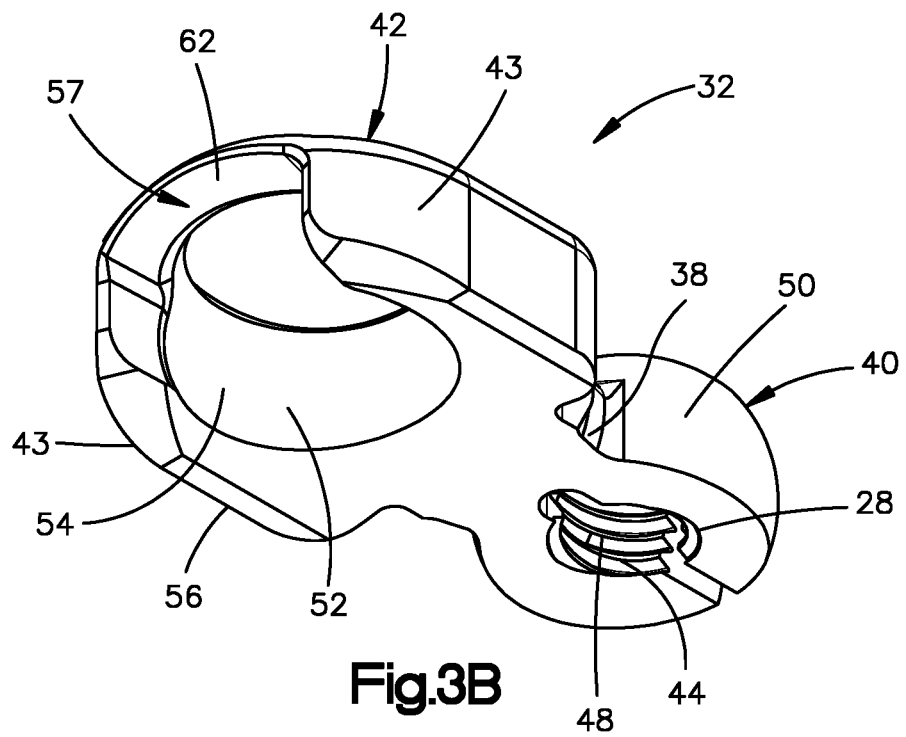
FIG. 3B is another perspective view of the link illustrated in FIG. 3A.

Referring now to FIGS. 3A-3B in particular, each link 32 can include a monolithic link body 33 that includes the neck, and the attachment members 36, such as the insertion member 40 and the receptacle member 42. The insertion member 40 can include interior surface 44 that defines an opening, such as a fixation hole 28, that extends from the first end 34a to the second end 34b and is configured to receive respective ones of the bone anchors 30. The bone anchors 30 each include a shaft that can be threaded so as to threadedly purchase with the underlying anatomical structure, and a head that is coupled to the shaft. The interior surface 44 can include projections such as threads 48 that threadedly purchase with complementary threads of the head of the bone anchor 30, which can be configured as a locking screw, as the bone anchor 30 is driven through the fixation hole 28 and into the underlying anatomical structure. Alternatively, the interior surface 44 can be smooth, or include a smooth portion, that is configured such that the head of the bone anchor 30, which can be configured as a compression screw whereby the head is unthreaded, can abut the smooth interior surface 44, or the threaded interior surface 44, and compress the respective link 32 against the underlying anatomical structure as the bone anchor 30 is driven through the fixation hole 28 and into the underlying anatomical structure. The insertion member 40 further include an outer surface 50 that is opposite the interior surface 44, and is configured to angulate within the receptacle member 42. Alternatively still, a first portion of the interior surface 44 can be smooth and devoid of threads, and a second portion of the interior surface 44 can be threaded. For instance, the first portion of the interior surface 44 can be disposed adjacent the second end 34b, and the second portion of the interior surface 44 can be disposed adjacent the first end. At least part up to all of the interior surface 44 can be conical, cylindrical, or alternatively shaped as desired. The interior surface 44 is configured to receive a bone fixation member as described in U.S. Patent Publication Serial No. 2008/0140130, the disclosure of which is hereby incorporated by reference as if set forth in its entirety herein.

Referring now also to FIGS. 4A-4F, the receptacle member 42 includes an interior surface 52 and an outer surface 56 opposite the interior surface 52. The interior surface 52 defines a receptacle 54 sized and configured to receive at least a portion, such as substantially all, of the outer surface 50 of the insertion member 40. For instance, the interior surface 52 can be sized and configured to capture the outer surface 50 of the insertion member 40 when the insertion member 40 is received in the receptacle 54. The outer surface 50 of the insertion member 40 is configured to ride along the interior surface 52 of the receptacle 54 as the corresponding links 32 angulate with respect to each other.

The receptacle member 42 includes an outer surface 56 opposite the interior surface 52, such that the neck 38 can extend from the outer surface 50 of the insertion member 40 to the outer surface 56 of the receptacle member 42. The neck 38 can be straight or curved as desired. The attachment members 36, for instance the insertion member 40 and the receptacle member 42, can be spaced from each other along a first direction, which can be referred to as a longitudinal direction L. Each of the links 32 can be elongate along the longitudinal direction. Thus, the neck 38 can define a central axis that extends from the insertion member 40 to the receptacle member 42, and in particular extends perpendicularly through the central axes of the insertion member 40 and the receptacle member, along the first or longitudinal direction L. Further, the fixation hole 28 and the receptacle 54 of a given link can define respective central axes that are spaced from each other and aligned with each other along the first direction. The first and second ends 34a and 34b are spaced from each other along a second direction, which can be referred to as a transverse direction T that is substantially perpendicular to the longitudinal direction L. The link 32 can define opposed sides 58 that are spaced from each other along a third direction, which can be referred to as a lateral direction A that is substantially perpendicular to both the longitudinal direction L and the transverse direction T. The longitudinal direction L and the lateral direction A can define a plane, such that angulation of at least one or more up to all of the links 32 with respect to another one of the links 32, for instance an adjacent one of the links 32, within or along the plane can be referred to as in-plane angulation. Angulation of at least one or more up to all of the links 32 with respect to another one of the links 32, for instance an adjacent one of the links 32, along a direction that intersects the plane, and thus has a directional component in the second or transverse direction, can be referred to as out-of-plane angulation. Further, at least one or more up to all of the links 32 can angulate torsionally with respect to another one of the links 32, for instance an adjacent one of the links 32, about a longitudinal axis that extends along the longitudinal axis L. As will be described in more detail below, the links 32 can be configured to angulate with respect to each other in-plane, out-of-plane, torsionally, or a combination of two or more up to all thereof. In-plane angulation can cause the links 32 to move in a direction that is substantially parallel or tangential to the underlying anatomical structure. Out-of-plane angulation can cause the links 32 to move in a direction toward or away from the underlying anatomical structure.

The receptacle member 42 can further include at least one arm that defines at least a portion of the interior surface 52 and the outer surface 56, such that the neck of the first link 32 extends past the at least one arm. The at least one arm can be curved or otherwise shaped as desired. For instance, the receptacle member can define first and second arms 43, that each defines at least a portion of the interior surface 52 and the outer surface 56. The receptacle member 42 can include any number of arms 43 as desired. The arms 43 can be spaced from each other so as to define a channel 57 that separates the first and second arms 43 and extends from the respective second interior surface to a second outer surface that is opposite the second interior surface, such that the at least a portion of the neck 38 of the first link 32 extends through the channel 57 when the insertion member 40 of the first link 32 is captured by the receptacle member 42 of the second link 32. As will be described in more detail below, the channel 57 can be sized and positioned so as to define an angle at which the first direction of the link 32 extends with respect to the first direction of the second link 32. Further, the channel 57 can further be sized such that interference between the receptacle member 42 and the neck 38 of the first link 32 limits certain angular movements of the first and second links 32 with respect to each other.

With continuing reference to FIGS. 2A-4C, the insertion member 40 can be flexible so as to compress from a neutral, undeflected, shape to a deflected shape as it enters the receptacle 54, and return from the deflected shape to the neutral shape when disposed in the receptacle 54. For instance, in accordance with the illustrated embodiment, the interior surface 52 of the receptacle member 42 can be spherical in shape, that is, it can define a portion of a sphere, or can be alternatively shaped as desired. Thus, the interior surface 52 can define an interior diameter $D_I$. In one embodiment, the interior surface 52 defines a middle portion 52a disposed between the first and second ends 34a and 34b, for instance equidistantly from the first and second ends 34a and 34b, and the middle portion 52a is spaced from the central axis of the receptacle 54 a distance greater than each of respective distances that the interior surface 52 is spaced from the central axis at the first and second ends 34a and 34b.

Similarly, in accordance with the illustrated embodiment, an entirety of the outer surface 50 of the insertion member 40 can be spherical in shape, that is, it can define a portion of a sphere, when the insertion member is in the neutral shape, or can be alternatively shaped as desired. The outer surface 50 can define a maximum outer cross-sectional dimension, which can be an outer diameter $D_O$ when the insertion member is in the neutral shape. In one embodiment, the outer surface 50 defines a middle portion 50a disposed between the first and second ends 34a and 34b, for instance equidistantly from the first and second ends 34a and 34b, and the middle portion 50a is spaced from the central axis of the fixation hole 28 a distance greater than each of respective distances that the outer surface 50 is spaced from the central axis at the first and second ends 34a and 34b. The outer diameter $D_O$ can be substantially equal to the inner diameter $D_I$ of the receptacle member 42, such that the outer surface 50 contacts the interior surface 52 and can ride along the interior surface 52. For instance, the outer surface 50 can ride along the interior surface 52 when shaping the bone fixation linkage 26 to the underlying anatomical structure.

In accordance with one embodiment, the insertion member 40 can be inserted into the receptacle 54 by aligning the insertion member 40 with the receptacle 54 along the transverse direction T, and snap-fitting the insertion member 40 into the receptacle 54. Because the cross-sectional dimension at the middle portion 50a is greater than the cross-sectional dimension of the interior surface 52 at each of the first and second ends 34a and 34b, contact between the receptacle member 42 and the insertion member 40 can cause the insertion member 40 to deflect, for instance compress, until the outer surface 50 defines a non-spherical shape sized for insertion into the receptacle 54. For instance, the maximum cross-sectional dimension of the insertion member 40 can decrease to a length substantially equal to the cross-sectional dimension of the interior surface 52 of the receptacle member 42 at one of the first and second ends 34a and 34b as the middle portion of the insertion member enters the receptacle 54. The insertion member 40, and thus the outer surface 50, can return to the neutral shape once the outer surface 50 is disposed in the receptacle 54.

As shown in FIG. 4C, the insertion member 40 can define at least one arm that can be curved or otherwise shaped as desired. For instance, the at least one arm can be configured as first and second arms 45, or any number of spaced arms 45 as desired, that each defines a portion of the interior surface 44 and the outer surface 50. The arms 45 can be spaced from each other so as to define a slot 59 that separates the first and second arms 45 from each other and extends from the respective interior surface 44 to the respective outer surface 50, and further extends from the first end 34a to the second end 34b. The slot 59 can be positioned at any location as desired, such that the arms 45 can have unequal lengths. The arms 45 can be flexible and configured to flex from a normal position to a compressed position so as to decrease the width of the slot 59, thereby iterating the insertion member from the normal shape to the deflected shape, as the insertion member 40 is inserted into the receptacle 54. The arms 45 can be resilient and return from the compressed position to the normal position when the insertion member is inserted in the receptacle, thereby iterating the insertion member 40 from the deflected shape to the normal shape. The insertion member 40 can further define one or more relief recesses, such as a relief recess 60, that extends from the interior surface 44 of the insertion member 40 into the neck 38 of the insertion member 40. The recess 60 can be disposed circumferentially opposite the slot 59, and can define a hinge of the insertion member about which the arms 45 can flex. While the body of the insertion member 40 can be discontinuous about the circumference of the hole 28, for instance at the slot 59, so as to define the arms 45 that can flex as the insertion member 40 is inserted into the receptacle member 42, it should be appreciated that the body of the insertion member 40 can alternatively be continuous about the circumference of the hole 28. For instance, the insertion member 40 can be made of a flexible material having a material property that is sufficiently flexible such that the insertion member 40 flexes as the insertion member 40 is inserted into the receptacle member 42. For instance, the flexible material can be any suitable polymer or metal as desired. It should be further appreciated that the insertion member 40 can further define both the slot 59 and be made of the flexible material.

Alternatively or additionally, while the insertion member 40 is flexible and configured to compress in accordance with one embodiment, the receptacle member 42 can be flexible and configured to expand from a normal position to a flexed position in accordance with an alternative embodiment. For instance, the arms 43 can be flexible and can expand away from each other so as to increase the cross-sectional dimension of the receptacle 54 such that the receptacle 54 is sized to receive the insertion member 40. The arms 43 can be resilient such that, as the insertion member 40 is captured within the receptacle, the arms 43 can return to their normal position. Thus, during operation, at least one of the insertion member 40 and the receptacle member 42 can flex from a normal shape to a deflected shape as the insertion member 40 is inserted into the receptacle 54, and can return from the deflected shape to the normal shape when the insertion member 50 is captured within the receptacle 54.

While one or both of the insertion member 40 and the receptacle member 42 can deform or flex so as to insert the insertion member 40 into the receptacle member 42 as described above, the insertion member 40 can be inserted into the receptacle in accordance with other embodiments. For instance, referring to FIG. 4G, the first link 32 can be inserted into the second link 32 by placing the insertion member 40 in the receptacle member 42 in an insertion orientation. In the insertion orientation, the central axis of the insertion member 40 of the first axis is angularly offset, for instance substantially perpendicular, with respect to the central axis of the receptacle member 42 a sufficient amount such that the neck 38 of the first link 32 is dimensioned less than channel 57 between the first and second arms 43, for instance along the lateral direction as defined by the second link 32. Further, the neck 38 of the first link 32 can be aligned with one or both of the first and second arms 43 along the lateral direction as defined by the second link 32.

The first link 32 can then be torsionally angulated, relative to the second link, about its longitudinal axis that is perpendicular to and intersects each central axis of the respective first and second attachment members, thereby capturing the insertion member 40 in the receptacle member 42 and attaching the first link 32 to the second link 32, such that the outer surface 50 rides along the interior surface 52. The first link 32 can be detached from the second link by removed the insertion member 40 from the receptacle member 42. For instance, the first link 32 can be torsionally angulated about its longitudinal axis until it is oriented in the insertion orientation, and the insertion member 40 can be translated out of the receptacle member 42. In this regard, links 32 can be attached to adjacent links 32 and removed from adjacent links in situ, that is when at least a portion of the linkage 26 is disposed against or attached to the underlying anatomical structure in the manner described above.

It should be appreciated, in accordance with certain embodiments, that the outer surface 50 can be spaced from the interior surface 52 when the insertion member 40 is disposed in the receptacle member 52, such that the insertion member 40 is translatable in the receptacle 54. Thus, the first link 32 can translate with respect to the second link 34, for instance along the longitudinal direction, when the insertion member 40 and the receptacle member 42 are movable with respect to each other. For instance, as the insertion member 40 is inserted into the receptacle member 42, contact between the outer surface 50 and the interior surface 52 can cause at least one of the insertion member 40 and the receptacle member 42 to flex. As described above, the flexed at least one of the insertion member 40 and the receptacle member 42 can return to its neutral position. Alternatively, the flexed at least one of the insertion member 40 and the receptacle member 42 can return toward, but not to, the neutral position. Alternatively still, the flexed at least one of the insertion member 40 and the receptacle member 42 can flex and deform plastically and not return toward the neutral position. Thus, the outer surface 50 can be spaced from the interior surface 52 when the insertion member 40 is disposed within the receptacle member 42. In accordance with still another embodiment, the outer surface 50 of the insertion member 40 can be sized smaller than the interior surface 52 of the receptacle member 42, such that the insertion member 40 can be inserted into the receptacle member without causing the insertion member 40 to abut the receptacle member 42. Thus, again, the outer surface 50 can be spaced from the interior surface 52 when the insertion member 40 is disposed within the receptacle member 42.

Figure 4D:
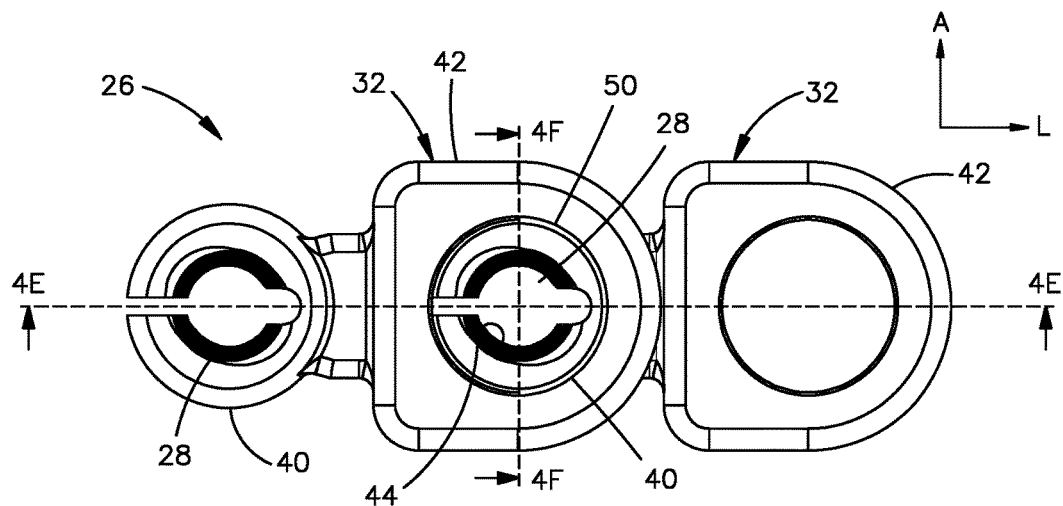
FIG. 4D is a top plan view of the first and second links illustrated in FIG. 4A.
Figure 4E:
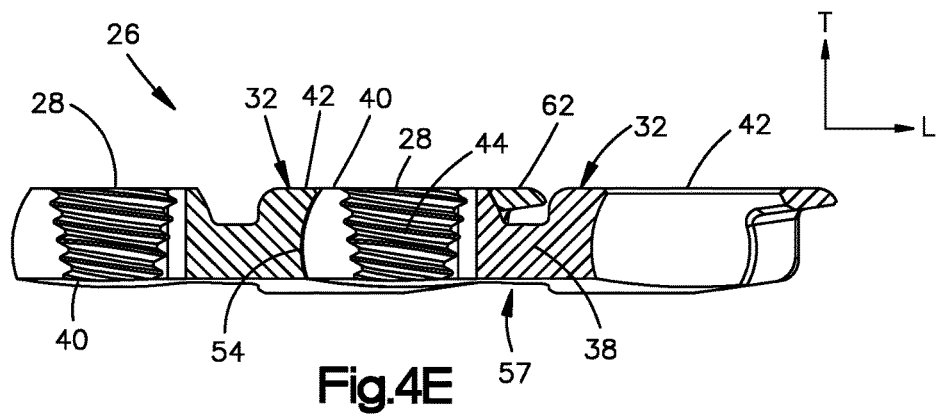
FIG. 4E is a sectional side elevation view of the first and second links illustrated in FIG. 4D, taken along line 4E-4E.
Figure 4F:
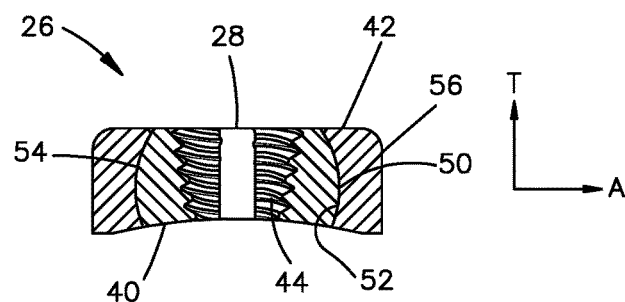
FIG. 4F is a sectional end elevation view of the first and second links illustrated in FIG. 4D, taken along line 4F-4F.
Figure 4G:
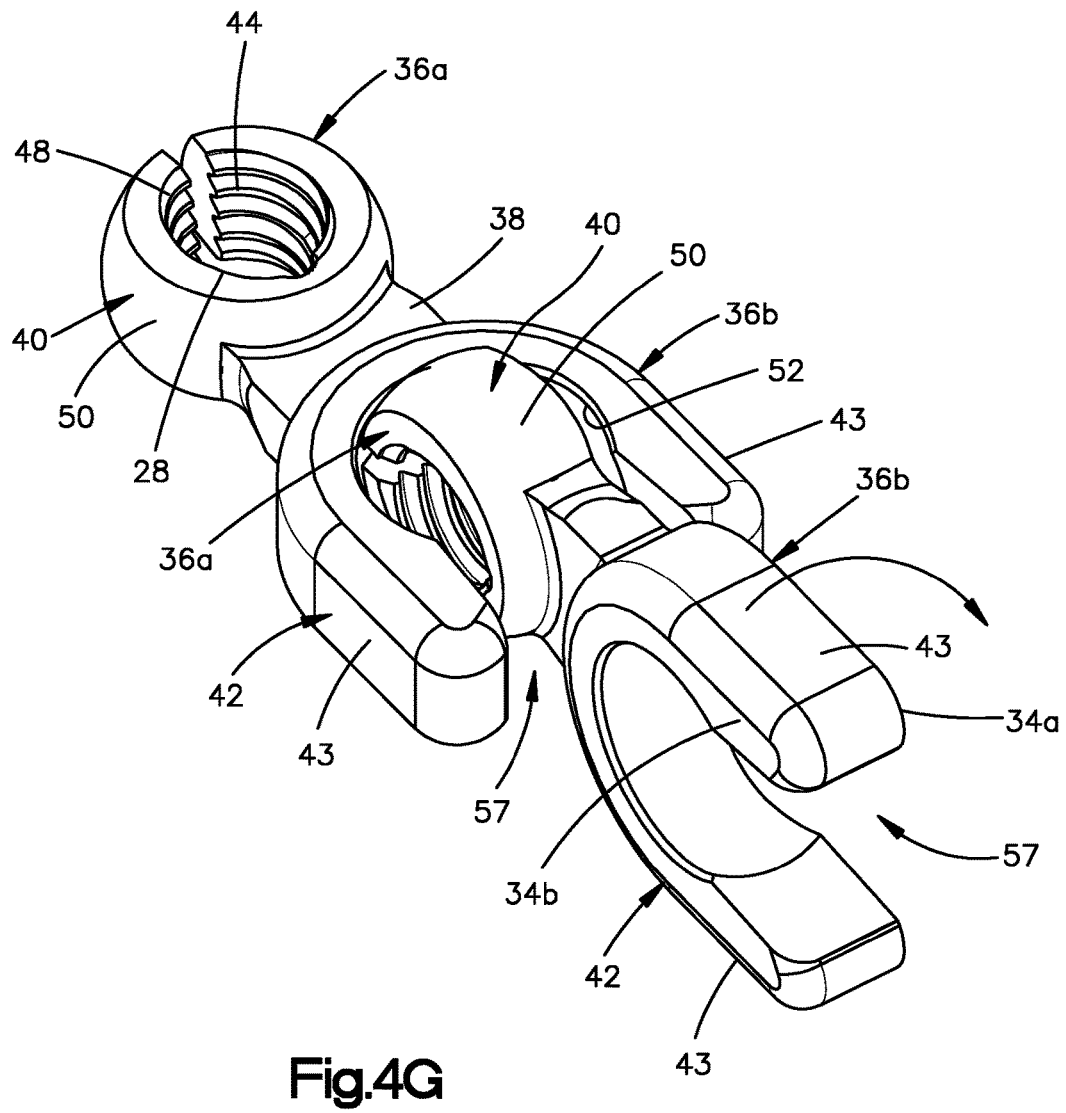
FIG. 4G is a perspective view showing insertion of the insertion member into the receptacle member in accordance with one embodiment.
Figure 5A:
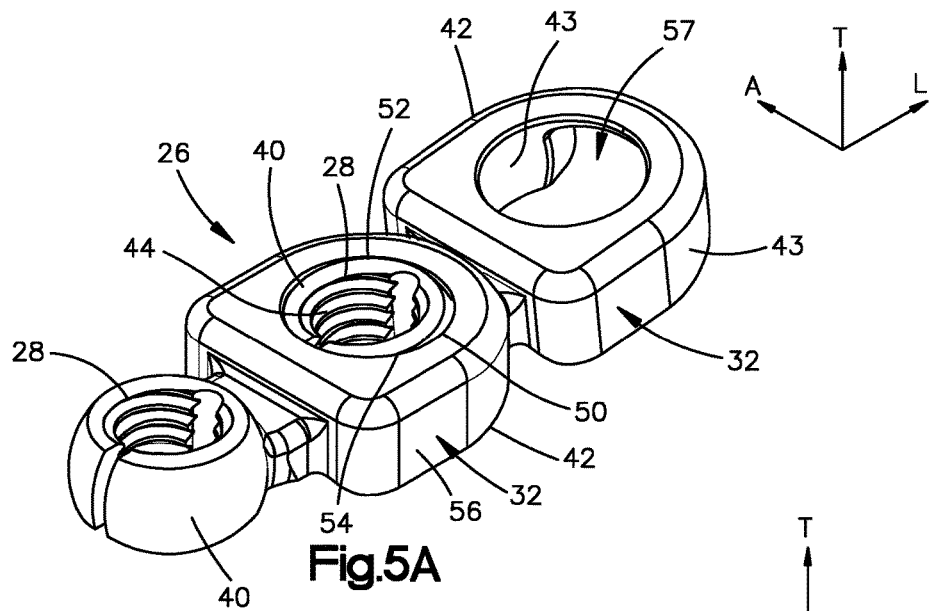
FIG. 5A is a perspective view of the linkage illustrated in FIG. 4A, shown in an angulated position about a lateral axis.
Figure 5B:
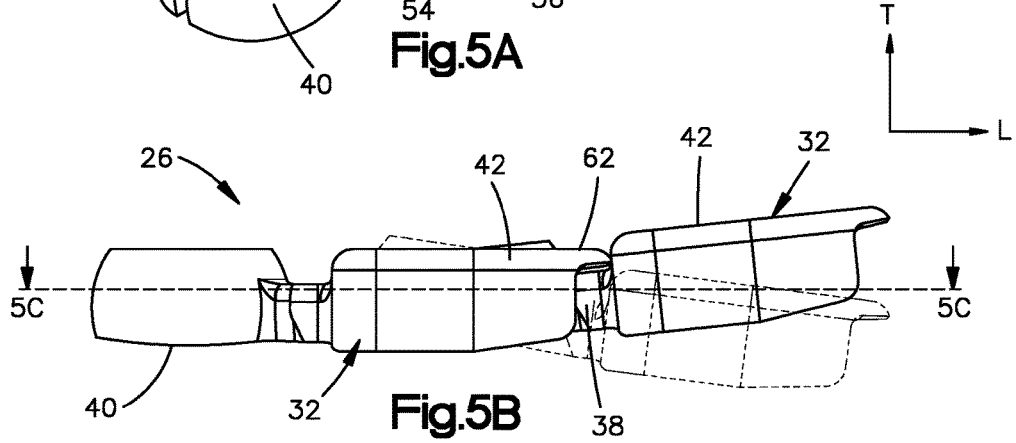
FIG. 5B is a side elevation view of the linkage illustrated in FIG. 5A.
Figure 5C:
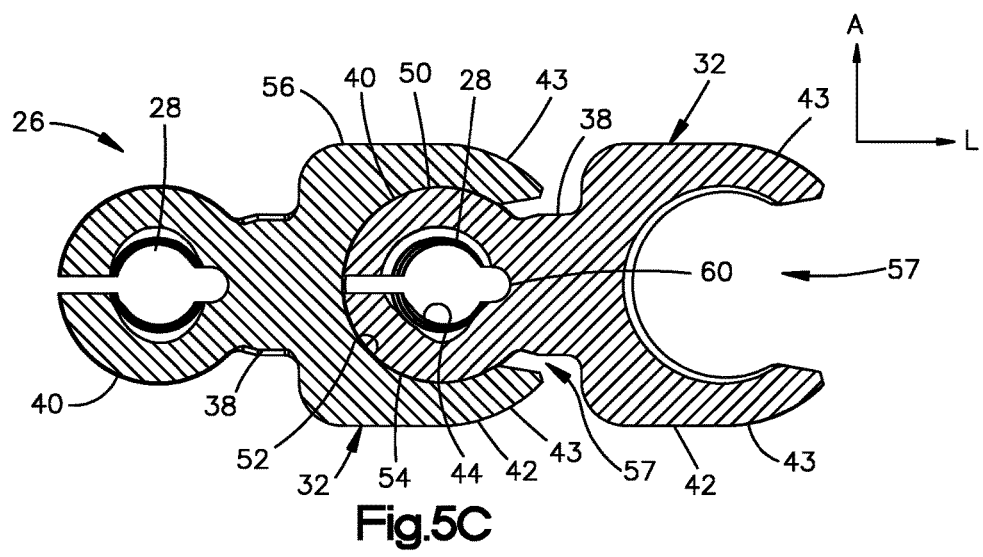
FIG. 5C is a sectional top plan view of the linkage illustrated in FIG. 5B, taken along line 5C-5C.
Figure 5D:
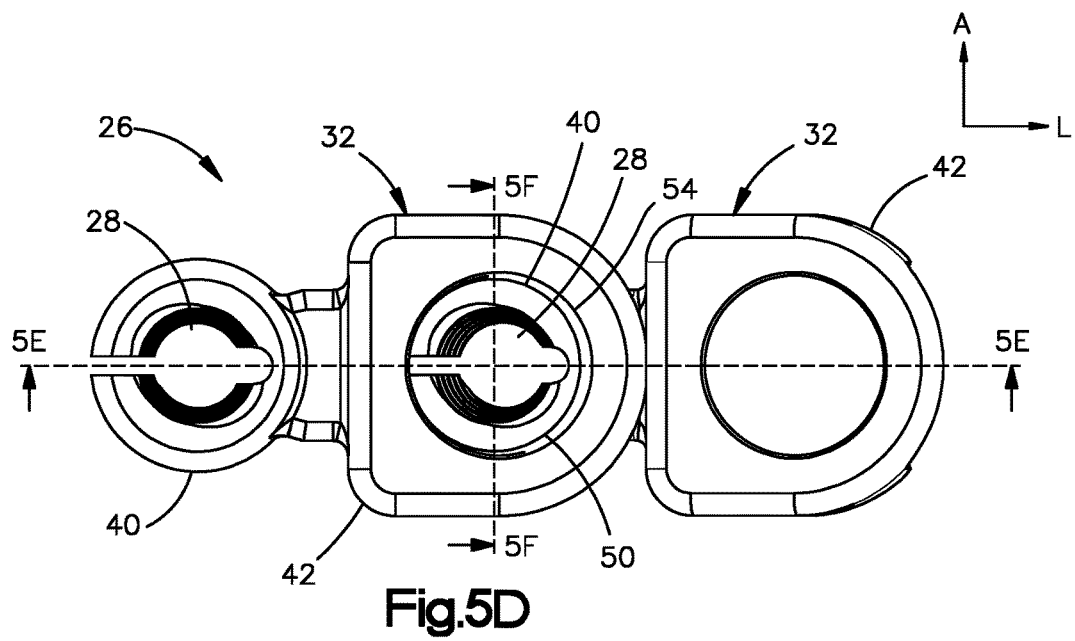
FIG. 5D is a top plan view of the linkage illustrated in FIG. 5A.
Figure 5E:
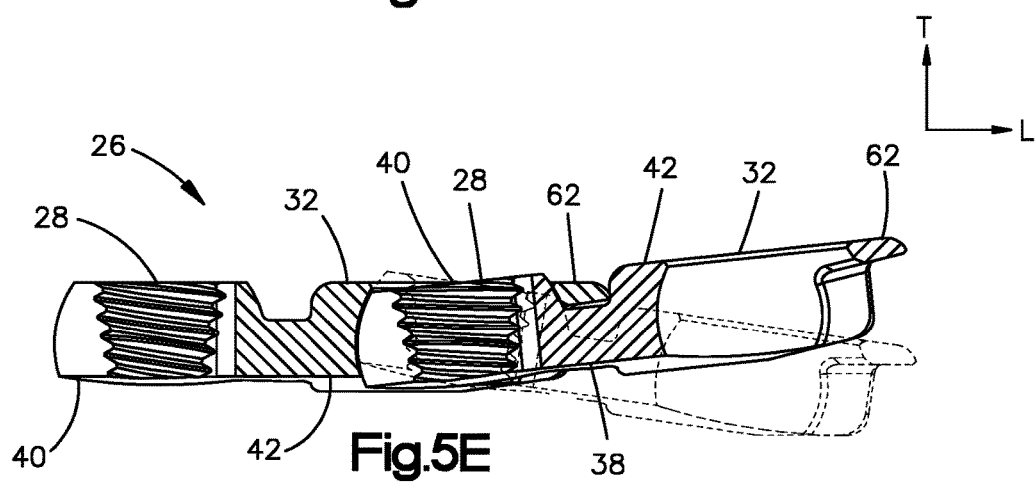
FIG. 5E is a sectional side elevation view of the linkage illustrated in FIG. 5D, taken along line 5E-5E.
Figure 5F:
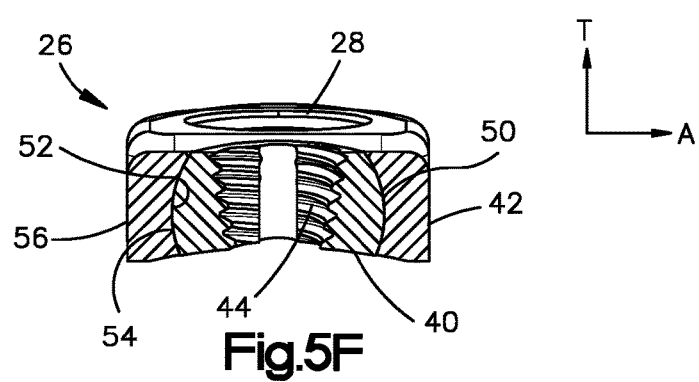
FIG. 5F is a sectional end elevation view of the linkage illustrated in FIG. 5D, taken along line 5F-5F.

Referring now to FIGS. 3A-3B and 4E, the receptacle member 42 can further include a bridge 62 that extends across the channel 57 from the first arm 43 to the second arm 43, such that the channel 57 extends from one of the first and second ends 34a and 34b to the bridge 62. The bridge 62 can define a portion of the interior surface 52 and a portion of the outer surface 56, and can thus partially define the receptacle 54. In accordance with one embodiment, the outer surface 56 can be convex at the bridge 62 along a plane defined by the lateral direction A and the longitudinal direction L. In accordance with the illustrated embodiment, the channel 57 extends from the first end 34a to the bridge 62. Further, the bridge 62 can be disposed at the second end 34b of the link 32. Accordingly, the insertion member 40 is configured to be inserted into the receptacle 54 along a direction from the first end 34a toward the second end 34b.

In accordance with an alternative embodiment, the bridge 62 can be disposed at or adjacent the first end 34a of the link 32, such that the bridge 62 is spaced from the second end 34b along the transverse direction T. Accordingly, the first link 32 can be attached to the second link 32 and removed from the second link in situ as described above with respect to FIG. 4G. At least a portion up to an entirety of the neck 38 of the second link 32 can be spaced from the first end 34a along the transverse direction T a distance at least substantially equal to the thickness of the bridge 62 along the transverse direction T, such that the bridge 62 of the second member does not mechanically interfere with the neck 38 of the first member when the insertion member 40 is disposed in the receptacle member 42 and the respective central axis are parallel with each other. The removed link 32 can be an outermost link or any link 32 of the linkage 26, for instance an inner link 32 whereby the linkage 26 includes links 32 disposed on both sides of the inner link 32 to be removed.

Referring now to FIGS. 5A-6F generally, and as described above, adjacent ones of the links 32 of the bone fixation linkage 26 are configured to angulate with respect to each other, and about each other, about at least one axis. This angulation of adjacent links 32 is illustrated and described herein with respect to the first and second links 32 as described above, though it should be appreciated that each link can be interconnected with one or more adjacent links. For instance, the links 32 illustrated in FIGS. 1-6F are configured to interconnect to a pair of adjacent links at the respective insertion members 40 and the receptacle members 42. It should be appreciated, however, as illustrated in FIGS. 16A-16B, that the links 32 can include more than two attachment members, such as three attachment members, that can each be configured as an insertion members 40 or a receptacle member 42 and thus can be configured to attach to and interconnect with an adjacent link in the manner described herein. It should be appreciated that the one or more of the attachment members of one or more of the links 32 of the bone fixation linkage 26 can include any suitable alternatively constructed attachment member that can be configured to movably attach to an adjacent link or rigidly attach to an adjacent link as desired.

Referring to FIGS. 5A-F in particular, the first and second links 32 can be configured to receive a force that causes the outer surface 50 and the interior surface 52 to ride along each other such that each of the adjacent first and second links 32 can angulate out-of-plane with respect to the other of the first and second links 32 about a lateral axis that extends along the lateral direction A, and thus along a plane that is defined by the transverse direction T and the longitudinal direction L. Because the channel 57 is open to the first end of the receptacle member 42, each of the first and second link 32 can angulate with respect to the other of the first and second links 32 about the lateral axis along a direction from the second end 34b to the first end 34a, and thus toward the underlying anatomical structure, without either of the links 32 interfering with the other of the links 32. Conversely, because the receptacle member 42 can include the bridge 62 that is connected between the arms 43, the bridge is configured to contact the neck 38 of the first link 32 as the first link 32 angulates with respect to the second link 32 about the lateral axis along a direction from the first end 34a toward the second end 34b. Thus, the receptacle member 42, and in particular the bridge 62, can define a stop that limits angulation of the first link 32 with respect to the second link 32 about the lateral axis. It is envisioned that the curvature of outer surface the underlying anatomical structure is likely to be convex to a greater degree than it is concave, and thus it may be desirable to allow for more angulation about the lateral axis in the direction from the second end 34b toward the first end 34a than angulation about the lateral axis in the direction from the second end 34*b* toward the first end 34*a*, such that the first end 34*a* of the linkage 26 conforms to the surface of the underlying anatomical structure.

Referring now to FIGS. 6A-6D in particular, the links 32 can be configured to receive a force that causes the outer surface 50 and the interior surface 52 to ride along each other such that each of the adjacent first and second links 32 can angulate in-plane about a transverse axis that extends along the transverse direction T, and thus along a plane that is defined by the lateral direction A and the longitudinal direction L. The transverse axis can define the central axes of both the fixation hole 28 and the receptacle 54 when the links 32 are in a neutral un-angulated position. The channel 57 can define a width in the lateral direction A that is greater than the width of the neck 38 of the insertion member 40 at a location where the neck 38 is disposed in the channel 57. Thus, the first link 32 is configured to angulate about the transverse axis T until the neck 38 abuts the one of the arms 43 that defines the channel 57 when the neck 38 is aligned with the channel 57 with respect to a plane that is defined by the longitudinal direction L and the lateral direction A. It should be appreciated that the links 32 can be configured so as to angulate with respect to each other about an axis that extends along the lateral direction A a sufficient amount so as to bring the neck 32 out of alignment with the arms 43 with respect to the plane that is defined by the longitudinal direction L and the lateral direction A. As the links 32 angulate with respect to each other about the transverse axis and only the transverse axis, the transverse axis can continue to define the central axes of both the fixation hole 28 and the receptacle 54.

The channel 57 can define a width from the first arm 43 to the second arm 43 that is greater than the corresponding width of the neck 38 of the insertion member 40 at a location where the neck 38 is disposed in the channel 57. Thus, the first link 32 is configured to angulate about the transverse axis T until the neck 38 abuts the one of the arms 43 that defines the channel 57 when the neck 38 is aligned with the channel 57 with respect to a plane that is defined by the longitudinal direction L and the lateral direction A. As will be described in more detail below, the links 32 can be configured so as to angulate with respect to each other about an axis that extends along the lateral direction A a sufficient amount so as to bring the neck 32 out of alignment with the arms 43 with respect to the plane that is defined by the longitudinal direction L and the lateral direction A. As the links 32 angulate with respect to each other about the transverse axis and only the transverse axis, the transverse axis can continue to define the central axes of both the fixation hole 28 and the receptacle 54.

Figure 6D:
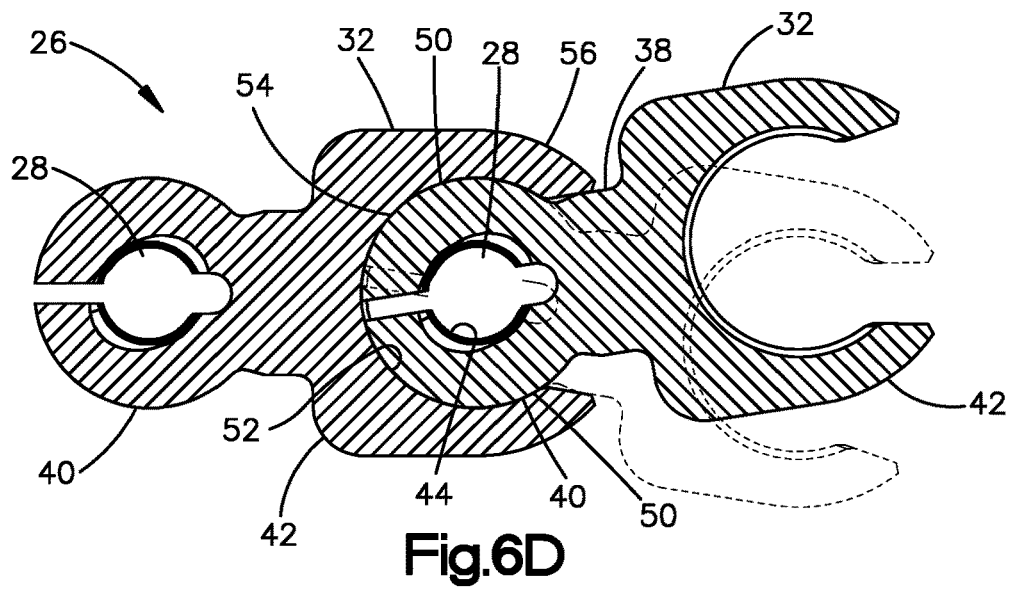
FIG. 6D is a sectional top plan view of the linkage illustrated in FIG. 6A.
Figure 6E:
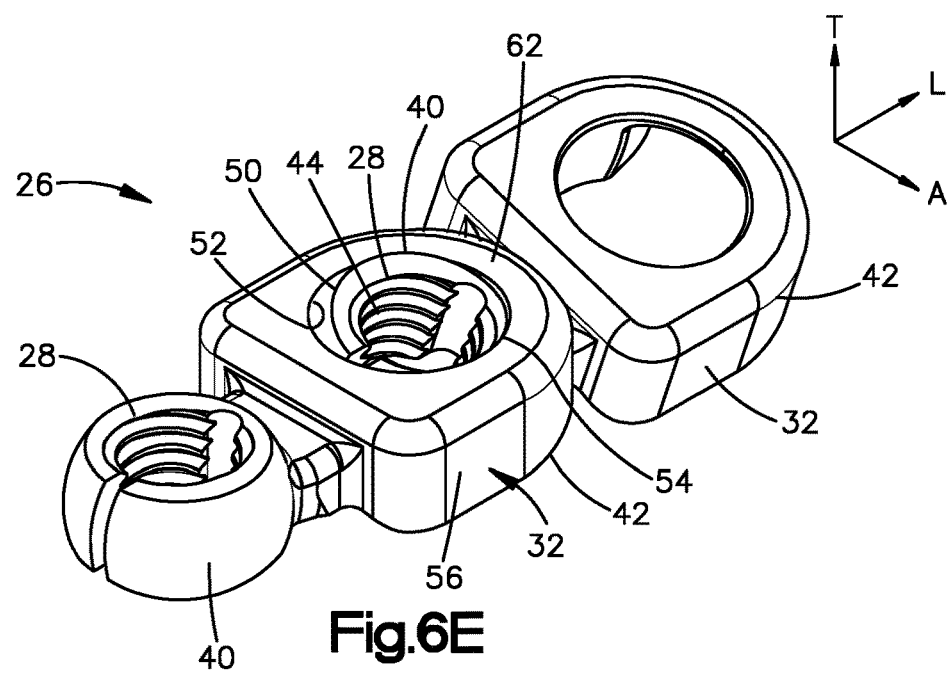
FIG. 6E is a perspective view of the linkage illustrated in FIG. 4A, shown angulated about a longitudinal axis.
Figure 6F:
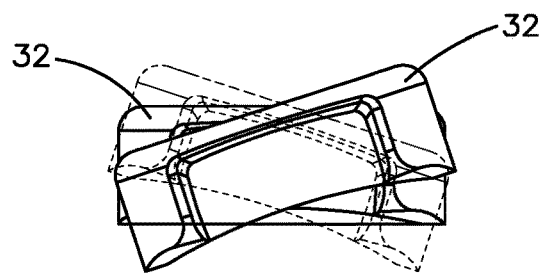
FIG. 6F is an end elevation view of the linkage illustrated in FIG. 6E.

Referring now to FIGS. 6E-6F, the links 32 can be configured to receive a force that causes the outer surface 50 and the interior surface 52 to ride along each other such that each of the adjacent first and second links 32 can angulate and pivot about a longitudinal axis that is perpendicular to and intersects each central axis of the respective first and second attachment members, which are defined by the respective insertion member 40 and the receptacle member 42 in accordance with one embodiment. The longitudinal axis can be defined by the central axis of the neck 38 in accordance with certain embodiments, for instance when the central axis of the neck 38 is perpendicular to and intersects the central axes of both the first and second attachment members (e.g., insertion member 40 and the receptacle member 42 in accordance with one embodiment). As will be described in more detail below, the longitudinal axis of the first link 32 can be inline with the longitudinal axis of the second link 32, or can extend along a direction that is angularly offset with respect to the longitudinal axis of the second link 32. Thus, it should be appreciated that the first and second links 32 can be configured to twist about each other along a direction that does not include the transverse direction T, and thus can twist about each other in-plane. The links 32 are configured to angulate about the longitudinal axis until the neck 38 of the first link 32 abuts the bridge 62, which can define a stop surface that abuts the first link 32 and limits angulation of the first and second links 32 with respect to each other about the longitudinal axis.

Thus, it will be appreciated that the first and second links 32 are configured to angulate with respect to each other about at least one axis. For instance, the first and second links 32 are configured to angulate with respect to each other about at least one axis that can be defined by a first axis that extends along a first one of the first direction (which can be defined by the longitudinal direction L), the second direction (which can be the transverse direction T), and the third direction (which can be the lateral direction A). Alternatively or additionally, the at least one axis can include a second axis that extends along a second one of the first, second, and third directions that is different than the first one. Alternatively or additionally still, the at least one axis can extend along a third axis that extends along a third one of the first, second, and third directions that is different than both the first and the second ones. Accordingly, the first and second links 32 are configured to angulate about each other along any one or more up to all of the first axis, the second axis, and the third axis, both alone and in combination. In accordance with one embodiment, the first and second links 32 are configured to angulate polyaxially with respect to each other about each of the first, second, and third axes. Furthermore, the first, second, and third directions can intersect each other at a common point or can intersect each other at different locations, for instance when the insertion member 40 is loosely received in the receptacle 54. The common point can be located at the centroid of the spherical shapes that define the outer surface 50 and the interior surface 52, when the outer surface 50 and the interior surface 52 are spherical. It can thus be said that the first and second links 32 are configured to angulate with respect to each other from a neutral position to an angulated position. When in the neutral position, the longitudinal, lateral, and transverse axes of the insertion member 40 of the first link 32 can coincide with the longitudinal, lateral, and transverse axes of the second link 32.

In accordance with one embodiment, at least one or more up to all of the links 32 can define a select link having a first attachment member that is configured to attach to an attachment member of a first adjacent link, and a second attachment member that is configured to attach to a second adjacent link. For instance, the first attachment member can be shaped so as to allow the select link to angulate with respect to the first adjacent link about at least one axis, and the second attachment member can be shaped so as to allow the select link to angulate with respect to the second adjacent link about a greater or fewer number of axes than the first attachment member. For instance, the first attachment member the first attachment member can be shaped so as to allow the select link to angulate with respect to the first adjacent link about one axis, and the second attachment member can be shaped so as to allow the select link to angulate with respect to the second adjacent link about at more than axis, such as two axes or three axes as desired. Furthermore, the select link 32 can be configured to translate with respect to one or both of the first and second adjacent links as desired.

Referring now to FIGS. 1-6F general, during operation, the links 32 of the bone fixation linkage can 26 be positioned against or adjacent the underlying anatomical structure such that at least one of the links 32 is disposed against or adjacent the first anatomical structure 22a, such as a first bone fragment, and at least another one of the links 32 is disposed against or adjacent the second anatomical structure. As the links 32 are brought against the outer surface of the underlying anatomical structures 22a and 22b, the contour of the respective anatomical structures 22a and 22b can cause one or both of the links 32 to angulate with respect to the other about at least one axis, such that the first end 34a of each of the links 32 abuts the underlying anatomical structure or is spaced from and oriented substantially parallel with (and thus operationally aligned with) the underlying anatomical structure.

The links 32 can further receive a force that causes at least one of the links 32 to angulate in-plane with respect to an adjacent one of the links 32 about an axis that extends in the transverse direction T. Thus the links 32 can be positioned over a desired portion of the underlying anatomical structure to which the links 32 are to be secured.

It should be appreciated in accordance with one embodiment that the insertion member 40 and the receptacle member 42 can define a frictional force at an interface between the outer surface 50 and the interior surface 52. The frictional force can be configured to provide a resistance to angulation of the first and second links 32 relative to each other. The resistance can be overcome by an applied force that causes at least one or both of the first and second links 32 to angulate with respect to each other so as to conform the bone fixation linkage 26 to the outer surface of the underlying anatomical structure.

Whether the outer surface 50 and the interior surface 52 ride along each other or are spaced from each other, a fastener is configured to lock the outer surface 50 against the inner surface with respect to relative movement. For instance, the fastener can be configured as a fixation member having a head that is brought into contact with the interior surface 44 of the insertion member 40. The head of the fixation member, which can be conical for instance, can apply a radially outward force against the insertion member body that biases the insertion member body radially outward against the interior surface 52 of the receptacle member 42, thereby biasing the insertion member body to bear, for instance compress, against the interior surface 52, which locks the first and second links 32 with respect to angulation relative to each other. It should be appreciated that the fixation member can lock the outer surface 50 against the interior surface 52 whether the outer surface 50 is spaced from the interior surface 52 or rides along the interior surface 52. Accordingly, normal anatomical forces will be insufficient to cause the first and second links 32 to angulate with respect to each other after the bone fixation linkage has been secured to the underlying first and second anatomical structures 22a and 22b.

It should be appreciated that the fixation member can cause the outer surface 50 to bear against the interior surface 52 directly or indirectly via an intermediate member that is disposed between the outer surface 50 and the interior surface 52. For instance, the linkage 26 can include an intermediate member, such as a collet, that can be disposed between the outer surface 50 and the interior surface 52. The collet can have a body and a plurality of spaced fingers that extend from the body. Accordingly, as the fixation member is driven into the respective fixation hole, the fixation member can drive the collet toward the first end 34a, thereby driving the fingers between the outer surface 50 and the inner surface so as to create a friction fit that prevents the insertion member 40 from angulating within the receptacle member. Collets of this type are described in U.S. Pat. No. 8,221,472, the disclosure of which is hereby incorporated by reference as if set for in its entirety herein.

One or more of the fixation members can be configured as a bone anchor 30 whose shaft is sized to extend beyond the first surface 34a when the head is disposed in the opening of the insertion member 40. Thus, the head of the bone anchor 30 can be driven into the opening of the insertion member 40 such that the shaft of the bone anchor 30 is driven, for instance threadedly driven, into the underlying anatomical structure and tightened against the interior surface 44, thereby securing the respective links 32 to the underlying anatomical structure in the manner described above. Alternatively, the bone anchors 30 can be driven, for instance threadedly driven, into underlying bone. Prior to tightening the head of the bone anchor against the interior surface 44, one or more of the links 32 can be angulated with respect to one or more others of the links 32 about the at least one axis, thereby repositioning a first respective underlying bone segment with respect to a second respective underlying bone segment so as to align the first and second bone segments with each other. In accordance with one embodiment, as described herein (see FIGS. 6I-6J), the first and second links 32 can be translated with respect to each other so as to reduce the bone gap G (see FIG. 1) and approximate the first and second bone segments. The heads of the respective fixation members can then be tightened against the outer surface 50 so as to compress the outer surface 50 against the interior surface 52, thereby fixing the insertion member 40 and the receptacle 42 with respect to movement relative to each other in the manner described herein.

In accordance with one embodiment, one or more of the fixation members can be configured as a set screw whose shaft is sized to terminate between the first and second surfaces 34a or terminate at a location flush with the first surface 34a, and thus does not extend out from the first surface 34a, when the head is disposed in the opening of the insertion member 40.

Figure 6G:
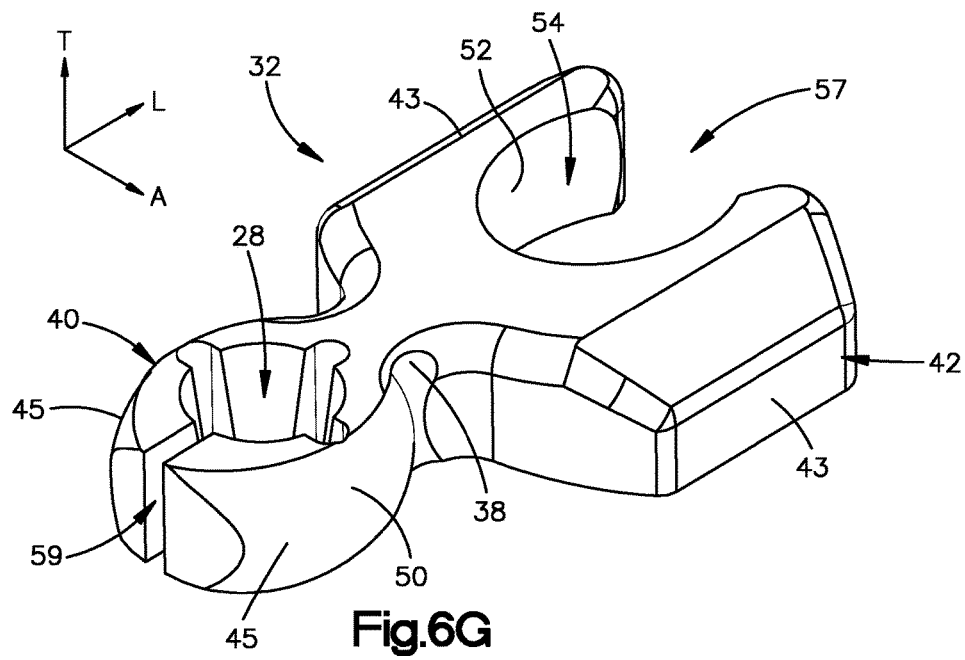
FIG. 6G is a perspective view of a link including an insertion member constructed in accordance with another embodiment.
Figure 6H:
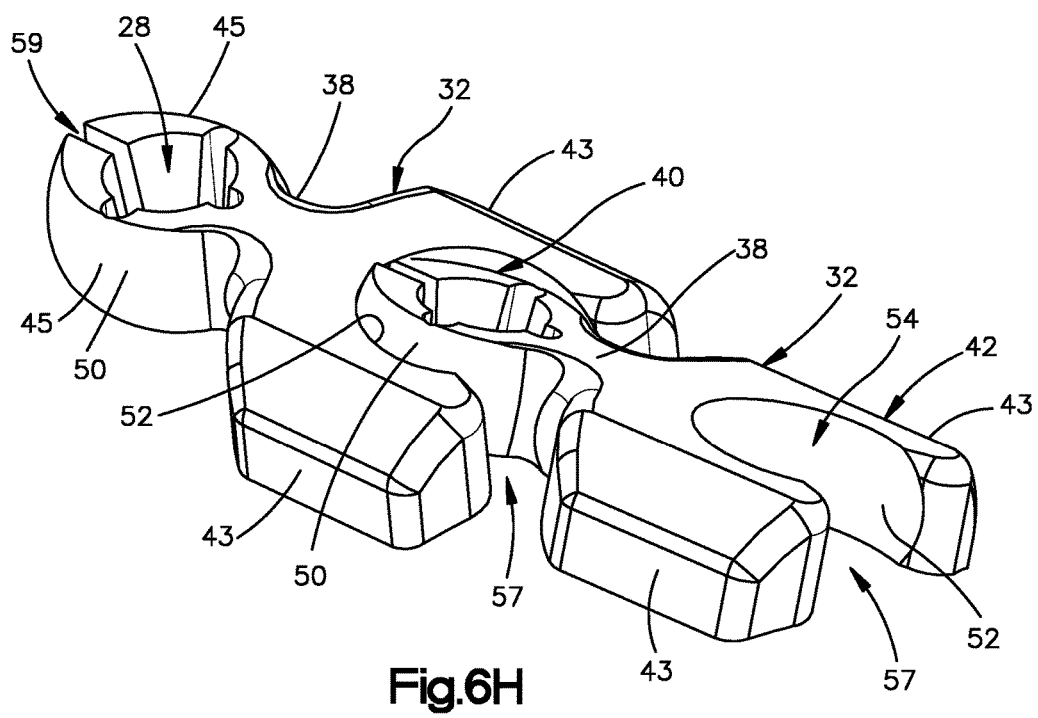
FIG. 6H is a perspective view of a linkage including the insertion member illustrated in FIG. 6G inserted into a receptacle member of another linkage.
Figure 6I:
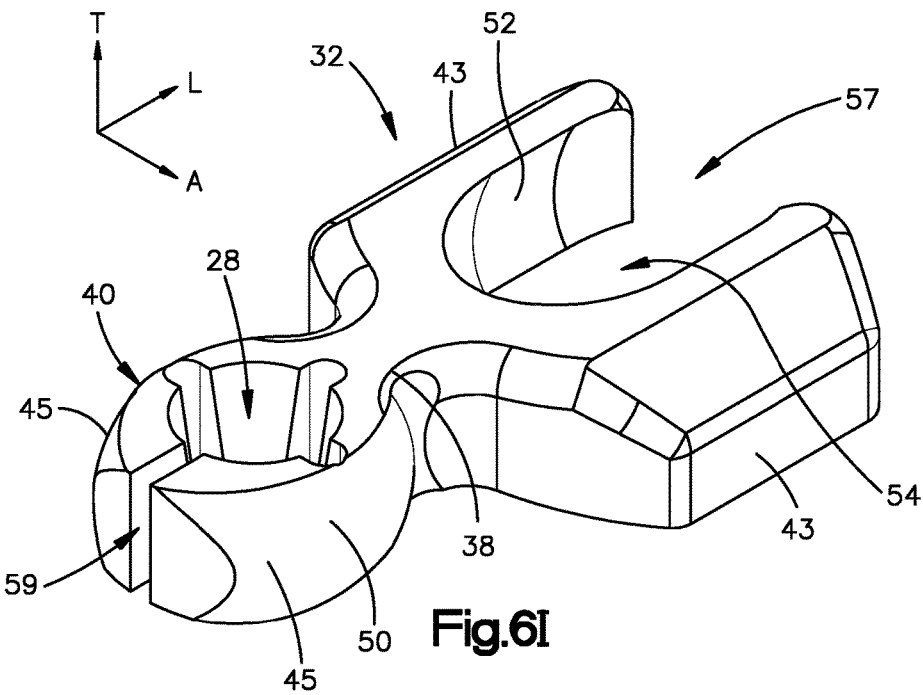
FIG. 6I is a perspective view of a link constructed in accordance with another embodiment.
Figure 6J:
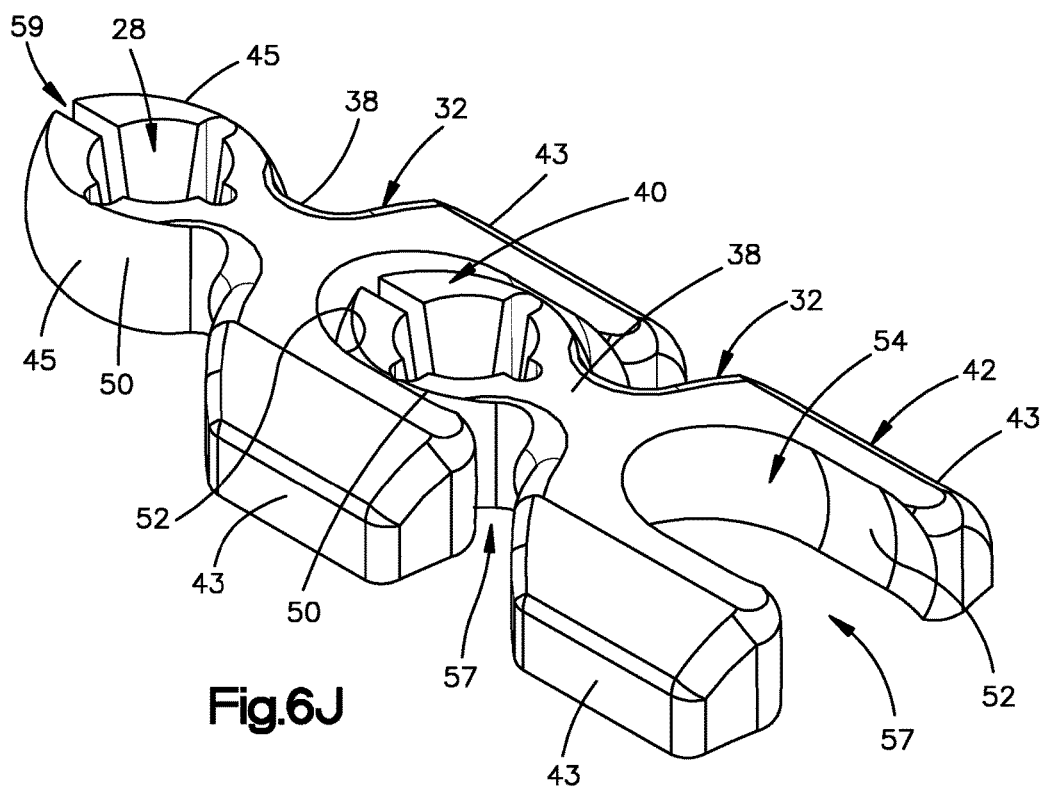
FIG. 6J is a perspective view of the link illustrated in FIG. 6I shown attached to another linkage.
Figure 6K:
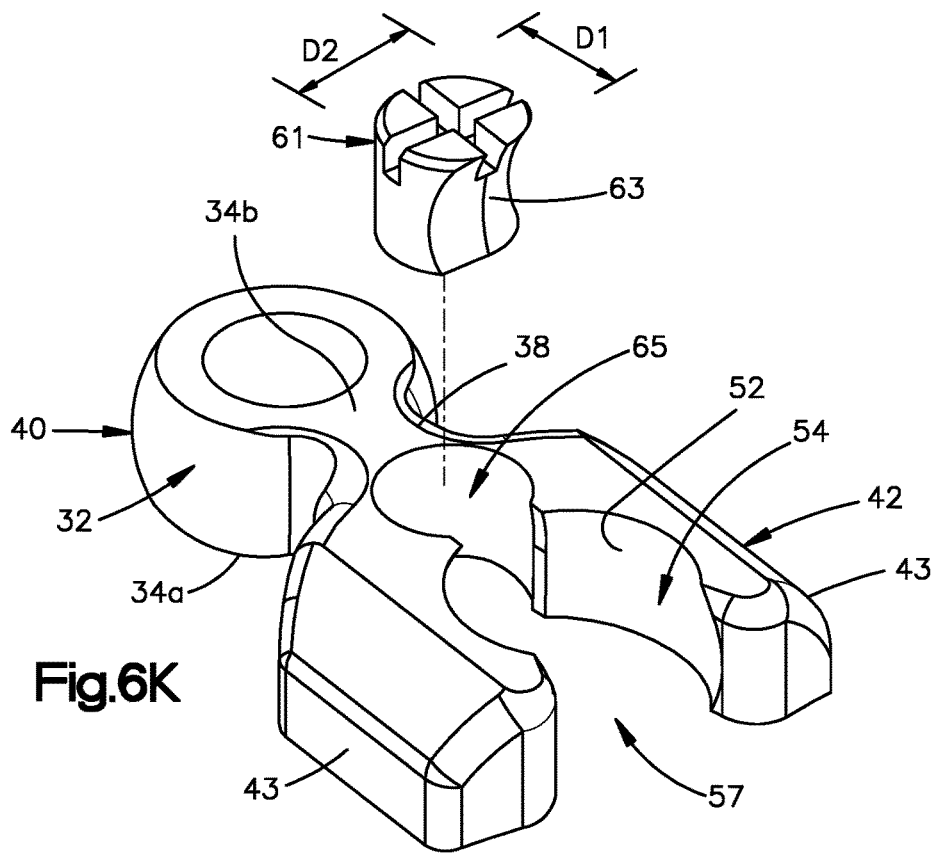
FIG. 6K is an exploded perspective view of a link constructed in accordance with alternative embodiment, including a cam member.
Figure 6L:
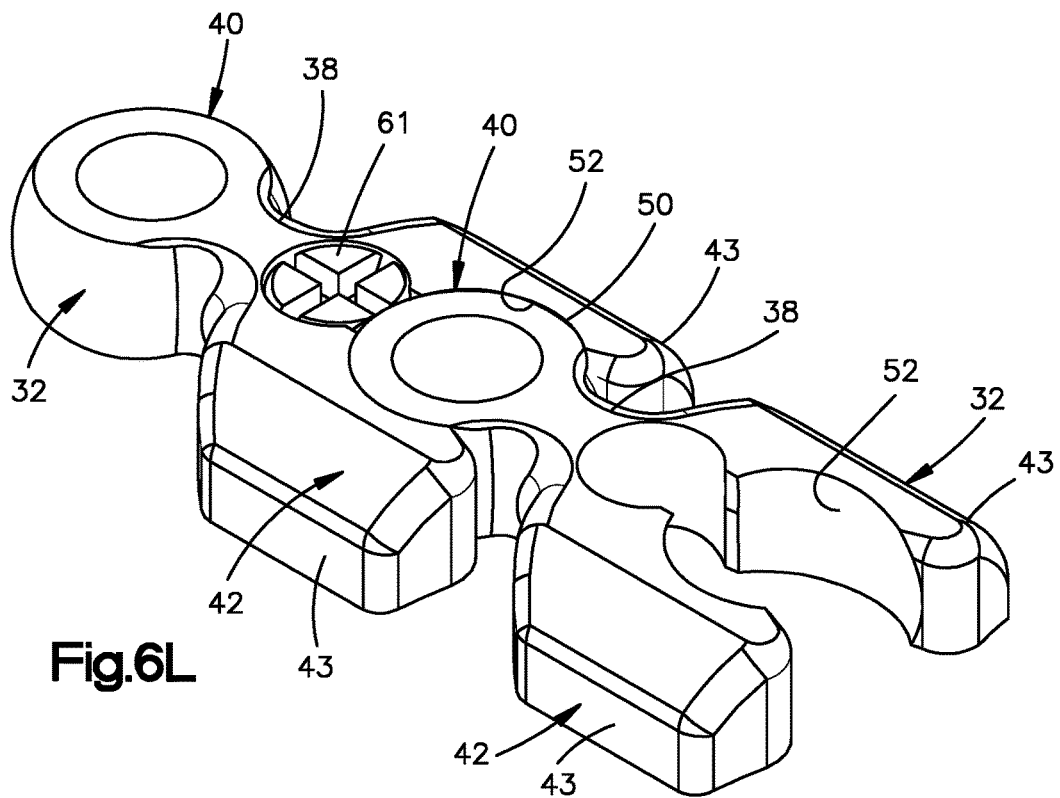
FIG. 6L is a perspective view of a linkage including the link illustrated in FIG. 6K, showing the cam member inserted into the link body adjacent the receptacle member, and a second link whose insertion member is shown inserted into the receptacle member

Referring now to FIGS. 6K-O, in should be appreciated that the insertion member 40 can be secured in the receptacle member 42 in accordance with any suitable alternative embodiment. For instance, while the fastener can be configured as a fixation member in accordance with one embodiment described above, the fastener can be alternatively configured as desired so as to bias the outer surface 50 of the insertion member 40 against the interior surface 42 of the receptacle member 42. Referring in particular to FIGS. 6K-6M, the fastener can be configured as a cam member 61 having an outer cam surface 63 that is configured to bear against the outer surface 50. In particular, the second link 32 can define a fixation aperture 65 that can extend from the second end 34b toward the first end 34a, and can extend through to the first end 34a. The fixation aperture 65 can be in communication with the receptacle 54 such that the cam surface 63 can bear, directly or indirectly, against the outer surface 50 of the insertion member 40 of the first link 32 that is disposed in the receptacle 54 of the second link 32. In this regard, the fixation aperture 65 can be open to the receptacle 54 such that the cam surface 63 can directly abut the outer surface 50. Alternatively, an intermediate member, such as a divider wall can separate the fixation aperture 65 from the receptacle 54 such that the cam surface 63 abuts the intermediate member, which in turn abuts the outer surface 50. The cam surface 63 can be concave or otherwise shaped and sized so as to abut the outer surface 50 or the intermediate wall. The cam member 61 further defines a first region having a first cross-sectional dimension D1 along a first direction, and a second region having a cross-sectional dimension D2 along a second direction that is angularly offset, for instance substantially perpendicular, with respect to the first direction. The second dimension D2 is greater than the first dimension D1. Accordingly, as illustrated in FIGS. 6N and 6O, the cam member 61 is rotatable in the fixation aperture 65 from a first position, whereby the first region of the cam surface 63 faces the outer surface 50 of the insertion member 40 that is disposed in the receptacle 54, to a second position whereby the second region of the cam surface 63 faces the outer surface 50. When the cam member 61 is in the first position, the cam surface 63 does not bear against the outer surface 50 with sufficient force so as to prevent rotation of the insertion member 40 with respect to the receptacle member 42. Thus, the insertion member 40 can angulate with respect to the receptacle member 42 about the at least one axis. When the cam member 61 is in the second position, the cam surface 63 bears against the outer surface 50, and biases the outer surface 50 against the inner surface 62 so as to define a frictional force between the surfaces 50 and 52 that is sufficient to prevent the insertion member 40 from rotating within the receptacle member 42 in response to normal anatomical forces during operation. The interior surface 52 can be curved along the arms 43 so as to define a concavity that faces the receptacle 54, such that the outer surface 50 bears against the concavity. It should be appreciated that the cam surface 63 can be unthreaded or threaded as desired.

It should be appreciated that the user can elect not to drive the fixation member each of the fixation holes 28 or through a plurality of the fixation holes 28. For instance, if the bone fixation linkage 26 includes third and fourth links that are pivotally coupled to the first and second links 32, respectively, such that the first and second links 32 are disposed between the third and fourth links, the third link can be locked to the first link, and the fourth link can be locked to the second link, thereby preventing the first and second links 32 from angulating with respect to each other without directly locking the first link 32 to the second link 32. In accordance with one embodiment, one or more fixation holes 28 aligned with or disposed proximate to the bone gap G can be devoid of fixation members as desired. Alternatively or additionally, one or more of the fixation holes 28 can receive a bone fixation member, such as a bone screw, such that the bone screw extends into the underlying bone and the head is disposed in the fixation hole 28, but not tightened to the link 32 in the fixation hole a sufficient amount such that the insertion member 40 is unable to angulate within the receptacle member 42. Thus, the fixation member can be inserted into the fixation hole 28 and into the bone while allowing the insertion member 40, and the corresponding first link 32, to angulate with respect to the receptacle member 42, and the corresponding second link 32.

Because at least a portion up to all of both the outer surface 50 and the interior surface 52 can be spherical defined by substantially the same radius of curvature, the outer surface 50 and the interior surface 52 can be in surface-to-surface contact. It should be appreciated, of course, that when angulation is desired about all three axes, a portion up to all of one of the outer surface 50 and the interior surface 52 can define a continuous spherical surface, and at least a portion up to all of the other of the outer surface and the interior surface 52 can define any shape as desired such that it contacts the continuous spherical surface at least at three discrete contact locations, such that the outer surface 50 is captured in the receptacle 54 by the interior surface 52. In this regard, it should be appreciated that the three discrete locations can define locations of point-on-surface contact, or surface-on-surface contact, and can be considered a spherical surface even though it is not a continuous spherical surface. Alternatively still, it should be appreciated that the shape of one or both of the outer surface 50 and the complementary interior surface 52 can be shaped other than spherical. For instance, one or both of the outer surface 50 and the interior surface 52 can be polygonal, defining respective regular or irregular polygons, or otherwise shaped as desired.

For instance, referring now to FIGS. 6G-6H, the outer surface 50 can be round but non-spherical. In accordance with one embodiment, the outer surface 50 can be substantially football-shaped, having a first dimension along a first direction such as the longitudinal direction L, and a second dimension along a second direction such as the lateral direction A. Thus, the first dimension can be angularly offset, for instance perpendicular, with respect to the second dimension. In accordance with one embodiment, the outer surface 50 can be oval-shaped. Thus, the outer surface 50 can define a first curvature as it extends along the longitudinal direction L, and a second curvature as it extends along the transverse direction T, wherein the first curvature is less than the second curvature. The interior surface 52 can have a curvature along the longitudinal direction L so as to present a concavity configured to receive the outer surface 50, such that the outer surface 50 nests in the concavity defined by the interior surface 52. It should be appreciated, of course, that the outer surface 50 can be sized as desired, such that the outer surface 50 can ride along the interior surface 52, or can be spaced from the interior surface 52 when the insertion member 40 is received in the receptacle 54. Referring to FIGS. 6I-6J, at least a portion up to an entirety of the interior surface 52 can be substantially straight as extends along the longitudinal direction L, such that when the outer surface 50 rides along the interior surface 52, the insertion member 40 is translatable in the receptacle 54 when the insertion member 40 is movable with respect to the receptacle 54.

In accordance with an alternative embodiment, the fixation member, which can be a bone screw or a set screw as described herein, can have a head that defines a first outer dimension along a first direction and a second outer dimension along a second direction that is angularly offset with respect to the first direction, such that the head defines a cam member. Accordingly, the fixation member is inserted into the fixation hole 28 such that the head of the fixation member is disposed in the fixation hole 28. When the fixation member is in one angular orientation, the head does not bear against the interior surface 44, or can bear against the interior surface 44 but with an insufficient force that would cause the outer surface 50 to expand against the interior surface to lock the insertion member 40 with respect to movement relative to the receptacle member 42. The fixation member can be moved, for instance rotated, to a second angular orientation whereby the head of the fixation member bears directly or indirectly against the interior surface 44 that defines the fixation hole 28, which thereby causes the outer surface 50 to expand and bear, directly or indirectly, against the interior surface 52, thereby locking the insertion member 40 with respect to movement relative to the receptacle member 42 in the manner described herein.

It should be appreciated that the outer surface 50 and the interior surface 52 can define any shape suitable so as to dictate the direction of angulation of the first and second links 32 relative to each other when the surfaces 50 and 52 ride along each other. In one embodiment, one or both of the outer surface 50 and the interior surface 52 can be cylindrical having a central axis that is oriented as desired. For example, the central axis of the cylinder can be oriented along the transverse direction T such that the first and second links are configured to angulate in-plane about an axis that extends along the transverse direction T, and are prevented from angulating about an axis that extends in a direction that is angularly offset with respect to the transverse direction T. Thus, the outer surface 50 and the interior surface 52 can be round surfaces so as to ride along each other and angulate the first and second links 32 with respect to each other about at least one axis. The round surface can be spherical, cylindrical, conical, or other round surface that can define an articulating joint as desired.

A method of constructing the bone fixation linkage 26 can include the step of placing the first link 32 adjacent the second link 32. The first link 32 can define the insertion member 40 that, in turn, defines the interior surface 44 and the outer surface 50, the interior surface 44 defining the fixation hole 28. The second link 32 can define the receptacle member 42 that defines the interior surface 52, the outer surface 56 opposite the interior surface 52. The interior surface 52 defines the receptacle 54 that extends along a central axis from the first end 34*a* configured to face an anatomical structure to a second end 34*b* that is opposite the first end 34*a*. The method can further include the step of inserting the insertion member 40 into the receptacle 54 along a direction substantially aligned with a central axis of the receptacle 54. The method can further include, during the inserting step, the step of bringing the insertion member 40 into contact with the receptacle member 42 so as to cause at least one of the insertion member 40 and the receptacle member 42 to deform from a neutral shape to a deflected shape. The method can further include the step of returning the deflected at least one of the insertion member 40 and the receptacle member 42 from the deflected shape to the neutral shape when the insertion member 40 is fully inserted into the receptacle 54 so as to be captured by the receptacle member 42. The bring step can further include the step of causing the insertion member 40 to deflect from the neutral shape to the deflected shape. The bringing step can cause the pair of spaced arms 45 that at least partially define the outer surface 50 to resiliently flex toward each other. The returning step can cause the outer surface 50 to nest in the interior surface 52, and can further cause the first and second links to be angulatable with respect to each other about the at least one axis. One of the links 32 can define a second attachment member configured to attach to a complementary attachment member of a third link, and the central axis of the second attachment member is parallel with respect to the respective one of the fixation hole and the receptacle of the one of the links.

Figure 7A:
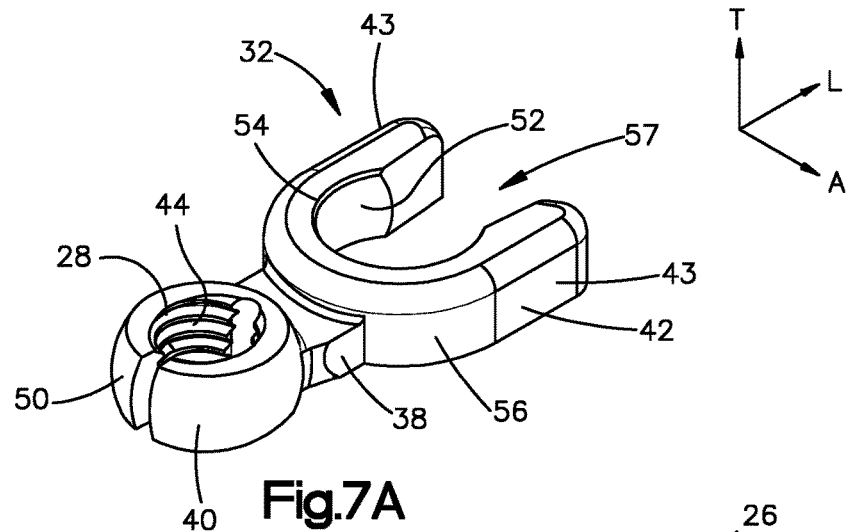
FIG. 7A is a perspective view of a link similar to the link illustrated in FIG. 3A, but including an open receptacle member.
Figure 7B:
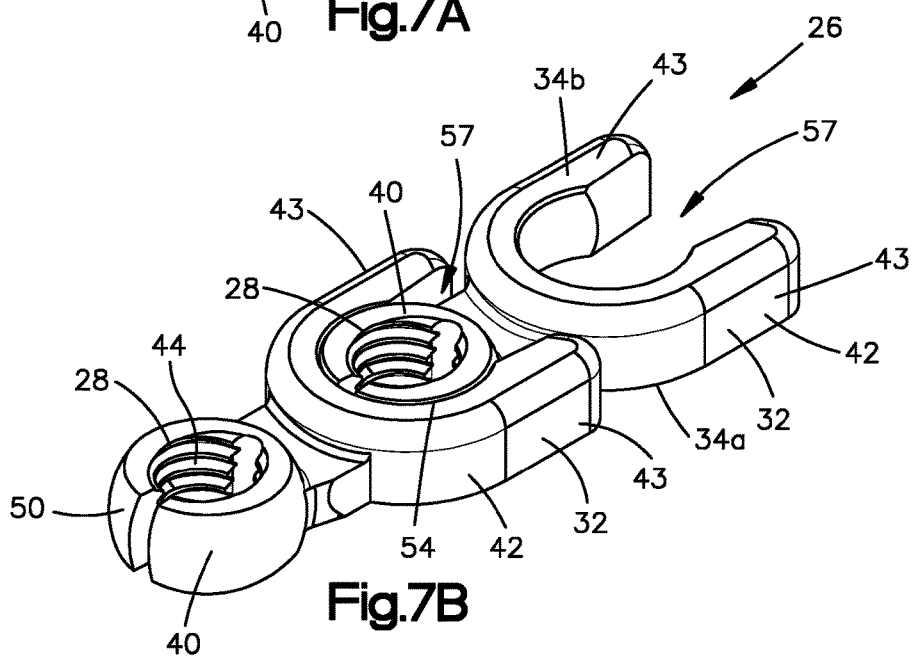
FIG. 7B is a perspective view of a pair of interconnected links of the type illustrated in FIG. 7A.
Figure 7C:
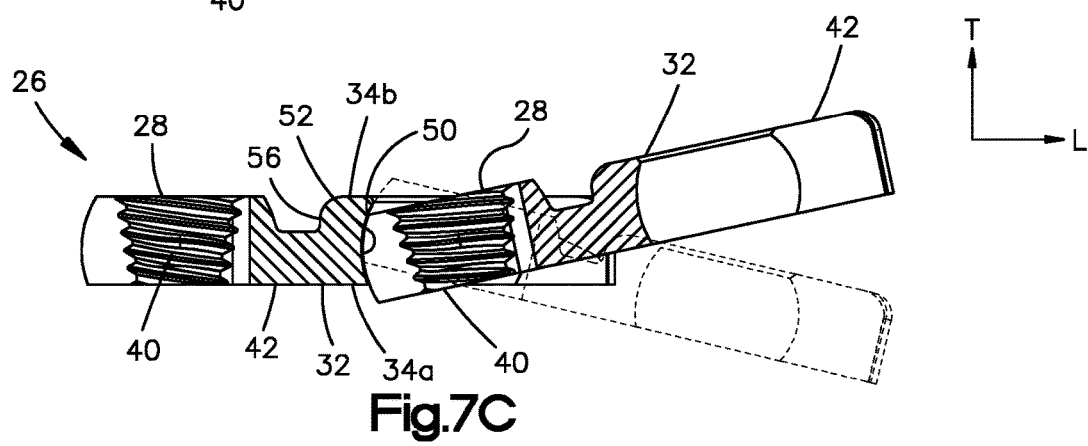
FIG. 7C is a perspective view of the pair of interconnected links illustrated in FIG. 7B, shown in an angulated configuration.

Referring now to FIG. 7A-7C, it should be appreciated that the receptacle member 42 can be devoid of the bridge 62 illustrated in FIG. 3A. Thus, at least a portion up to an entirety of the channel 57 can extend from the first end 34*a* to the second end 34 between the arms 43. Accordingly, the first link 32 is configured to angulate along the lateral axis a first distance from the neutral position to in a direction from the second end 34*b* toward the first end 34*a*, and a second distance from the neutral position in a direction from the first end 34*a* toward the second end 34*b*. When the receptacle member 42 is devoid of the bridge 62, the first and second distances can be equal to each other. When the receptacle member 42 includes the bridge 62, contact between the bridge 62 and the neck 38 of the first link 32 can limit the second distance to less than the first distance. Further, when the receptacle member 42 is devoid of the bridge 62, the first and second links 32 can be configured to angulate with respect to each other about their respective longitudinal axes a greater distance than when the second link 32 includes the bridge 62 that abuts the neck 38 of the first link 32.

Figure 7D:
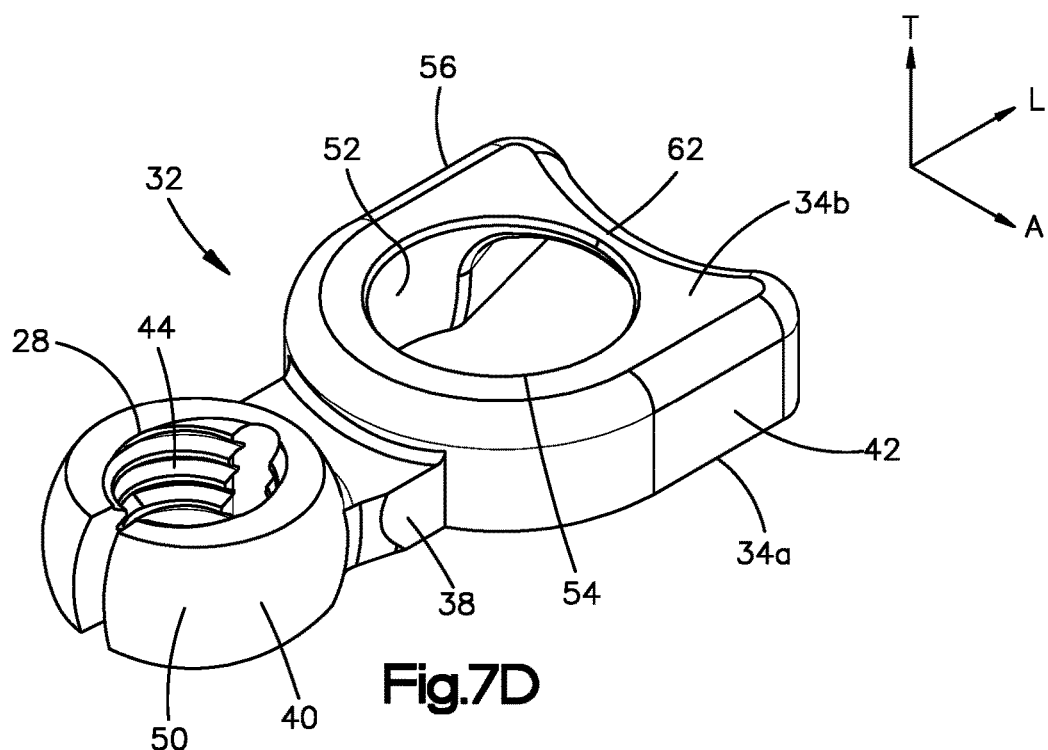
FIG. 7D is a perspective view of a links similar to the link illustrated in FIG. 3A, but showing the receptacle member constructed in accordance with an alternative embodiment.
Figure 7E:
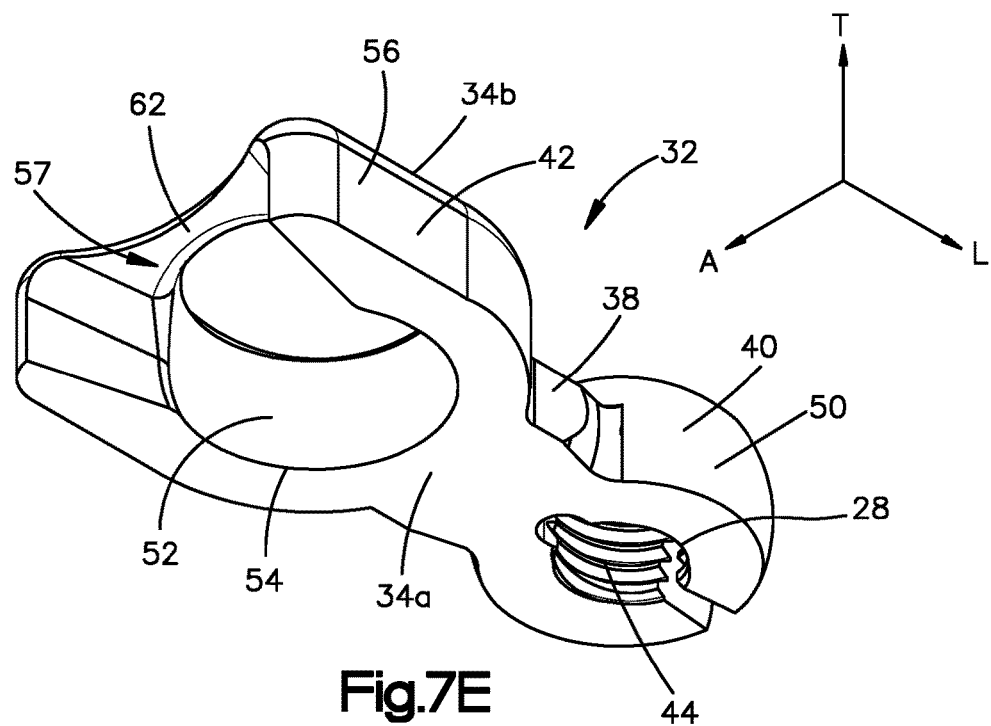
FIG. 7E is another perspective view of the link illustrated in FIG. 7D.

It should be appreciated that when the second link 32 includes the bridge 62, the bridge 62 can define any geometric shape as desired. For instance, the outer surface 56 at the bridge can be convex in a plane that is defined by the lateral direction A and the longitudinal direction L. In accordance with one embodiment, the outer surface 56 can define a curvature in the plane that is continuous with the curvature of the outer surface 56 of a remainder of the receptacle member 42. Alternatively, as illustrated in FIGS. 7D-7E, the outer surface 50 at the bridge 62 can be concave within the plane defined by the longitudinal direction L and the lateral direction A. Thus, the convex outer surface 50 of the receptacle member 42 of the second link 32 can nest within the concave outer surface 50 of the receptacle member 42 of the first link 32.

As described above, the channel 57 can be sized and positioned so as to define an angle at which the first direction of the link 32 extends with respect to the first direction of the second link 32. For instance, the receptacle member 42 defines a midpoint in the channel 57 that is disposed equidistantly between the first and second arms 43. The midpoint can lie on a midline that extends along the transverse direction equidistantly between the first and second arms 43. In accordance with the embodiment illustrated in FIGS. 1-6F, the midpoint can be inline, for instance along the longitudinal axis, with the central axes of the first and second attachment members, which can be defined by the insertion member 40, and in particular the fixation hole 28, and the receptacle member 42, and in particular the receptacle 54. Thus, a plane that extends along the longitudinal direction L and the transverse direction T can include the central axes of the first and second attachment members, and can further include the midpoint, and the midline. As a result, when the first and second interconnected links 32 are in the neutral position, the longitudinal axis L of the first link 32 can be inline with the longitudinal axis L of the second link. Thus, the longitudinal axes L of the first and second links 32 can lie in the same plane defined by the longitudinal direction L and the transverse direction T.

Figure 8A:
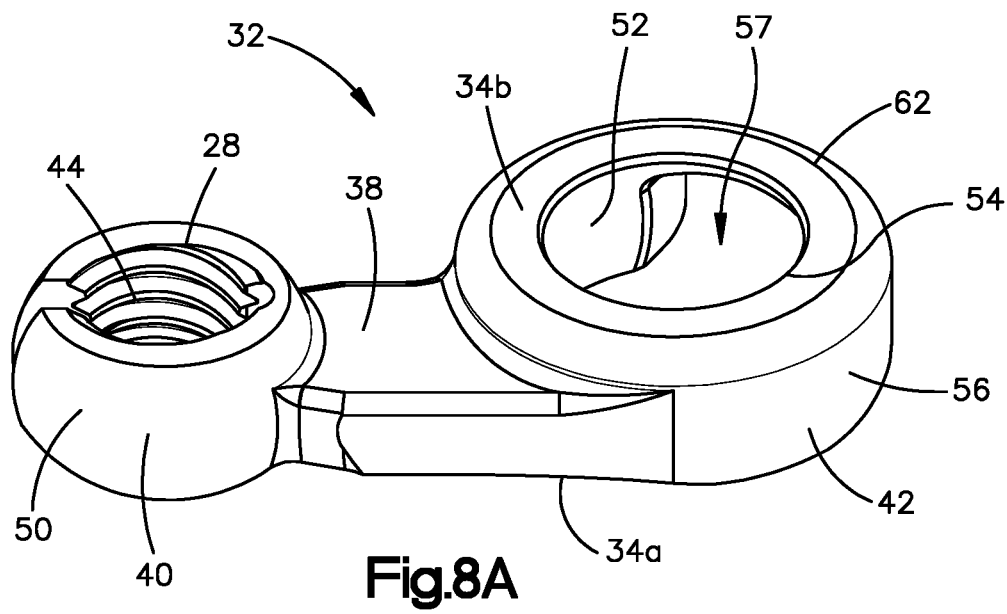
FIG. 8A is a perspective view of a link similar to the link illustrated in FIG. 3A, but showing the receptacle member including an oblique attachment channel.
Figure 8B:
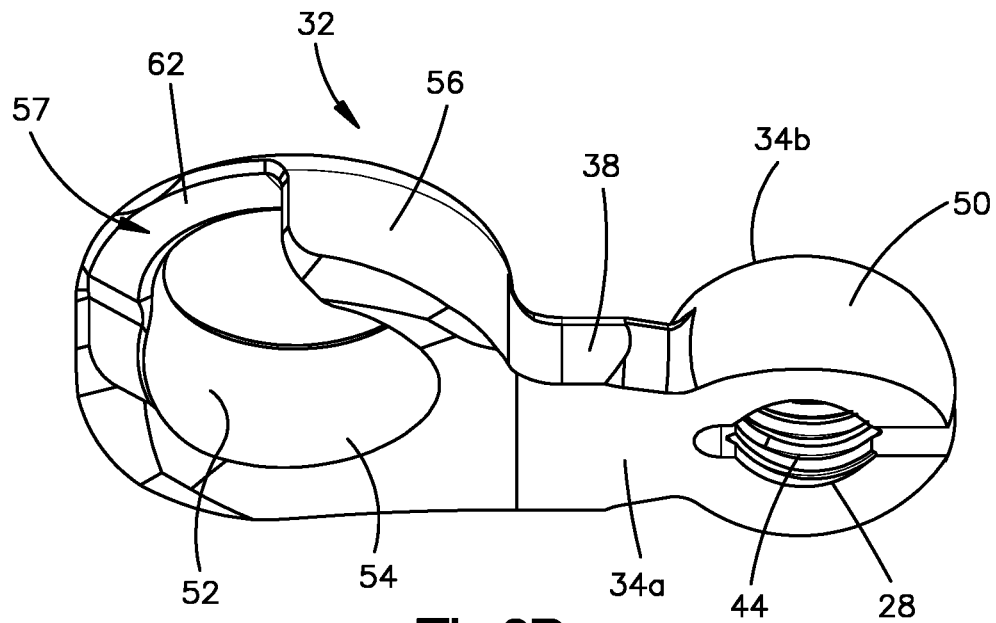
FIG. 8B is another perspective view of the link illustrated in FIG. 8A.

Alternatively, as illustrated in FIG. 8A-8B, the midpoint of the receptacle member 42 in the channel 57 can be offset along the lateral direction A from the longitudinal axis. As a result, when the first and second interconnected links 32 are in the neutral position, the longitudinal axis of the first link 32 can be angularly offset with respect to the longitudinal axis L of the second link 32. Otherwise stated, a plane that defines both the central axis of the fixation hole 28 and the central axis of the receptacle 54 can be offset from the midpoint, for instance along the lateral direction A.

Referring now to FIGS. 9A-9B, it should be appreciated that one or more of the links 32 of the bone fixation linkage, for instance the neck 38, can be pre-bent, for instance curved, and rigid such that the central axis of the first attachment member, which can be configured as the insertion member 40 is angularly offset with respect to the central axis of the second attachment member, which can be configured as the receptacle member 42. Alternatively, the neck can be curved in-plane such that the central axes of the first and second attachment members are substantially parallel to each other. The neck 38 can further be curved both in-plane and out-of-plane as desired. It should be appreciated that, unless otherwise indicated, reference to the central axis of the insertion member 40 and the receptacle member 42 can apply equally to any alternatively constructed attachment member. The neck 38 can extend along the transverse direction T along its direction of elongation between the central axes of the insertion member 40 and the receptacle member 42. For instance, the neck 38 can define an elbow that is bent, for instance about a lateral axis that extends along the lateral direction A. The central axis of the insertion member 40 can define any angle with respect to the central axis of the insertion member 42 as desired, greater than zero degrees and less than or equal to ninety degrees. Further, a kit of links 32 can include links having different angles defined by the central axis of the insertion member 40 and the central axis of the insertion member 42. The bent link 32 can be included in the bone fixation linkage to follow the contour of the outer surface of the underlying anatomical structure.

It should be appreciated that the bent link 32, along with other links 32 described herein, can define the longitudinal direction L at each of the insertion member 40 and the receptacle member 42. For instance, the longitudinal direction L at the insertion member 40 extends perpendicular to the central axis of the insertion member 40 along a plane that extends along the transverse direction T and includes both the central axis of the insertion member 40 and the central axis of the receptacle member 42. Similarly, the longitudinal direction L at the receptacle member 42 extends perpendicular to the central axis of the receptacle member 42 along the plane that extends along the transverse direction T and includes both the central axis of the insertion member 40 and the central axis of the receptacle member 42.

Figure 10A:
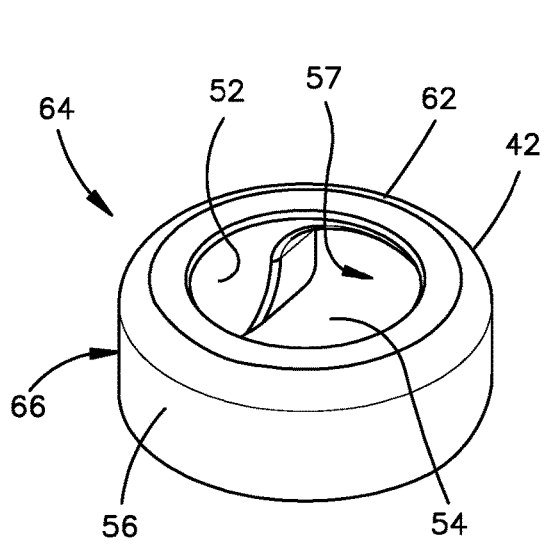
FIG. 10A is a perspective view of a receptacle cap constructed in accordance with one embodiment.
Figure 10B:
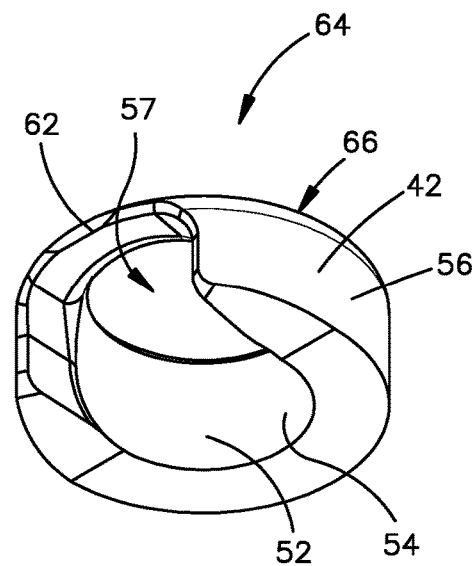
FIG. 10B is another perspective view of the cap illustrated in FIG. 10A.

Referring now to FIGS. 10A-11B, the bone fixation linkage can further include at least one cap 64 that is configured to interconnect with one of the attachment members of one of the links 32. The cap 64 can define the end of one or more of the links 32, and thus can define one or both ends of the bone fixation linkage 26. For instance, as illustrated in FIGS. 10A-10B, the cap 64 can be configured as a receptacle cap 66 that includes, and in some embodiments can consist of, a receptacle member 42 that can be constructed as described herein with respect to the receptacle members 42 of the links 32. In accordance with the illustrated embodiment, the outer surface 56 of the receptacle member 42 of the receptacle cap 66 defines the outer surface of the receptacle cap 66. The outer surface 56 of the receptacle member 42 of the receptacle cap 66 can, in one embodiment, be circular within a plane that is defined by the longitudinal direction L and lateral direction A when the receptacle cap 66 is interconnected with one of the links 32. The receptacle cap 66 can include the receptacle member 42 and no other attachment members. Thus, the receptacle member 42 of the cap 64 can be sized to receive an insertion member 40 of one of the links 32. For instance, when an insertion member 40 of one of the links 32 is not coupled to any complementary receptacle members 42 any of the links 32 of the bone fixation linkage, it may be desired to interconnect the receptacle cap 66 with the uncoupled insertion member 40. The receptacle cap 66 can, for instance, provide structural rigidity to the insertion member 40, for instance, when it is desired to insert a bone anchor through the fixation hole 28 of the uncoupled insertion member 40. It should be appreciated that the cap 64 can define a terminal end of the linkage 26 illustrated in FIG. 1.

Figure 11A:
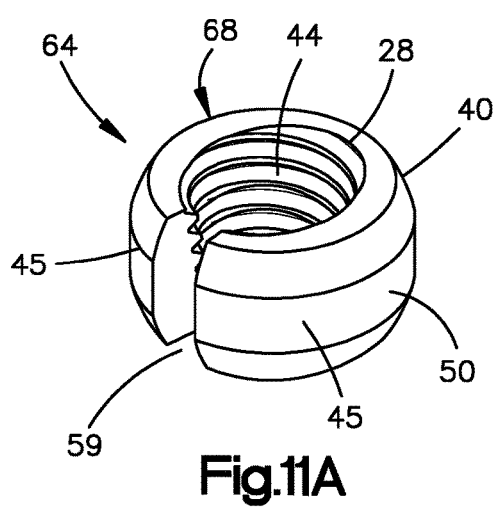
FIG. 11A is a perspective view of an insertion member cap constructed in accordance with one embodiment.
Figure 11B:
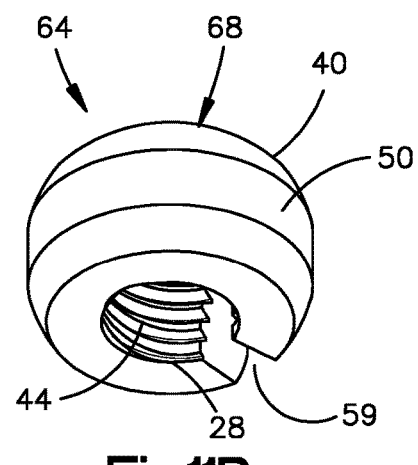
FIG. 11B is another perspective view of the insertion member cap illustrated in FIG. 11A.

As illustrated in FIGS. 11A-B, the cap 64 can be configured as an insertion cap 68 that includes, and in some embodiments can consist of, an insertion member 40 that can be constructed as described herein with respect to the insertion members 40 of the links 32. In accordance with the illustrated embodiment, the outer surface 50 of the insertion member 40 of the insertion cap 68 defines the outer surface of the insertion cap 68. The outer surface 50 of the insertion member 40 of the insertion cap 68 can, in one embodiment, be substantially spherical or otherwise round as described above, and configured to be inserted into the receptacle 54 of one of the links 32 and captured by the receptacle member 42 that defines the receptacle member 42. For instance, when a receptacle member 42 of one of the links 32 is not coupled to any insertion members 40 of the links 32 of the bone fixation linkage, it may be desired to interconnect the insertion cap 68 with the uncoupled receptacle member 42. The insertion cap 68 can, for instance, define the fixation hole 28 extending through the receptacle member 42, the fixation hole 28 configured to receive a bone anchor that is driven into the underlying anatomical structure, such as bone, in the manner described above. It should be further appreciated that the insertion cap 68 can angulate with respect to the receptacle member 42 of the link 32 about at least one axis as described above.

As described above with respect to FIGS. 1-6F, the insertion member 40 and the receptacle member 42 can define a frictional force at the interface between the outer surface 50 and the interior surface 52. The frictional force can be configured to provide a resistance to angulation of the first and second links 32 relative to each other. The outer surface 50 and the interior surface 52 can be substantially smooth in accordance with one embodiment. Alternatively, as illustrated in FIGS. 12A-13B, one or both of the outer surface 50 and the interior surface 52 can be textured so as to increase the frictional force at the interface between the outer surface 50 and the interior surface 52 when compared to the frictional force when each of the outer surface 50 and the interior surface 52 are smooth. For instance, in one embodiment, one or both of the outer surface 50 and the interior surface 52 can be surface treated, for instance during a bead blasting or shot peening process to create raised regions on the respective surface.

Figure 12A:
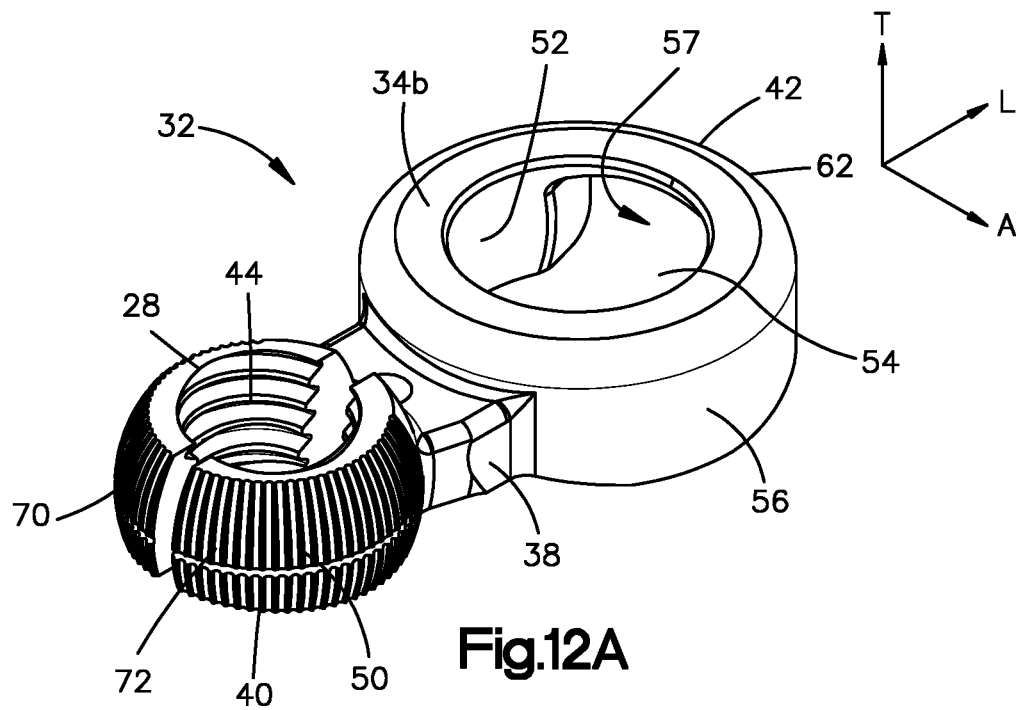
FIG. 12A is a perspective view of a link similar to the link illustrated in FIG. 3A, but showing the insertion member externally ribbed.
Figure 12B:
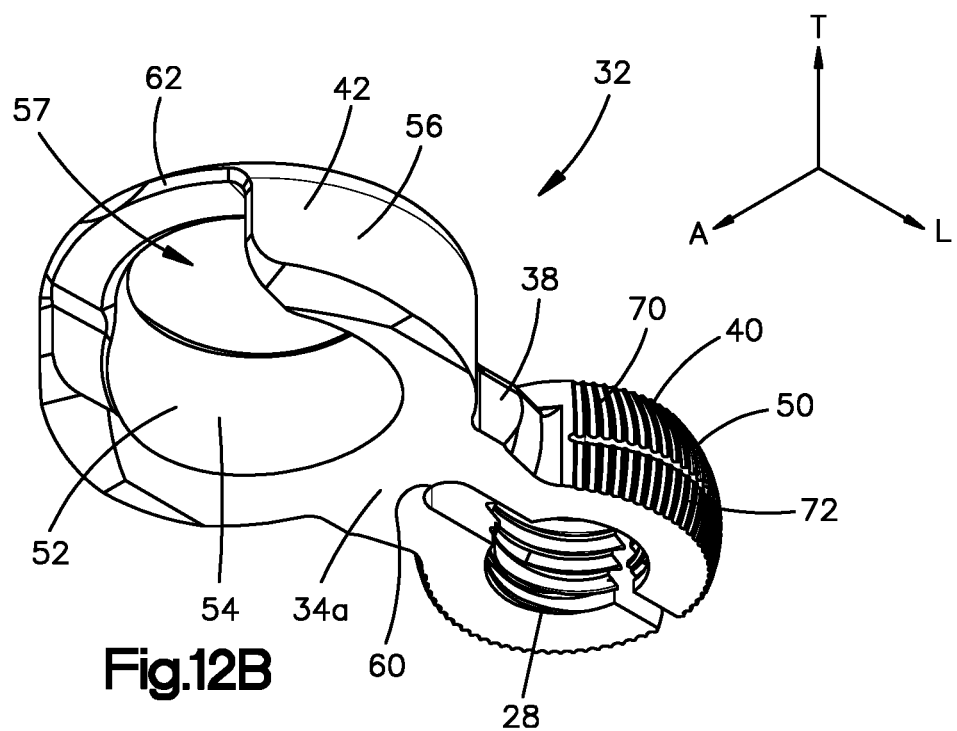
FIG. 12B is another perspective view of the link illustrated in FIG. 12A.
Figure 12C:
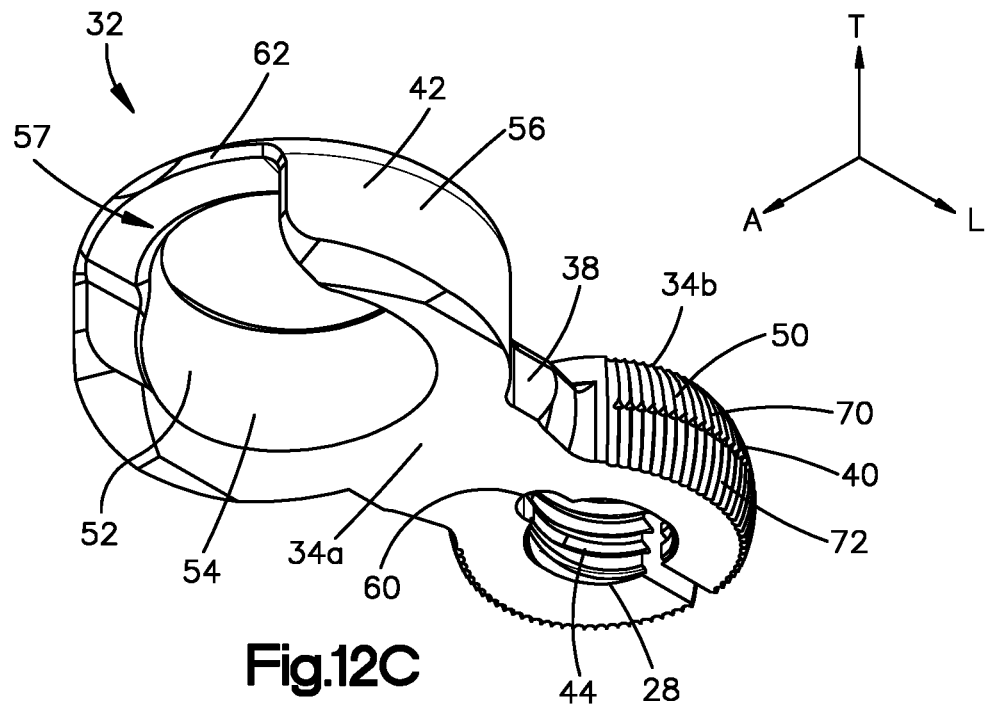
FIG. 12C is a perspective view of the link illustrated in FIG. 12A, but constructed in accordance with another embodiment.

Referring to FIGS. 12A-C, insertion member 40 can include a plurality of raised regions 70, such as ribs 72, that extend radially outward from the outer surface 50 along a direction away from the central axis of the insertion member 40. FIG. 12C illustrates that the relief recess 60 can extends from the interior surface 44 of the insertion member 40 into the neck 38 of the insertion member 40 any distance as desired, so as to correspondingly adjust the flexibility of the arms 45. As illustrated in FIGS. 12A-C, at least some up to all of the ribs 72 can be oriented substantially in a plane that is angularly offset, for instance orthogonal, to the first end 34a and the second end 34b and includes the central axis of the insertion member 40. The interior surface 52 of the receptacle member 42 can be smooth, such that the ribs 72 of the insertion member 40 are configured to abut the smooth interior surface 52 when the insertion member 40 is inserted into the receptacle member 42.

Figure 12D:
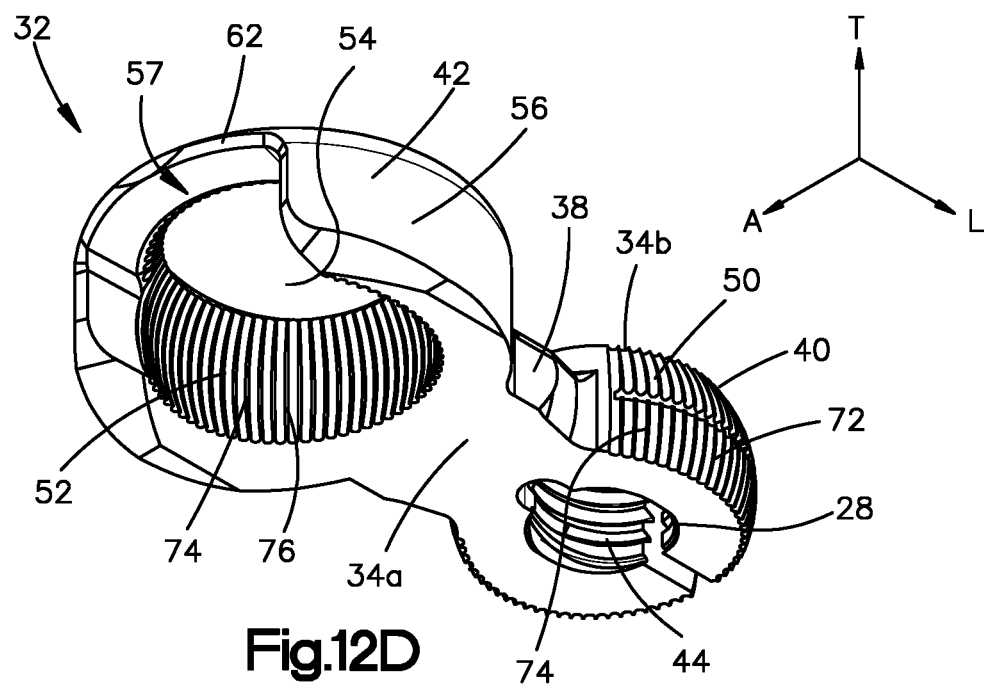
FIG. 12D is a perspective view of the link illustrated in FIG. 12C, but showing the receptacle member internally ribbed.

Alternatively, as illustrated in FIG. 12D, the receptacle member 42 can include a plurality of raised regions 74, such as ribs 76, that extend radially inward from the interior surface 52 along a direction toward the central axis of the receptacle member 42. In accordance with one embodiment, the ribs 76 of the receptacle member 42 can define a shape and orientation that is complementary to the ribs 72 of the insertion member 40. Thus, at least some up to all of the ribs 76 can be oriented substantially in a plane that is orthogonal to the first end 34a and the second end 34b and includes the central axis of the receptacle member 42. Accordingly, the raised regions, for instance the ribs 72, of the insertion member 40 can interdigitate with the raised regions, such as the ribs 76, of the receptacle member 42.

It should be appreciated that the interdigitation of the ribs 72 and 76 can be overcome with sufficient force so as to angulate the links 32 about any or all of the three axes as described above. Alternatively, the ribs 72 and 76 can be configured to interdigitate so as to lock the insertion member 40 and the receptacle member 42 with respect to angulation about the transverse axis and the longitudinal axis, and guide the links 32 to angulate with respect to each other about the lateral axis. Thus, the ribs 72 and 76 can define both textured regions and guide members that guide angulation of the respective links 32 in a predetermined direction. The ribs 72 and 76 can extend from the first end 34a to the second end 34b, or can define any length between the first end 34a and the second end 34b.

Figure 13A:
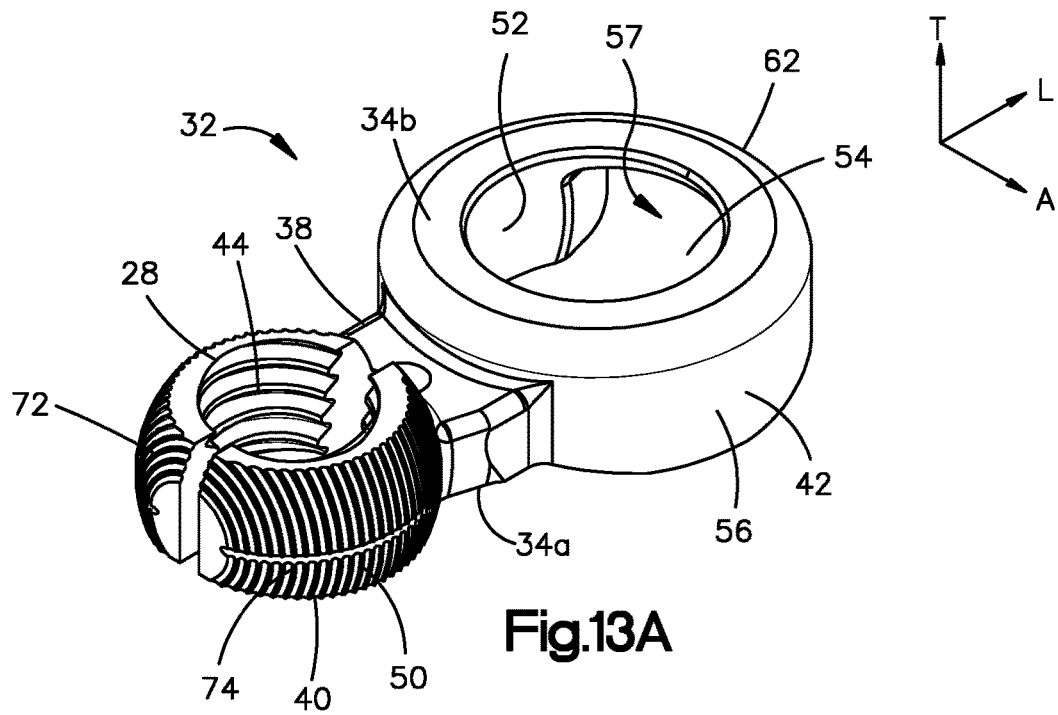
FIG. 13A is a perspective view of a link similar to the link illustrated in FIG. 12A, but showing the ribs in accordance with another embodiment.
Figure 13B:
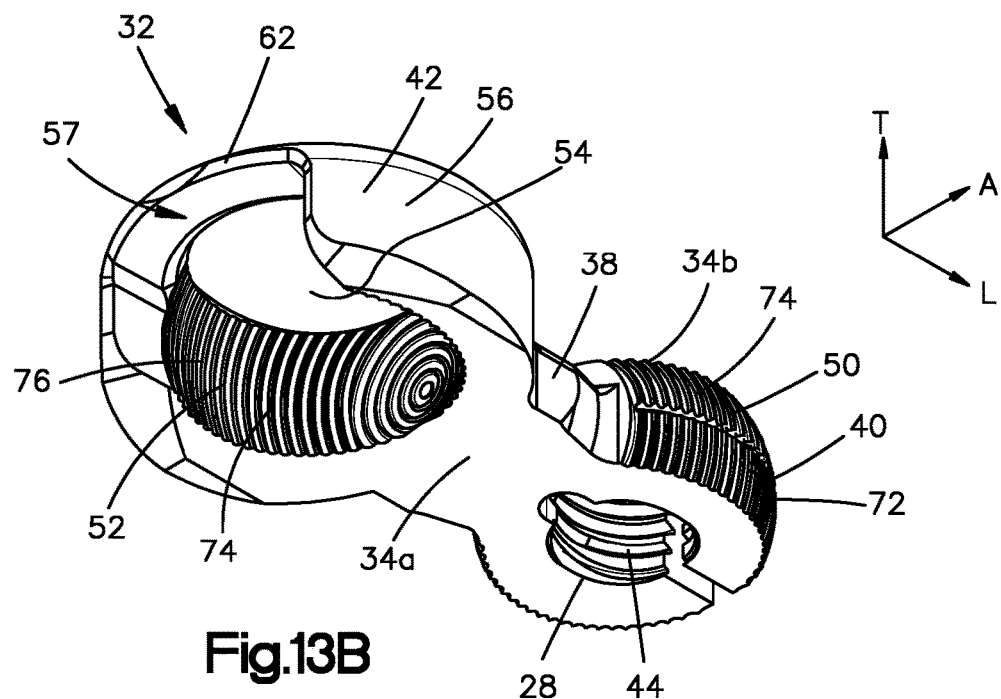
FIG. 13B is perspective view of a link similar to the link illustrated in FIG. 13A, but showing the receptacle member internally ribbed.

Referring now to FIGS. 13A-B, it should be appreciated that the ribs 72 and 76 can define any geometric configuration, including size and shape, as desired. For instance, at least some of the ribs 72 can be oriented in a plane that is orthogonal to both the first end 34a and the second end 34b and oblique to the outer surface 50 at the respective rib. The plane that defines one of the ribs 72 can be parallel to the respective plane that defines one or more up to all of the other ribs 72. Similarly, at least some of the ribs 76 can be oriented in a plane that is angularly offset, for instance orthogonal, to both the first end 34a and the second end 34b and oblique to the interior surface 52 at the respective rib. The plane that defines one of the ribs 76 can be parallel to the respective plane that defines one or more up to all of the other ribs 76. The ribs 72 and 76 can be sized to interdigitate so as to guide angulation of the links 32 about the longitudinal axis, while preventing angulation of the links about the lateral axis and the transverse axis.

It should be appreciated that the raised regions as illustrated in FIGS. 12A-13B can be sized and shaped in accordance with any suitable alternative embodiment as desired. The raised regions of the insertion member 40 can interdigitate with the raised regions of the receptacle member 42 so as to prevent relative movement between the insertion member 40 and the receptacle member 42. Thus, when the fastener causes the insertion member to bear against the receptacle member 42, the raised regions can interlock so as to prevent relative angulation between the insertion member 40 and the receptacle member 42. Thus, friction or a positive interlock between the outer surface 50 and the interior surface 52 can prevent the insertion member 40 and the receptacle member 42 from angulating with respect to each other about the at least one axis. As illustrated in FIG. 13C, the raised region of one of the outer surface 50 and the interior surface 52 can be configured as at least one dimple 71, and the raised region of the other of the outer surface 50 and the interior surface 52 can be configured as at least one projection 73 configured to fit within the at least one dimple so as to interlock the outer and interior surfaces 50 and 52 and prevent movement of the respective insertion member 40 with respect to the receptacle member 42. For instance, the interior surface 52 can define a plurality of dimples 71 and the outer surface 50 can define a plurality of projections 73. The dimples 71 can be disposed along a portion or an entirety of the interior surface 52, and the projections 73 can be disposed along a portion or an entirety of the outer surface 50. For instance, the projections 73 can be substantially coplanar with each other. Alternatively still, referring to FIG. 13D, the raised regions of the outer surface 50 of the insertion member 40 can be configured to frictionally engage the raised regions of the interior surface 52 of the receptacle member 42. The raised regions of the outer surface 50 and the interior surface 52 can be sized and shaped as desired. It is further appreciate that the raised regions of one or both of the outer surface 50 and the interior surface 52 can deform when the outer surface 50 bears against the interior surface 52 so as to cause the surfaces 50 and 52 to both frictionally engage each other and to interlock.

Referring now to FIGS. 14A-C, and as described above, the fixation holes 28 of the insertion members 40 can be configured to receive a fixation member, which can be provide as a bone anchor 30. For instance, the interior surface 44 can be threaded so as to threadedly mate with a threaded head of a locking bone screw. As illustrated in FIGS. 14A-14C, the interior surface 44 can be configured to lock with the threaded head of the locking bone screw at a selectable angle in any direction with respect to the central axis of the fixation hole 28 within a range of angles that define a cone. Thus, fixation member can be inserted through the fixation hole 28 in the manner described above. In embodiments whereby the fixation member is a locking screw, the locking screw can be inserted through the fixation hole 28 and driven into the underlying anatomical structure at any angle within the range of angles, and the head of the locking screw can threadedly mate with the threaded interior surface 44 of the insertion member 40.

The insertion member 40 can define projections 84 such as threads that extend radially inward from the respective columns 78 toward the central axis of the insertion member 40. The bone screws 30 can be configured as variable-angle locking screws whose heads are configured to threadedly mate with the projections 84 of each of the columns 78 at a selectable angle in any direction with respect to the central axis of the fixation hole 28 within a range of angles that define a cone. In accordance with one embodiment, the projections 84 of each of the columns 78, if joined so as to be continuous with the projections 84 of the adjacent columns 78, can define a helical path. Alternatively, the projections 84 can be concentric with each other. Variable-angle holes and screws are described in U.S. Pat. No. 8,343,196, the disclosure of which is hereby incorporated by reference as if set forth in its entirety herein. As illustrated in FIG. 14C, the outer surface 50 of the insertion member 40 can be scalloped, such that the insertion member 40 defines recesses 86 that extend into the outer surface 50 between the first end 34a and the second end 34b, for instance from the first end 34a to the second end 34b. The recesses 86 can be can be oriented substantially in a plane that is orthogonal to the first end 34a and the second end 34b and includes the central axis of the insertion member 40. The regions of the outer surface 50 between adjacent recesses 86 can be referred to as raised regions that increase the frictional forces when the outer surface is captured in the interior surface 52 of the receptacle member 42.

Referring now to FIGS. 15A-15D, it is appreciated that one or more of the links 32 of the bone fixation linkage can be configured as a plate 88 having a plate body 90, and at least one attachment member, which can be configured as a receptacle member (FIGS. 15A-15B) or an insertion member 40 (FIGS. 15C-15D) of the type described above, that is monolithic with the plate body 90. Thus, one or more up to all of the links can be configured as a plate having one or more screw holes that extend through the plate body, and an attachment member 36, for instance at one end of the plate body, that can be configured as an insertion member 40 or a receptacle member 42. As described herein, the receptacle member 42 of the plate 88 is configured to receive and capture an insertion member 40 of an adjacent one of the links 32. Similarly, the insertion member 40 of the plate 88 is configured to be inserted into and captured by a receptacle member 42 of an adjacent one of the links 32 as described herein. The plate 88 can further include a plurality of bone fixation holes 92 that extend through the plate body 90 from the first end 34a to the second end 34b.

One of the bone fixation holes can be disposed at one end of the plate body 90, and the attachment member can be disposed at another opposite end of the plate body 90. It should be appreciated that the plate 88 can further include a pair of attachment members, such as an insertion member 40 and a receptacle member 42, any number of insertion members 40 as desired, any number of receptacle members, or combinations thereof, so as to attach to more than one adjacent link 32. It should be appreciated that the plate 88 can define one or both outermost ends of the linkage 26.

The bone fixation holes can be spaced between the pair of attachment members of the plate 88, or can be otherwise positioned as desired. The bone fixation holes of the plate 88 can be defined by a smooth interior surface of the plate body 90, a threaded interior surface, for instance to threaded columns, a combination of a threaded surface portion and an unthreaded smooth surface, and can be conically or cylindrically shaped as desired, in the manner described above. The plate 88 can define a linear distance between the pair of attachment members that is greater than the linear distance between the first and second attachment members of the links 32 that are devoid of bone fixation holes between the attachment members. It should be noted that FIGS. 15A-15D illustrate respective portions of the plate 88.

Referring now to FIGS. 16A-16B, and as described above, one or more of the links 32 can include more than two attachment members. For instance, as illustrated in FIG. 16A, the link 32 can include a first attachment member 36a, which can be configured as the insertion member 40, a second attachment member 36b, which can be configured as the receptacle member 42, and the neck 38 that extends from the first attachment member 3a to the second attachment member 36b as described above. The link 32 can further include a third attachment member 36c, which can be configured as an insertion member or a receptacle member as desired. In accordance with the illustrated embodiment, the third attachment member is configured as an insertion member 40 constructed as described herein. The link 32 can further include a second neck 38a that extends between the first attachment member 36a and the third attachment member 36c as described above with respect to the first and second attachment members 36a and 36b. The link 32 can define a first longitudinal axis that extends between and perpendicular to the central axis of each of the first attachment member 36a and the second attachment member 36b. The link 32 can define a second longitudinal axis that extends between and perpendicular to the central axis of each of the first attachment member 36a and the third attachment member 36c.

The second longitudinal axis is angularly offset with respect to the first longitudinal axis, for instance so as to define any angle as desired. Thus, the link 32 illustrated in FIG. 16A can be configured to attach to two different links so as to define two angularly offset branches of links 32 of the bone fixation linkage. It may be desired to define multiple branches of links 32 depending on the geometry underlying anatomical structure. For instance, the linkage can include a first branch of links configured to attach to the condyle process and a second link that is configured to attach to the coronoid process, though as described above the links 32 are not limited to be attached to the mandible, and can be configured to attachment to any suitable underlying bone as desired.

As illustrated in FIG. 16B, the second neck 38a can extend from the first neck 38 to the third attachment member 36c. Thus, the second longitudinal axis of the third attachment member can be defined by a straight line that extends from the central axis of the third attachment member to the first longitudinal axis along a direction perpendicular to the central axis of the third attachment member 36c. The second longitudinal axis can define the central axis of the second neck 38a, depending on the geometric configuration of the second neck 38a. It should be appreciated that the second neck 38a, and the second longitudinal axis, can define any angle as desired with respect to the first neck 38, and thus the first longitudinal axis, greater than zero degrees and less than or equal to ninety degrees. Thus, the link 32 illustrated in FIG. 16B can be configured to attach to two different links so as to define two angularly offset branches of links 32 of the bone fixation linkage.

It should be appreciated that the linkage 26 illustrated in FIG. 1 can include one or more interconnected ones of the links 32 constructed in accordance with any of the embodiments described herein. Further, it should be appreciated that one or more up to all of the features of each link 32 can be integrated into each other link 32 unless otherwise indicated. Further, it should be appreciated that certain ones of the links 32 may be sized differently than other ones of the links. For instance, the outer surfaces 50 and interior surfaces 44 of one or more of the links 32 may be different than one or more others of the links 32. Further, one or more of the links 32 can define a longitudinal distance that is greater or less than others of the links 32. Further, it should be appreciated that one or more of the links 32 can have any one of the features described herein that are not included in one or more others of the links 32.

Referring now to FIGS. 17A-17C, it should be appreciated that the bone fixation linkage can be constructed in accordance with any suitable alternative embodiment as desired. For instance, a bone fixation linkage 126 can include a plurality of links 32. At least one or more of the links 32 up to all of the links 32 can be constructed so as to define first and second attachment members 136a and 136b that are configured to be coupled to respective ones of the second attachment regions 136b and the first attachment regions 136a, respectively, of other links 132 of the linkage 126, such that the links 132 can angulate with respect to each other about the at least one axis. As illustrated in FIGS. 17A-17C, the at least one axis can be oriented in the transverse direction T. As described above, the bone fixation linkage 126, and thus each of the links 132, can define a bottom end having a first surface 134a that is configured to face the underlying anatomical structure, such as the bone 24, and a top end having a second surface 134b that is opposite the first surface 134a. Each of the first and second surfaces 134a and 134b can be sized and shaped as desired, and can define any number of surfaces as desired, including at least one or more surfaces.

Each link 132 can include at least a first attachment member 136a and a second attachment member 136b that are configured to attach to each other such that one of the first and second attachment members 136a-b of a first one of the links 132 is attached to, for instance captured by, a complementary one of the first and second attachment members 136a-b of a second one of the links 132 so as to define an articulating joint. Thus, the first and second links 132 can angulate with respect to each other about at least one axis, which can be oriented in the transverse direction T. The bone fixation linkage 126 can include any number of links 132 as desired depending on at least one of several factors, including on the desired length of the bone fixation linkage 126, the desired maneuverability of the bone fixation linkage 126, and the desired geometrical shape of the bone fixation linkage 126. In this regard, it should be appreciated that the links 132 can be attached to each other in any manner as desired such that the bone fixation linkage 126 defines any size and shape so as to conform to the underlying anatomy of the underlying bone, which can be any suitable bone as desired, for instance one or more bones of the hand or the distal radius, among others. Further, it should be appreciated that the bone fixation linkage 126 can be configured to join two different types of bone plates. For instance, the bone fixation linkage 126 can connect to a hand bone plate at one end, and to a distal radius bone plate at another end. In accordance with one embodiment, the outermost links 132 of the bone fixation linkage 126 can define outermost first attachment member 136a that are configured to be inserted into respective bone screw holes of the first and second bone plates, which can thus define attachment members, in accordance with any embodiment described herein with respect to securement of the first attachment members 136a to second attachment members 136b. Thus, the hand plate and the distal radius plate can be referred to as links that are configured to attach to the links 132 in the manner described herein. Further, it should be appreciated that the links 132 of the bone fixation linkage 126 can be substantially identical to each other, or one or more up to all of the links 132 can be constructed in accordance with alternative embodiments with respect to one or more other ones of the links 132, as is described herein. For instance, one or both of the first and second attachment members 136a and 136b can be included in one or more of the links 32 of the linkage 26 described above. Similarly, one or more of the first and second attachment members 136a and 136b of the links 132 described above can be incorporated in the links 132 of the linkage 126. Thus, different regions of a linkage can include different links of any type described herein.

In accordance with one embodiment, each link 132 can include a neck 138 that extends between the pair of attachment members 136a-b, for instance from the first attachment member 136a to the second attachment member 136b. The neck 138 can be monolithic with the first and second attachment members 136a-b. It should be appreciated unless otherwise indicated, that reference throughout this disclosure to first and second links 132 is intended to refer to the first link 132 whose first attachment member 136a is configured to be coupled to the second attachment member 136b of the second link 132 to define an articulating joint. Thus, the first and second links 132 can be constructed as illustrated with respect to the link 132 of the type illustrated in FIGS. 17A-B, or otherwise described herein.

Each link 132 can include a monolithic link body 133 that includes the neck 138, and the attachment members 136a-b. The first attachment member 136a can include interior surface 144 that defines an opening, such as a first fixation hole 128, that extends from the first surface 134a to the second surface 134b and is configured to receive respective ones of the bone anchors 130. The bone anchors 130 each include a shaft 130a that can be threaded so as to threadedly purchase with the underlying anatomical structure, and a head 130b that is coupled to the shaft. The head 130b can compress against the second surface 134b, or can threadedly purchase with the link 132 in the first fixation hole 128 as desired. For instance, the interior surface 144 can include projections such as threads that threadedly purchase with complementary threads of the head of the bone anchor 130, which can be configured as a locking screw, as the bone anchor 130 is driven through the first fixation hole 128 and into the underlying anatomical structure. Alternatively, the interior surface 144 can be smooth, or include a smooth portion, that is configured such that the head of the bone anchor 130, which can be configured as a compression screw whereby the head is unthreaded, can abut the smooth interior surface 144, or the threaded interior surface 144, and compress the respective link 132 against the underlying anatomical structure as the bone anchor 130 is driven through the first fixation hole 128 and into the underlying anatomical structure. The first attachment member 136a further include an outer surface 150 that is opposite the interior surface 144. Alternatively still, a first portion of the interior surface 144 can be smooth and devoid of threads, and a second portion of the interior surface 144 can be threaded. For instance, the first portion of the interior surface 144 can be disposed adjacent the second surface 134b, and the second portion of the interior surface 144 can be disposed adjacent the first end. At least part up to all of the interior surface 144 can be conical, cylindrical, or alternatively shaped as desired. The interior surface 144 is configured to receive a bone fixation member as described in U.S. Patent Publication Serial No. 2008/0140130, the disclosure of which is hereby incorporated by reference as if set forth in its entirety herein.

With continuing reference to FIGS. 17A-17C, the second attachment member 136b includes an interior surface 152 and an outer surface 156 opposite the interior surface 152. The interior surface 152 defines a second fixation hole 153 that is aligned with the first fixation hole 128 of the first attachment member 136a when the second attachment member 136b has been coupled to the first attachment member 136a. Because the second attachment member 136b can be positioned between the first attachment member 136a and the underlying bone 24, the bone anchor 130 can extend through the first and second fixation holes 128 and 153 and into the underlying bone 124. The second attachment member 136b can define an outer surface 156 opposite the interior surface 152.

The first and second attachment members 136a and 136b, can be spaced from each other along a first direction, such as the longitudinal direction L. Each of the links 132 can be elongate along the longitudinal direction L. Thus, the neck 138 can define a central axis that extends from the first attachment member 136a to the second attachment member 136b, and in particular extends perpendicularly through the central axes of the first attachment member 136a and the second attachment member 136b, along the first or longitudinal direction L. Further, the first and second fixation holes 128 and 153 of each given link 132 can define respective central axes that are spaced from each other and aligned with each other along the first direction. The first and second surfaces 134a and 134b are spaced from each other along the second direction, such as the transverse direction T that is substantially perpendicular to the longitudinal direction L. The link 132 can define opposed sides 158 that are spaced from each other along a third direction, which can be referred to as a lateral direction A that is substantially perpendicular to both the longitudinal direction L and the transverse direction T. The longitudinal direction L and the lateral direction A can define a plane, such that angulation of at least one or more up to all of the links 132 with respect to another one of the links 132, for instance an adjacent one of the links 132, within or along the plane can be referred to as in-plane angulation. Angulation of at least one or more up to all of the links 32 with respect to another one of the links 32, for instance an adjacent one of the links 32, along a direction that intersects the plane, and thus has a directional component in the second or transverse direction T, can be referred to as out-of-plane angulation. Further, at least one or more up to all of the links 132 can angulate torsionally with respect to another one of the links 132, for instance an adjacent one of the links 132, about a longitudinal axis that extends along the longitudinal axis L. As will be described in more detail below, the links 132 can be configured to angulate with respect to each other in-plane, out-of-plane, torsionally, or a combination of two or more up to all thereof. In-plane angulation can cause the links 132 to move in a direction that is substantially parallel or tangential to the underlying anatomical structure. Out-of-plane angulation can cause the links 132 to move in a direction toward or away from the underlying anatomical structure.

Angulation of the linkage 126 will now be described with continuing reference to FIGS. 17A-17C. In particular, the first surface 134a of the first attachment member 136a and the second surface 134b of the second attachment member 136b can be shaped as desired. For instance, one of the first surface 134a of the first attachment member 136a and the second surface 134b of the second attachment member 136b can be concave, and the other of the first surface 134a of the first attachment member 136a and the second surface 134b of the second attachment member 136b can be convex. Alternatively, both the first surface 134a of the first attachment member 136a and the second surface 134b of the second attachment member 136b, can be substantially flat or otherwise shaped. It should be appreciated that the first surface 134a of the first attachment member 136a and the second surface 134b of the second attachment member 136b can define matching shapes. Thus, the first surface 134a of the first attachment member 136a of a first link 132 can seat against the second surface 134b of the second attachment member 136b of the second link 132. For instance, the shape of the first surface 134a of the first attachment member 136a can geometrically match the shape of the second surface 134b of the second attachment member 136b. Further, the first surface 134a of the first attachment member 136a can define a first geometry, and the second surface 134b of the second attachment member 136b can define a second geometry that nests or interlocks with the first geometry. For instance, the first geometry can include a plurality of protrusions 170a and recesses 170b. The protrusions 170a and recesses 170b can be alternatingly arranged. For instance, the protrusions 170a and recesses 170b can be alternatingly arranged about the first fixation hole 128 circumferentially. The protrusions 170a and recesses 170b can extend along a radial direction that extends from the interior surface 144 to the outer surface 150. In one example, the protrusions 170a and recesses 170b can extend from the interior surface 144 to the outer surface 150.

Similarly, the second geometry can include a plurality of protrusions 172a and recesses 172b. The protrusions 172a and recesses 172b can be alternatingly arranged. For instance, the protrusions 172a and recesses 172b can be alternatingly arranged about the second fixation hole 153 circumferentially. The protrusions 172a and recesses 172b can extend along a radial direction that extends from the interior surface 152 to the outer surface 156. In one example, the protrusions 172a and recesses 172b can extend from the interior surface 152 to the outer surface 156. It should be appreciated that the protrusions and recesses 170a-b and 172a-b can have any size and shape as desired. When the first attachment member 136a is coupled to the second attachment member 136b and the first and second geometries are interlocked with each other, the protrusions 172a are received in the recesses 170b, and the protrusions 170a are received in the recesses 172b. In one embodiment, the head 130b of the bone anchor 130 can compress the first surface 134a of the first attachment member 136a of the first link 132 against the second surface 134b of the second attachment member 136b of the second link 132, thereby locking the first and second links 132 with respect to angulation relative to each other. Alternatively, the head 130b can threadedly purchase with at least one or both of the interior surfaces 144 and 152 while the first and second geometries are engaged so as to prevent separation of the first and second geometries, thereby maintaining the first and second geometries in their nested configuration. For instance, the head 130b can threadedly purchase with the first interior surface 144. Thus, the bone anchor 130 can be moved to a locked position whereby the first and second links 132 are prevented from angulating with respect to the other.

When the bone anchor 130 is not in the locked position, the first and second links 132 are angulatable with respect to each other. For instance, the first and second links 132 can angulate with respect to each other in-plane. In one example, each of the first and second fixation holes 128 and 153 can extend from the first surface 134a to the second surface 134b along a central axis. The central axis can be oriented in the transverse direction. The first and second links 132 can angulate with respect to one or both of the central axes of the first and second fixation holes 128 and 153. In this regard, it should be appreciated that the central axes can be aligned with each other. The bone anchor 130 can define a neck 130c that is disposed between the shaft 130a and the head 130b. The neck 130b can define a diameter greater than the shaft 130a and less than the head 130b. Similarly, the second fixation hole 153 can define a cross-section greater than that of the first fixation hole 128. The interior surface 144 can be flexible to allow the neck 130c to pass through the first fixation hole 128 and abut the interior surface 152 of the second attachment member 136b. Alternatively, the neck 130c can threadedly purchase with the interior surface 144, such that the neck 130c advances to a location whereby the first attachment member 136a is captured between the head 130b and the neck 130c.

When the first and second links 132 are attached to each other, the first attachment member 136a is placed against the second attachment member 136b, such that the second attachment member 136b is disposed between the first attachment member 136a and the underlying bone 24. Thus, the second attachment member 136b of the second link 132 can be disposed adjacent the first attachment member 136a of the first link in an inward direction along the transverse direction T. Similarly, the first attachment member 136a of the first link 132 can be disposed adjacent the second attachment member 136b of the second link 132 in an outward direction along the transverse direction T. It should be appreciated that the first surface 134a is spaced from the second surface 134b in the inward direction. Thus, the second surface 134b is spaced from the first surface 134a in the outward direction.

In accordance with one embodiment, the bone anchor can be preloaded in the first fixation hole 128, such that the link body 133 of the first link 132, and thus the link 132, is disposed between the neck 130c and the head 130a. Thus, the shaft 130a extends from the first link 132 in the inward direction. As described above, the shaft 130a can be inserted through the first fixation hole 128 until the neck 130c contacts the second surface 134b. The neck 130c can then move in the inward direction past the interior surface 144 as described above. For instance, the body 133 of the first link 132 can be flexible so as to allow the neck 130c to translate past the interior surface 144. Alternatively or additionally, the neck 130c and the interior surface 144 can be threaded, such that the neck 130c threadedly purchases with the interior surface 144 as the neck 130c moves past the interior surface 144. Because the neck 130c and the head 130b each have a cross-sectional dimension greater than the fixation hole 128, the first plate 132 can be captured between the head 130b and the neck 130c with respect to the transverse direction T.

It should be appreciated that, unless otherwise indicated, each of the links described herein can be preloaded with the respective bone anchor. For instance, the insertion members 40 can be preloaded with the bone anchor 130 prior to being received in the respective receptacle members 52. For example, as illustrated in FIG. 6C, the bone anchor 130 can be preloaded onto the insertion member 40 through the fixation hole 28 such that the first link 32 is captured between the neck 130c and the head 130b. The insertion member 40 can then be inserted into the receptacle member 52, and the first and second links 32 can be angulated with respect to each other as desired. The head 130b can then be threaded against the interior surface 44, thereby locking the first and second links to each other with respect to relative angulation, as described above.

In one embodiment, as illustrated in FIGS. 17A-17C, once the bone anchor 130 has been preloaded onto the first link 132, the second link 132 can be coupled to the first link 132 to define the linkage 126. For instance, the shaft 130a of the bone anchor 130 can be inserted through the second fixation hole 153, such that the neck 130c is disposed in the second fixation hole 153. The second fixation hole 153 can define a cross-sectional dimension that is slightly greater than the outer cross-sectional dimension of the neck 130c.

Thus, the bone anchor 130 can guide the first and second interconnected links 132 to angulate in-plane. Further, the projections and recesses 170a-b and 172a-b can be sized wider at the respective outer surfaces 150 and 156 than at the respective interior surfaces 144 and 152. Thus, the first and second geometries can be configured to interlock only when the angulation of the first and second links is in-plane. Alternatively, the neck 130c can be sized smaller than the second fixation hole 153, or the bone anchor 130 can be devoid of the neck 130c. Thus, the first and second links 132 can angulate with respect to each other out-of-plane and torsionally as desired. It should be appreciated that the protrusions and recesses 170a-b and 172a-b can be sized and shaped to interlock with each other after the first and second links 132 have angulated with respect to each other in-plane, out of plane, and torsionally. Accordingly, once the first and second links 132 have been angulated with respect to each other as desired, for instance to fit against the underlying bone 24 in a select orientation, the shaft 130a can be driven into the underlying bone 24 a sufficient distance that causes the head 130b to compress against the second surface 134b of the first link 32. The first link 32 therefore compresses against the second link 32, thereby urging the first and second links 32 against each other while the first and second geometries are interlocked. The interlocked first and second geometries thus prevent further angulation of the first and second links 32 relative to each other.

The embodiments described in connection with the illustrated embodiments have been presented by way of illustration, and the present invention is therefore not intended to be limited to the disclosed embodiments. Accordingly, those skilled in the art will realize that the invention is intended to encompass all modifications and alternative arrangements included within the spirit and scope of the invention, as set forth by the appended claims.

What is claimed:
1. A bone fixation linkage comprising:
first and second links configured to interconnect with one another in an unlocked position such that the first and second links angulate with respect to one another, each link defining a first surface configured to face a bone to which the bone fixation linkage is configured to be attached, a second surface opposite the first surface along a first direction, a first attachment member, a second attachment member spaced from the first attachment member along a second direction, perpendicular to the first direction, a first fixation hole that extends through the first attachment member, and a second fixation hole that extends through the second attachment member, the second fixation hole having a diameter greater than that of the first fixation hole,
wherein the first attachment member of each respective link defines a first geometry at the first surface of the respective link, the second attachment member of each respective link defines a second geometry at the second surface of the respective link, and the first geometry of the first link is configured to interlock with the second geometry of the second link when the first and second links are in a locked position so as to prevent relative angulation between the first and second links, and
wherein the first link has a first interior surface that defines the first fixation hole of the first link, and the first attachment member of the first link has a tapered surface that extends from the first interior surface to the second surface of the first link and surrounds the first fixation hole of the first link.

2. The bone fixation linkage of claim 1, wherein, for each respective link, the first geometry of the respective link aligned along a first plane and the second geometry of the respective link at the second attachment member is aligned along a second plane that is parallel to the first plane.

3. The bone fixation linkage of claim 1, wherein the first and second fixation holes of each respective link of the first and second links extend along respective first and second axes of the respective link from the first surface of the respective link to the second surface of the respective link, and the first axis of the first link is aligned with the second axis of the second link when the first and second links are coupled to one another.

4. The bone fixation linkage of claim 1, wherein the first geometry of the first link includes a first plurality of protrusions and recesses, and the second geometry of the second link includes a second plurality of protrusions and recesses that interlock with the first plurality of protrusions and recesses when the first and second links are coupled to each other.

5. The bone fixation linkage of claim 4, wherein the first link defines a first fixation hole that extends through the first attachment member of the first link, the second link defines a second fixation hole that extends through the second attachment member of the second link, the first plurality of protrusions and recesses of the first link extend radially out from the first fixation hole, and the second plurality of protrusions and recesses of the second link extend radially out from the second fixation hole.

6. The bone fixation linkage of claim 1, wherein each respective link of the first and second links includes a neck that extends from the first attachment member of the respective link to the second attachment member of the respective link.

7. The bone fixation linkage of claim 1, wherein each respective link of the first and second links comprises a monolithic body that includes the first and second attachment members of the respective link.

8. The bone fixation linkage of claim 1, wherein the first and second attachment members of the first link are spaced from one another along a first central axis, the first and second attachment members of the second link are spaced from one another along a second central axis, and the first geometry of the first link is configured to interlock with the second geometry of the second link when the first and second central axes are not aligned.

9. The bone fixation linkage of claim 1, wherein the first attachment member having the first hole is offset from the second attachment member having the second hole with respect to the first direction that extends from the first surface to the second surface.

10. The bone fixation linkage of claim 1, wherein the first link has a first interior surface that defines the first fixation hole of the first link, and the first surface of the first link has a portion that extends from the first interior surface along a plane, wherein the portion rests on the second surface of the second link when the first geometry of the first link is interlocked with the second geometry of the second link.

11. A bone fixation system comprising:
first and second links configured to interconnect with one another in an unlocked position such that the first and second links angulate with respect to one another, each link defining a first surface configured to face a bone to which the bone fixation linkage is configured to be attached, a second surface opposite the first surface along a first direction, a first attachment member, a second attachment member spaced from the first attachment member along a second direction that is perpendicular to the first direction, and first and second fixation holes that extend through the first and second attachment members, respectively, the first and second fixation holes configured to receive at least one bone anchor, and the second fixation hole being unthreaded,
wherein the first attachment member of each respective link defines a first geometry at the first surface of the respective link, the second attachment member of each respective link defines a second geometry at the second surface of the respective link, and the first geometry of the first link is configured to interlock with the second geometry of the second link when the first and second links are in a locked position so as to prevent relative angulation between the first and second links, and
wherein the first link has a first interior surface that defines the first fixation hole of the first link, and the first attachment member of the first link has a tapered surface that extends from the first interior surface to the second surface of the first link and surrounds the first fixation hole of the first link.

12. The bone fixation system of claim 11, comprising at least one bone anchor.

13. The bone fixation system of claim 12, wherein the at least one bone anchor is preloaded onto the first link, such that a portion of the at least one bone anchor extends through the first attachment member of the first link.

14. The bone fixation system of claim 12, wherein the at least one bone anchor comprises a head, a neck that extends from the head, and a shaft extends from the neck, and the at least one bone anchor is configured to capture the first attachment member between the head and the neck.

15. The bone fixation system of claim 14, wherein the neck has a diameter that is greater than that of the shaft.

16. The bone fixation system of claim 14, wherein the neck defines an outer cross-sectional dimension that is greater than a cross-sectional dimension of the first fixation hole.

17. The bone fixation system of claim 16, wherein the second fixation hole defines a cross-sectional dimension that is greater than the outer cross-sectional dimension of the neck.

18. The bone fixation system of claim 11, wherein the first geometry of the first link includes a first plurality of protrusions and recesses, and the second geometry of the second link includes a second plurality of protrusions and recesses that interlock with the first plurality of protrusions and recesses when the first and second links are coupled to each other.

19. The bone fixation system of claim 18, wherein the first plurality of protrusions and recesses of the first link extend radially out from the first fixation hole of the first link, and the second plurality of protrusions and recesses of the second link extend radially out from the second fixation hole of the second link.

20. The bone fixation system of claim 11, wherein the first and second attachment members of the first link are spaced from one another along a first central axis, the first and second attachment members of the second link are spaced from one another along a second central axis, and the first geometry of the first link is configured to interlock with the second geometry of the second link when the first and second central axes are not aligned.

21. The bone fixation linkage of claim 11, wherein the first link has a first interior surface that defines the first fixation hole of the first link, and the first surface of the first link has a portion that extends from the first interior surface along a plane, wherein the portion rests on the second surface of the second link when the first geometry of the first link is interlocked with the second geometry of the second link.

22. A bone fixation system comprising:
first and second links configured to interconnect with one another in an unlocked position such that the first and second links angulate with respect to one another, each link defining a first surface configured to face a bone to which the bone fixation linkage is configured to be attached, a second surface opposite the first surface along a first direction, a first attachment member, a second attachment member spaced from the first attachment member along a second direction that is perpendicular to the first direction, and first and second fixation holes that extend through the first and second attachment members, respectively, the first and second fixation holes configured to receive at least one bone anchor, wherein the first attachment member of each respective link defines a first geometry at the first surface of the respective link, the second attachment member of each respective link defines a second geometry at the second surface of the respective link, and the first geometry of the first link is configured to interlock with the second geometry of the second link when the first and second links are in a locked position so as to prevent relative angulation between the first and second links; and at least one bone anchor comprising a head, a neck that extends from the head, and a shaft extends from the neck, and the at least one bone anchor is configured to capture the first attachment member between the head and the neck, wherein the neck defines an outer cross-sectional dimension that is greater than a cross-sectional dimension of the first fixation hole, and the head has a cross-sectional dimension along a select direction that is perpendicular to a central axis of the bone anchor, the cross-sectional dimension of the head being greater than a cross-sectional dimension of the neck along the select direction.

23. The bone fixation system of claim 22, wherein the at least one bone anchor is preloaded onto the first link, such that a portion of the at least one bone anchor extends through the first attachment member of the first link.

24. The bone fixation system of claim 22, wherein the neck has a diameter that is greater than that of the shaft.

25. The bone fixation system of claim 22, wherein the second fixation hole defines a cross-sectional dimension that is greater than the outer cross-sectional dimension of the neck.

26. The bone fixation system of claim 22, wherein the bone anchor defines a recess between the head and the neck, the recess having a cross-sectional dimension along the select direction that is less than the cross-sectional dimensions of the head and the neck such that the at least one bone anchor is configured to capture the first attachment member in the recess between the head and the neck.

* * * * *